(12) United States Patent
Keshavjee et al.

(10) Patent No.: US 8,247,175 B2
(45) Date of Patent: Aug. 21, 2012

(54) DIAGNOSTIC ASSAY FOR LUNG TRANSPLANT

(75) Inventors: Shaf Keshavjee, Toronto (CA); Thomas K. Waddell, Toronto (CA); Mingyao Liu, Richmond Hill (CA)

(73) Assignee: University Health Network, Toronto, Ontario (CA)

( * ) Notice: Subject to any disclaimer, the term of this patent is extended or adjusted under 35 U.S.C. 154(b) by 660 days.

(21) Appl. No.: 11/670,684

(22) Filed: Feb. 2, 2007

(65) Prior Publication Data

US 2007/0218482 A1 Sep. 20, 2007

Related U.S. Application Data

(60) Provisional application No. 60/764,382, filed on Feb. 2, 2006.

(51) Int. Cl.
C12Q 1/68 (2006.01)
C07H 21/04 (2006.01)
C12P 19/34 (2006.01)

(52) U.S. Cl. ............ 435/6.11; 536/24.3; 435/91.2

(58) Field of Classification Search .................. None
See application file for complete search history.

(56) References Cited

OTHER PUBLICATIONS

Benner et al (Trends in Genetics (2001) vol. 17, pp. 414-418).*
Simon et al (American Journal of Physiology—Lung Cellular and Molecular physiology (2006) vol. 259, pp. L851-L861).*
Wiley et al (American Journal of Respiratory Cell Molecular biology (1996) vol. 14, pp. 262-271).*
Vandesompele et al (Genome Biology (2002) vol. 3 , pp. 1-11.*
Cheung et al (Nature Genetics, 2003, vol. 33, pp. 422-425).*
Wu (Journal of Pathology, 2001, vol. 195, pp. 53-65).*
Hegele et al (Arteriosclerosis, Thrombosis, and Vascular Biology. 2002;22:1058-1061).*
Gruber (Amercian Journal of respiratory Cell and Molecular Biology (2006) vol. 35, p. 65-71.*
Warrington (Physiological genomics (2000) vol. 2 p. 143-147.*
Anraku, M. et al.; "Impact of human donor lung gene expression profiles on survival after lung transplantation: a case-control study". American Journal of Transplantation, 2008; 8:2140-2148.
Anraku, M. et al.; "The impact of human donor lung gene expression profiles on survival after lung transplantation: a case-control study". The Journal of Heart and Lung Transplantation, Abstract No. 166, vol. 25, No. 2S, p. S101, Apr. 2006.
Kaneda, H. et al.; Pre-implantation multiple cytokine mRNA expression analysis of donr lung grafts predicts s after lung transplantation in humans. Am J Transplant. Mar. 2006;6(3):544-51.
Kaneda, H. et al.; "Rapid donor lung analysis in humans lung transplantation with quantitative multiplex rapid rt-pcr assay". The Journal of Heart and Lung Transplantation, Feb. 2005, Abstract No. 117, p. S80.
Kaneda, H. et al.; "Pre-implantation multiple cytokine mrna expression analysis in donor lung grafts predicts survival after lung transplantation in humans". The Journal of Heart and Lung Transplantation, Abstract No. 23, vol. 23, No. S2, p. S49, 2004.

* cited by examiner

*Primary Examiner* — Steven Pohnert
(74) *Attorney, Agent, or Firm* — Bereskin & Parr LLP; Micheline Gravelle; Carmela DeLuca

(57) ABSTRACT

Methods and compositions for determining the suitability of a lung for transplantation are described.

12 Claims, 4 Drawing Sheets

SEQUENCE LISTING

<160> NUMBER OF SEQ ID NOS: 215

<210> SEQ ID NO 1
<211> LENGTH: 229
<212> TYPE: DNA
<213> ORGANISM: human

<400> SEQUENCE: 1
ggcttattcc cacaggaagc ctcctaaagc ctgtggcgcg gcaaccattt ccaggactaa      60
ataataatgt gtcagatgcc tgtgagtgga ctgcctggcc aaatgactca tgaagatatt     120
cacggaagaa tagtcaaaaa ccaaagaaaa ggcatattct agaagcacct tcaattccat     180
cgaggatttt tgagcagctg aagaagaaag ttctgaaaat atgagtgac                 229

<210> SEQ ID NO 2
<211> LENGTH: 268
<212> TYPE: DNA
<213> ORGANISM: human
<220> FEATURE:
<221> NAME/KEY: misc_feature
<222> LOCATION: (232)..(232)
<223> OTHER INFORMATION: n is a, c, g, or t

<400> SEQUENCE: 2 cttttaacc atcttttttc ccctccctc tgagacatcc gaattgtggg cgagcagtgt       60
gatttctctg tggctggccg tgccacactc acccccagag cacttatgtt aacttggaac    120
tgtttagaga gaatttttt gctttcttgg gtcacatggc tcagtagcca ttagccatag     180
cttgattttg caaactggca agggcctggc acacctttcc ttccaccagg gnatggtgtt    240
tctggaagag tttgaagcta gatcctgg                                        268

<210> SEQ ID NO 3
<211> LENGTH: 518
<212> TYPE: DNA
<213> ORGANISM: human
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t

<400> SEQUENCE: 3 gaaattttc ccaagttttg tacattaagc acaaaattat aacaggaaaa taagaaaag       60 aatttaaaat aaacatgcaa ccaaatttta aacagataag tatatcgtat tagataggaa    120
tcaccatact gggtcagtca cccctcctcc aaattttct ttattctttt tttttatta      180 tactttaagt tttagggtac atgtgcacaa cgngcaggtt tgttacatat gtatacatgt    240
gccatgttgg ngngctgtac ccattaactc gtcatttacc attaggtata tctcctaatg    300
ctatccctcc ccctccccc caccccacaa taggccctgg tgtgtgatgt tccccttcct    360
gtgtccatgt gatctcattg ttcgattccc acctatgagt gagaatacgt ggtgtttggt    420

| | |
|---|---|
| tttttgtcct tgtattagtt tgctgagaat gatggttcca gcttcatcca tgtccctaca | 480 |
| aaggacacga actcatcatt ttttatgctg catagnat | 518 |

```
<210> SEQ ID NO 4
<211> LENGTH: 229
<212> TYPE: DNA
<213> ORGANISM: human

<400> SEQUENCE: 4
```

| | |
|---|---|
| agggcgagcg aggaggatgg cggagtcggg tctcctgacg gaactctaat gaatcattga | 60 |
| ttgaccagca ctattttacc agttggaatg aatgatcaga atgggcata gtgcttttag | 120 |
| atccaacatg taacagatgg atgttactcc atgctgatta cttcttcaag ccagttgatg | 180 |
| agctcactta taacatggtt acataactgt gattatataa tgcacagga | 229 |

```
<210> SEQ ID NO 5
<211> LENGTH: 216
<212> TYPE: DNA
<213> ORGANISM: human

<400> SEQUENCE: 5
```

| | |
|---|---|
| gtgagatgtg cctttcaccc tctgccataa ttgtgaagcc ttcccagcca tgtggaacca | 60 |
| taagtctatt aaaattcttt cttttgtaaa ttgcccagtc ttgggtatgt ctttataagc | 120 |
| agcatgagaa tggactgatg cagagtggta ttagaactta aaaaaaaaaa aaagttattt | 180 |
| gaaattaccct tgagtttcct ctgggggggcc cttcaa | 216 |

```
<210> SEQ ID NO 6
<211> LENGTH: 229
<212> TYPE: DNA
<213> ORGANISM: human
<220> FEATURE:
<221> NAME/KEY: misc_feature
<222> LOCATION: (1)..(1)
<223> OTHER INFORMATION: n is a, c, g, or t

<400> SEQUENCE: 6
```

| | |
|---|---|
| ngccctgaag tgcctgagcc accatgttgc agatgcctac acctcttccc agaaagtctc | 60 |
| tcccattcag attgatgggg ctggaaggac ctggcaggac agtgacacgg tcaagctgtt | 120 |
| ggttgacctg gagctgagct atgggtttga gaatggccag aaggctgctg tggtacacca | 180 |
| cttcgaatcc ttccctgccg gctccacttt gatcttctat aagtattgt | 229 |

```
<210> SEQ ID NO 7
<211> LENGTH: 448
<212> TYPE: DNA
<213> ORGANISM: human
<220> FEATURE:
<221> NAME/KEY: misc_feature
<222> LOCATION: (438)..(438)
<223> OTHER INFORMATION: n is a, c, g, or t

<400> SEQUENCE: 7
```

| | |
|---|---|
| gacagaattg gtcttgaatt ccaaacctgc tatttacatt ctgtttcaca aggtgagata | 60 |
| atgtatgaaa aattgcttaa ggcagtgtct tcctcccaca agaaaaggc agctacagat | 120 |
| gcagttattt gctattatgc aattcagtga gaggccattg tagaggatat tctccaaaac | 180 |
| tccctgacaa tgagtcactt cctgattgat aatttcacat agctgcattc ttaggagctc | 240 |
| acttgggaac ctaaaccatg gagaagttaa gattttgtct cagaagtctc ctctgagaca | 300 |
| taggtcctct gagacacagg ctactttaag gaaaagaaaa aaaatcacct gggttctgtt | 360 |

```
cctgactact gctgactagc tgtgctgtat ggagtgggtt cactttcctt tccttttctt    420
tctttctttt ttttttcncc agcctggg                                      448

<210> SEQ ID NO 8
<211> LENGTH: 229
<212> TYPE: DNA
<213> ORGANISM: human

<400> SEQUENCE: 8
caggtaggct tattctttcc ccagattaaa caagagccct gccaacacta ggcaagtctg     60
gtggctctag caaggggggaa ttgatttgga accactggca atcagtgacc agggagaagc   120
attctccttc cctcctgggc atgagactcc ccttccccac tgacagacac tgggtggcca   180
gtgtgcctgg caaggggggat gtcctcacaa atgcctagcc cagaaagtg              229

<210> SEQ ID NO 9
<211> LENGTH: 229
<212> TYPE: DNA
<213> ORGANISM: human

<400> SEQUENCE: 9
gaagactttt gtcttgttgt agaagatgtt ttttttctct tattttgagt aaaaagtgag     60
aggaattgca ggaacacata taagcacatg cttatttttt ttaaagaaac tgttcaacta   120
ttttccttag ttgagaattt tatactccca aaagcagtga tgtaccagag ccccacttgt   180
ttcacatctt cagcatcact tgcaactaat caatcttcaa ttttagctg               229

<210> SEQ ID NO 10
<211> LENGTH: 211
<212> TYPE: DNA
<213> ORGANISM: human
<220> FEATURE:
<221> NAME/KEY: misc_feature
<222> LOCATION: (207)..(207)
<223> OTHER INFORMATION: n is a, c, g, or t

<400> SEQUENCE: 10
gcaaataaag tagtaaaaga agaaatagtt ctgtgactag gaaaaaattg cttttgagag     60
aacatagatc aattatacta cttctaaggt agctgcagat aagtggcctt gacacattac   120
aagcccggaa aaaacatca gaaataataa aaaatttcag agagaatcaa gatacctttt   180
tttttctttt ttttttttttt tttaatnaaa c                                 211

<210> SEQ ID NO 11
<211> LENGTH: 229
<212> TYPE: DNA
<213> ORGANISM: human
<220> FEATURE:
<221> NAME/KEY: misc_feature
<222> LOCATION: (85)..(85)
<223> OTHER INFORMATION: n is a, c, g, or t

<400> SEQUENCE: 11
agtattttta gaatcatata ctgtcttaaa atacatcagt gataatgtta acacttcttc     60
ctacctgcat aaactgatga tcacnatgaa aaaatagatt aatgtctttt tttaatgctg   120
aactcaagtt ctctttgtta agtatacttg cacattttta tcttggtata ttgaactctc   180
ttggtcttat acagaccatt ccaagtggtc tgacatacat acgcctgat               229

<210> SEQ ID NO 12
<211> LENGTH: 230
<212> TYPE: DNA
```

<210> SEQ ID NO 12
<211> LENGTH: 230
<212> TYPE: DNA
<213> ORGANISM: human

<400> SEQUENCE: 12
gaaacaggta cctgtggatg tggtcgagat gaaaggcaag ttgtatttta gtcactttga      60
ggcgaatggg gcctacgtgc tgttttactc ttggctttaa cacttccatg cgaggggttg     120
tctgagcagc tgagtcagga ctgtgagccc tcaccatgaa tagtcatctc caggtcacag     180
aacgtgttta gagcttgggc aacatagtga gaccctctct gtacaaaaaa                230

<210> SEQ ID NO 13
<211> LENGTH: 229
<212> TYPE: DNA
<213> ORGANISM: human

<400> SEQUENCE: 13
agttttatgt attacaaaac cacataaaca gtgcttcttg gtctgtaggc ccacctgtgc      60
agtggacttc tggatttctc tgtgtgctct gaggaaggga tccaagtggc cattgttgac     120
aggccattgg cctgtgttga cagcttgttt ctgttatgcc tttgctcagt atagtcttgc     180
tggtggtagc gacaggggga agtgaaagac cactgagtgc ctcttaaat                 229

<210> SEQ ID NO 14
<211> LENGTH: 229
<212> TYPE: DNA
<213> ORGANISM: human

<400> SEQUENCE: 14
gatgaatcca ggagttccgg ttgcagtgag ccgtgatcac accactgtac ttcagcctgg      60
gtgagagcaa gaccttgtct ttaaaaagta aagagtaaaa acaaattgtg atacagtcat     120
acgatggagt attattgagc aagtcaaagg aaaggactgc tgatacaaca cggacaaatc     180
tcaaaaacat tgcatttggc aaaagaagcc agacacagag tacatagca                229

<210> SEQ ID NO 15
<211> LENGTH: 147
<212> TYPE: DNA
<213> ORGANISM: human

<400> SEQUENCE: 15
gtgacttaca catcataaat gactttcaaa tgaaatttga atttcaaaat tctgtaaaag      60
tggttgctca aaagatgtat gatactattt taatcagttt aagagcaaaa atgtctaatt     120
gtatttaaca atggtatttg ggcagcc                                         147

<210> SEQ ID NO 16
<211> LENGTH: 230
<212> TYPE: DNA
<213> ORGANISM: human

<400> SEQUENCE: 16
gattttattg aggattttg catcgatgtt catcagggtc taaaattctc ttttttttgtt      60
gtgtctctgc caggttttgg tatcaggatg atacccctaac tcattttatg aggccagcat    120
catcctgata ccaaagcctg aattcatcta ttttctaatc aacgtaggaa gacttcacgg     180
aggtggaaag tgagtcctct ctggtaggaa aggtagggat ttaaaaatcc                230

<210> SEQ ID NO 17
<211> LENGTH: 229
<212> TYPE: DNA
<213> ORGANISM: human

```
<400> SEQUENCE: 17
gagaatgcag tatctgaaat aaaatatata ttggatggga ttaatagcag ataagacaca    60
catcagtggg cttgaataga taacaatagt gactatccaa aatgaagcac agggtggaag   120
gactaaagaa aaaacagca tcagtgagct gtgggaaata tcgagtggcc taagacgtgt   180
aattagaatc ctaggagaag ggaggggcaa cagaaaatat tataagaaa              229

<210> SEQ ID NO 18
<211> LENGTH: 229
<212> TYPE: DNA
<213> ORGANISM: human

<400> SEQUENCE: 18
gttgttcact gttataccca ctccacttcc taggaaatgc ctagaaatag aaggaactca    60
gtaaatactt cctggaacag aaaccccaat cgttcatgaa ttctcagagc atccctttct   120
gtgataatag agtggagaaa aacttcctgt gggtctgcaa tcctatcccc gcacagaaag   180
gctgtcacca tttgaccaaa agggaggacc aggacagaag gaccataag               229

<210> SEQ ID NO 19
<211> LENGTH: 512
<212> TYPE: DNA
<213> ORGANISM: human

<400> SEQUENCE: 19
caccaacaat atcccagaac tcaaatatta tgataagaca gttcgtgggg ccacagagaa    60
gtaaaaaatc accaagaaga cagtaagaga atcaaacttc catattcatg atatcctttt   120
ccccagtgtg cctgacacca agtgtgtgga aaatttcccc ccaactcaca gtttctacag   180
tggaaaaagt gagactgagg tgaacaacca gcttctccac aatcttgagt tttctggtga   240
gaaatctttc cctgcctcaa tgcacaagaa gtgttgagag taccagaagg gagaatatcc   300
ctgaggaaag ccagagacaa agtggtgagg tagaaatacc atccttatct ctggaaactc   360
tgctctatat cttggccaaa ggagacgcca aatcaaagtg gctgtttagc agcaccacac   420
agtaagagtt tcatctcaca ggtccctggg taaaacccct ggctggcttc cccctactg    480 ggatatcctc ttgggactct ccattcagat gg                                 512

<210> SEQ ID NO 20
<211> LENGTH: 229
<212> TYPE: DNA
<213> ORGANISM: human
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (176)..(177)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t

<400> SEQUENCE: 20
```

```
gatgaataga agctatgttt gggacgagng gtcactggct cacagtgacg actctgattt      60
tagagggacg gaacgaggac aggacgattg tgatttttaga ggtgctgaac aagtacttat    120
tagcttagtg cagaaataag agancacaac tatccccct aatantcaac caccgnngac     180
tgcagcccct gaggatggcc gcctgacagc ttgggagcgc ctcggnagt                 229
```

```
<210> SEQ ID NO 21
<211> LENGTH: 229
<212> TYPE: DNA
<213> ORGANISM: human

<400> SEQUENCE: 21
ggaaaagtag agaaatggat tcagtataag gataaggagg gaaggtggac cagaatgaaa     60
actgtaaata tttttttaac ctaatatcac ttaaatcgag gcagaaagat atagacattc    120
aatgaattat attcaatgca tttaaaatac cactgtaatt gacagagtaa aagtatagat    180
acaaaacctt gtgtaagagg ctgactttc caaataaaca tttttttaag                229
```

```
<210> SEQ ID NO 22
<211> LENGTH: 229
<212> TYPE: DNA
<213> ORGANISM: human

<400> SEQUENCE: 22
agcaggggga aaatgcctga tctggaagtt gtgtctgtta tttccagtca cttcccattg     60
ttcagaattt agtcacctgg tcatatccta gctataaatt tgggttggaa atgtgtttct   120
tctgggcagt tgtatgccca gctaaaaatc tattatatag caggagggag aaattaatat   180
tgggggaaca accagacatc tctgccacaa tcaagacttt gttttgtat                 229
```

```
<210> SEQ ID NO 23
<211> LENGTH: 229
<212> TYPE: DNA
<213> ORGANISM: human
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (152)..(153)
<223> OTHER INFORMATION: n is a, c, g, or t

<400> SEQUENCE: 23
ggtgcagcct agtgttggng ctgctgctgg gccagtggtt cctccatgtc cggggaggat     60
cagacacttc aaggtctagg ctanacatgg cagagatgag gaggtttggc acagaaaaca   120
tagccaccat tttgtccaag cctgggcatg gnnggggggc cttgtctgct ggccacgcaa   180
gtgtcacatg cgatctacat taatatcaag tcttgactcc ctacttccc                 229
```

```
<210> SEQ ID NO 24
<211> LENGTH: 229
<212> TYPE: DNA
<213> ORGANISM: human

<400> SEQUENCE: 24
gatagatagc aaattgtctc agtctcattt attgaggagt cagtcttctt tccctattga     60
tttgaaatat tataacccaa atttccacaa atgcatgggt tagtttctgg gcactagtga   120
```

```
tttgctcacc taatcccaaa tcagcaccac acttatttaa ttattatagc tttacagtat    180
gacttcatat cttatgagta aaatttgttc tcttaaaaaa ttgtcttgg                229

<210> SEQ ID NO 25
<211> LENGTH: 229
<212> TYPE: DNA
<213> ORGANISM: human

<400> SEQUENCE: 25
gcctgacaac tctttgcctt cattttccta tctgtgaaac agttttgctc attttgctac     60
ccttagaata aattctacaa tgtctatgtc gatttaagcc ccttcctaga atgacaacta    120
caggaggctg cttcaagggt gttcgtgtag cccaaacctc ccttttctga agaaatgcc    180 tcccctgca caggactgga caccaggagc cagatcactc aaatgatgc                229

<210> SEQ ID NO 26
<211> LENGTH: 485
<212> TYPE: DNA
<213> ORGANISM: human
<220> FEATURE:
<221> NAME/KEY: misc_feature
<222> LOCATION: (482)..(482)
<223> OTHER INFORMATION: n is a, c, g, or t

<400> SEQUENCE: 26
cccttccccg aaactcaacc acccttgtaa tactgagaga ccaccaggct aggaggagga     60
gaggagccta aattctgcta aggtgtagac aaaaacaatt gtgaggcgtt attccagaag    120
ccacaagata tgcaacttcc tcagttaccc ctgcagataa tgttacttttt gtagaaccta   180 ggattggcct tctgagatat cttctcagga ttttgcatgt ctgatgaccg atggctccac    240
cgggaccagc caacggcttc tgtgtcccca cccagaagcg actcagagaa agaggacagc    300
ttcgacaccc tatgatttca tctctgaccc aaccaatcag cactcccat acccctagcct   360 gctacctacc aaattacctt tgaaaaatcc ctaacctcca agccttagat gagtttgatt    420
tgagtaataa ctctgcctcc cacatggtgt ggctggcatc atgtcaatta acctcttctt    480 tnctg                                                                485

<210> SEQ ID NO 27
<211> LENGTH: 229
<212> TYPE: DNA
<213> ORGANISM: human

<400> SEQUENCE: 27
cccccaccaa ctccagtaac accagccaga ggctcaggga cagaacctgc atctccctgg     60
tcctgtgtcc ctaggggag ggatggctgc agtctctgtg gaccagcaga cttagccttt    120
cctcctggta gttctgagga atccaggcag cccagacaag tgggttcccc gcaagtgagg    180
cactgtgtta aacaggttct gttccccatg ccacccaact gggtgagac                229

<210> SEQ ID NO 28
<211> LENGTH: 229
<212> TYPE: DNA
<213> ORGANISM: human

<400> SEQUENCE: 28
tggcgggctc ccctccccca gcctcgctgc tgccttgcag tttgatctca gactgctgtg     60
ctagcaatca gcgagactcc gtgggcgtag gaccctccga gccaggtgtg ggatatagtc    120
tcgtggtgcg ccgttttttta agcccgtcgg aaaagcgcag tattcgggtg ggagtgaccc    180
```

```
gattttccag gtgcgtccgt cacccctttc tttgactcgg aaagggaac          229
```

<210> SEQ ID NO 29
<211> LENGTH: 420
<212> TYPE: DNA
<213> ORGANISM: human

<400> SEQUENCE: 29

```
gtgaattgct cctctcccaa aatgcatttg tatcatgtct ttgcagcaag aagtgactat    60
atctctgtga atgctacata cattaccata ttgtaattta acaccaaagg cattagctgc   120
accaactttt tatttattgt gatcttgaaa aacacatggt cttcacattt tttgatgagg   180
gtcattaaaa aatatttatg gaatatgcat gtcaatccca gatatattga aatgagtaaa   240
ccttcatatt atgctgttgg ctacataaca gagcaatagc tggaactact ttgccttgga   300
ctcttaaaac aggaaagatt ttatatactt cattgtccaa gagttatcta gataccaagt   360
gatgtgaagt gctctgacag tttcttgatt tcattcacat acatttctaa aaacattccc   420
```

<210> SEQ ID NO 30
<211> LENGTH: 229
<212> TYPE: DNA
<213> ORGANISM: human
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (115)..(115)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t

<400> SEQUENCE: 30

```
tctcaccgac acgactcacg aaactctcaa acacgaactc cnactcaaca ngggaaactc    60
tcggcccanc gaggccaaga aacncggcac gagggcggag gttgtggcga gccangatcg   120
```

```
cgctgttgca cnccagcctg ggcaacaaga gcgaaacncc anctcaaaaa aaaaacaaaa    180
gacaaaacaa acaaaaaaaa accttttanc ttctgattta angnggcaa                229
```

<210> SEQ ID NO 31
<211> LENGTH: 150
<212> TYPE: DNA
<213> ORGANISM: human

<400> SEQUENCE: 31

```
ggtggtgggt acctataatc ccagctactt gggaggctga agcaggagag tcacttgaac    60
ctgggaagca gaagttgttt tgagccaaga tcatgccatt gcactccagc ctgggcgaca   120
agagcagaac tctgtctcaa aaaaaaaaaa                                    150
```

<210> SEQ ID NO 32
<211> LENGTH: 165
<212> TYPE: DNA
<213> ORGANISM: human
<220> FEATURE:
<221> NAME/KEY: misc_feature
<222> LOCATION: (28)..(28)
<223> OTHER INFORMATION: n is a, c, g, or t

<400> SEQUENCE: 32

```
cctccatcag cattttcaaa tttcaggntc tggcctttca ccgaatgcac ttcccaccag    60
tcctgtttac actgccaggt tccgctagga gctttcccac ctctgcaggg gcaggcctcg   120
ctgcttctta aggcctttct ctggggtggg aggaaacgga aactg                   165
```

<210> SEQ ID NO 33
<211> LENGTH: 390
<212> TYPE: DNA
<213> ORGANISM: human

<400> SEQUENCE: 33

```
ggctaataca tgccgacggg cgctgacccc cttcgcgggg gggatgcgtg catttatcag    60
atcaaaacca acccggtcag cccctctccg gccccggccg ggggcgggc gccggcggct    120 ttggtgactc tagataacct cgggccgatc gcacgccccc cgtggcggcg acgacccatt   180
cgaacgtctg ccctatcaac tttcgatggt agtcgccgtg cctaccatgg tgaccacggg   240
tgacggggaa tcagggttcg attccggaga gggagcctga gaaacggcta ccacatccaa   300
ggaaggcagc aggcgcgcaa attacccact cccccggggg ggttcgcctc ctctccttgg   360
gggctttatg tcttctctcc ccactgcagg                                    390
```

<210> SEQ ID NO 34
<211> LENGTH: 462
<212> TYPE: DNA
<213> ORGANISM: human
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t

<400> SEQUENCE: 34

```
aaacngcctg ccacccagtc ttaggctcag taaaaatgct cattagaaga attttcttag    60
gataattcct tagaatctgg aagctactgc aaatatttta ggtttggcat agaactgaaa   120
tcaacagaac atttaaaaat tgattggagc cttctggatt tacctctgac atgtaacaag   180
```

```
cttagaagtc attatgccct tcctaataat aagaaaaacc tgaacaaact aaaaacaata      240
tctttattgg acctgtcagg ggactatggt cacagggaaa atcaccaccc tgaaatctgg      300
aaagacaggt gaatagagtc acagctgaga ttggcttgct ctggacccat gttttttat       360 tgtctattct gattatttga catctggggc cttgctgctc gtggagggac tgccattctc      420
agggttcatc aattcctaga gaccgntaac aactcacgtg tg                         462
```

<210> SEQ ID NO 35
<211> LENGTH: 425
<212> TYPE: DNA
<213> ORGANISM: human
<220> FEATURE:
<221> NAME/KEY: misc_feature
<222> LOCATION: (378)..(378)
<223> OTHER INFORMATION: n is a, c, g, or t

<400> SEQUENCE: 35

```
gcaggttagt tacatatgta tacatgtgcc atgctggtgc actgcaccca ctaactcgtc      60
atctagcatt aggtatttac tttatttaa aatggcaaat gaggaaacaa acaaaagggg       120
actgcacagc ttgttgtgaa ccaagacaaa gaacttgtaa tcctgggact cctcaaagct      180
caccaaattc cattcaaccc ttcataaagc taacctgcag agtgcactcc ccgacacgtg      240
tgagacaaat gagatgcgat gagagatgaa gccaaaaaag cagcactccc ctgtgtcttc      300
aattagccac gggagtgaaa atgagacaaa cagtcatgta taatttagag ggttgctctc      360
cggttcttcc tgccgtgnga agcctttcac cgaggaagga agcgtgatcc agtaagtgct      420
caggc                                                                 425
```

<210> SEQ ID NO 36
<211> LENGTH: 393
<212> TYPE: DNA
<213> ORGANISM: human
<220> FEATURE:
<221> NAME/KEY: misc_feature
<222> LOCATION: (388)..(388)
<223> OTHER INFORMATION: n is a, c, g, or t

<400> SEQUENCE: 36

```
gtttctttag agttaatatg cagtctttta ttttacatta agtactctta tgatttcatg      60
tcttcacaaa attgcgctta acttttgaag taggaggtac tttaaacaaa atactgtgc       120 catgtcagca cttttttcct tttaaatatt gaaataaata aaatagttaa ctcttttttt      180
ccatcagttt gtttgtgttc agttatttct actgtagagt aattccaggc ggacctgggt      240
actttctcac agacaatcaa agaaaatata atgaagattt aaaagaaaa aaaaaatctt       300 cttattgcac aaactgaggc cattcccaag gcttctgtgg gctgagctga gttgcgctgc      360 aggatttttcc actcctgtgc tggctccngg ttg                                  393
```

<210> SEQ ID NO 37
<211> LENGTH: 537
<212> TYPE: DNA
<213> ORGANISM: human
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t

<400> SEQUENCE: 37

```
caccatggaa tactatgcag caataaaaag gaatgagatc ctgtcctttt cagggacatg    60
gatggagttg gaagctgtta tcctcagcaa actaatgcag gaacagaaaa ccaaccacca   120
catgttctca cttataagtg ggagctgaac aatagaacac atgggcacag ggaggggaat   180
aacacacact ggggccagtc aggggtgggg ggtcaagct gagggagagc attagaaaaa   240
atagctaatg cattctgggc ttaacccatt tatgcctagt gttccatttc tggaatgcta   300
agcatgtgga agttctttat atcctgctca aggtcattgc caaggtctga tttttcacat   360
tcaacaaatt gcaacctctg cataaatgg gnttaatacc taggtgatga gttgataggt   420
gcaggaaacc accatggcac atgtttatct atgtaagaaa cctgcacatc ctacacatgt   480
accctggaac ttaaaaattt aaaaatatat gtatatatat tnatatggaa tttaaaa      537
```

```
<210> SEQ ID NO 38
<211> LENGTH: 512
<212> TYPE: DNA
<213> ORGANISM: human

<400> SEQUENCE: 38
gtcctgccca gggtgaactc accctcgagc cagccaaact ggtgaatgcc cttccccaag    60
cgggagaagc cctcatatct ccaagcagcc aacatgcttc tgggttgaag gagcagctat   120
gtgcccacac ccaggtcctg agaaacagcc gcacagtgcc ccacccacta cagacaagcc   180
ccagtcccgc ccaacagctt tgtatccaca attagagcct gcgaaacaga cctgtgtgct   240
gcccctgaca gacatgctcc ttggctatct gaacagctct gcgctcacat gccaggactg   300
agaaatagtc tgcaggccac ccctggtggg aaagccctcg agtcagccaa ttatccctgt   360
gcccatatcc caggctgaga gcagccctc caagcagtat cttgtgggca gatacttcca   420
aaggaagcaa aagacctcta catgaaaact acaaacactt atgaaagaat tgaggagata   480
caacaagtga gaaatatctc atgccatgga ta                                 512
```

```
<210> SEQ ID NO 39
<211> LENGTH: 564
<212> TYPE: DNA
<213> ORGANISM: human

<400> SEQUENCE: 39
ggttaaatta agcctgtagg tgcacagagt gcaagaattg aggcttggga gcctccaact    60
agatttcaga gtatgtgtgg gaaagcctgg atgtccaggc agaagccagc tgcagggaca   120
gagccctcat ggagaacctc tactaggta gtgtggaggg gaaatttggg gttggagttc   180
ccacacagct tcccctctgg tgtactgcct agtggagctg tgagaagaca gccactgtcc   240
tccagattcc aggatgatag atctgccaat gacagcttgc actgtacaac tggaaaagcc   300
acaggcagtc aatgccagcc cgtgaaagca gtgacagtgg cttaccctgc aaagtcccag   360
gggctgagct gcccaaggcc ttgggagccc accccttgca ccagtgtgcc ctggatgtga   420
gatatggagt caaaggagac tattttggag ctttaagatt taatgactac ctgctgggtt   480
tcagacttgc atgggccag tagccccttt cctttggcca atttctcact tttggaatgg   540
gagtgtttac ccattcctgt accc                                          564
```

```
<210> SEQ ID NO 40
<211> LENGTH: 364
<212> TYPE: DNA
<213> ORGANISM: human

<400> SEQUENCE: 40
```

```
cggcacgaga aaaaagatat atacttaggt gtgtagtagc tggttcacag gcatgcatag      60
cctcaactta tataagttat gccaacttgt gttctgaagt gggcatggca gcttatgctc     120
ccagcaggag tctatgagaa ttcttgttgt acatcctcac caacatttgg gattgtgaga     180
cctcatgttt tatccatcta ttcagctgga agtgaaatct cagaggggtt tttaagttgc     240
ttactagtga gcatgagcat cttttcatat gttgcttggc ccttcctgtt tccccatctg     300
tgatttgacc attcaaggtg tttgcctact tttcaatggg tctattcttt ttgttattga     360
tttg                                                                   364

<210> SEQ ID NO 41
<211> LENGTH: 298
<212> TYPE: DNA
<213> ORGANISM: human
<220> FEATURE:
<221> NAME/KEY: misc_feature
<222> LOCATION: (282)..(282)
<223> OTHER INFORMATION: n is a, c, g, or t

<400> SEQUENCE: 41
gagagctagc accatgagct tcaatacccct gcccatcttc tctggaaacc ctcctaataa      60
atctttccca caaatcctca cagaaagcac tgcctctggg gacctagcct aaggcaaggt     120
agatgcagga ttcaaaccca agcctgtgtg tcttcaaagt ttttttccca ctatgttgtg     180
gttgagatgt tattacaatc gtgttggtct gctctttgtt catttacag ttatacattt      240 aaaatgcatc atacaacccct gtctctacta aaaatacaaa anaaaaaaaa aaaaaaa       298

<210> SEQ ID NO 42
<211> LENGTH: 379
<212> TYPE: DNA
<213> ORGANISM: human
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t

<400> SEQUENCE: 42
gatatatgta gcacaacagg aacagaagcg tatttaaagt catctctagc ttaccagaaa      60 caccccctaaa actgctggtt tagattcatt aatcaacctc atggtcctca gatgggttgt     120
gactccctgn tgcgtaaaca cgaaccatgt tacttcctgg tcctcctgac ctccactatt     180
tgatttctac gaggatcagg agttaggtcg ccagctgatc taaagcagcg agtcccaaag     240
ttcagccatt tgtaaaccac ctgcatggtt ttggaccaac tcttgtgtca ccccatagtt     300 tctcanatttt aatatgcat acaagtggca tgggatatgt tgctcaaatg cggaattctg     360
gttcattaan agtgagagg                                                   379

<210> SEQ ID NO 43
<211> LENGTH: 509
<212> TYPE: DNA
<213> ORGANISM: human
<220> FEATURE:
<221> NAME/KEY: misc_feature
<222> LOCATION: (379)..(379)
<223> OTHER INFORMATION: n is a, c, g, or t
<220> FEATURE:
```

```
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (442)..(442)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t

<400> SEQUENCE: 43
gaaatctgac atagttgact ccttcttgct tctagctttc aagctgtcct tggtcattcc    60
taggcattgg ccaagctaat tttgggagga tttagtttat agtttaacct taaagcaagg   120
atgataatag cccttcccaa aactaaactg cttttgtaaa attaatgaga ggccaaaaga   180
ttaggattat gctgggggct tgaattctgc taagacatag gcatagttaa ataacaacca   240
gccattgttc cagaggtcac aagatttgta acttctccaa ttactcctat agatggcatc   300
actattgtag aacctaagat tgctcttttg agatatttt cagactttgc attttggcaa    360
ctgactgact ccacctggna ctcatgactc aactggtctt gtggcccccn accaagagct   420
gggctcagca catgaggang gntttcccac ccctatgatt gcatcccac ccatcaggag    480 cactcattcc tgaatccgga accacnaaa                                     509

<210> SEQ ID NO 44
<211> LENGTH: 501
<212> TYPE: DNA
<213> ORGANISM: human
<220> FEATURE:
<221> NAME/KEY: misc_feature
<222> LOCATION: (1)..(1)
<223> OTHER INFORMATION: n is a, c, g, or t

<400> SEQUENCE: 44
natgaacttc gggatgaagg gaaggcttcg tctgccaaac agagactcaa gtgtgccagt    60
ctccaaaaat ttggagaaag agctttcaaa gcatgggcag tagctcgcct gagccagaga   120
tttcccaaag ctgagtttgc agaagtttcc aagttagtga cagatcttac caaagtccac   180
acggaatgct gccatggaga tctgcttgaa tgtgctgatg acagggcgga ccttgccaag   240
tatatctgtg aaaatcaaga ttcgatctcc agtaaactga aggaatgctg tgaaaaacct   300
ctgttggaaa atcccactg cattgccgaa gtggaaaatg atgagatgcc tgctgacttg    360
ccttcattag ctgctgattt tgttgaaagt aaggatgttt gcaaaaacta tgctgaggca   420
aaggatgtct tcctgggcat gttttttgtat gaatatgcaa gaaggcatcc tgattactct   480
gtcgtgctgc tgctgagact g                                             501

<210> SEQ ID NO 45
<211> LENGTH: 353
<212> TYPE: DNA
<213> ORGANISM: human
<220> FEATURE:
<221> NAME/KEY: misc_feature
<222> LOCATION: (327)..(327)
<223> OTHER INFORMATION: n is a, c, g, or t

<400> SEQUENCE: 45
gggagttaag tgtagaagtg tttcttcttt tcatttttct ttgtttctat tacttgtaat    60
```

| | |
|---|---|
| ctaagataag ttgtcatctc tttaaaataa cctgttatat ctataaaatg tatttttgtaa | 120 |
| gctttatggt aaacacaata caaaaaccta taatagattc actaaaagta aaaagcaaca | 180 |
| aattaaaaca tactgttaac cacaaaggaa gacagaaaaa tgaagactct taaatattta | 240 |
| agcaaaaaaa gaagacagta agaaaggaag aaagaaaggg aggagttaca aacaaccaga | 300 |
| aacaagcaac aaatggcagt agtaagncttt actaatcaat aatacactga atg | 353 |

<210> SEQ ID NO 46
<211> LENGTH: 441
<212> TYPE: DNA
<213> ORGANISM: human

<400> SEQUENCE: 46

| | |
|---|---|
| tggcgggctc ccctccccca gcctcgctgc tgccttgcag tttgatctca gactgctgtg | 60 |
| ctagcaatca gcgagactcc gtgggcgtag gaccctccga gccaggtgtg ggatatagtc | 120 |
| tcgtggtgcg ccgttttta agcccgtcgg aaaagcgcag tattcgggtg ggagtgaccc | 180 |
| gattttccag gtgcgtccgt cacccctttc tttgactcgg aaagggaact ccctgacccc | 240 |
| ttgcgcttcc caagtgaggc aatgcctcgc cctgcttcgg ctcgcgcacg gtgcgcgcac | 300 |
| ccactggcct gcgcccactg tctggcactc cctagagaga tgaacccggt acctcagatg | 360 |
| gaaatgcaga atcaccgtc ttctgcgtcg ctcacgctgg gagctgtaga cagagctgtt | 420 |
| cctattcggc catcttggct c | 441 |

<210> SEQ ID NO 47
<211> LENGTH: 612
<212> TYPE: DNA
<213> ORGANISM: human
<220> FEATURE:
<221> NAME/KEY: misc_feature
<222> LOCATION: (594)..(594)
<223> OTHER INFORMATION: n is a, c, g, or t

<400> SEQUENCE: 47

| | |
|---|---|
| gaatgatgct gtgagacaat ctgagaagaa ttaaaattta aattcatgta ttcctacttt | 60 |
| tttctctgtt ctctaactgt aaaatatttt cattacagat ggaggaacaa atagatgtta | 120 |
| gataaataga tatataatag atcatccaaa attcttattc ttatggtttt atgtagtcag | 180 |
| tatttacctc tatttttcta catgtttatc cttccaattt agttcattac ttcctgcacc | 240 |
| tttgatgtca tatacataaa caggaaataa cacatggtgg ctgggatgta gagagagcca | 300 |
| caggacttgt gaatgaaatc cacaggcaag gatgtggcga ttccttttgc aatattggag | 360 |
| ggaatgccaa acccctatgtt tgctgtggaa aagagtatgg tagttcctca aaacatcaaa | 420 |
| atggtattgc cttatgattc agcacccaca tcccaagaca gcaaaagaat tgaaagcaga | 480 |
| gtcttgaaaa aatatttgca catccatgtt tgcagcagca ttattggcaa tagctaaacg | 540 |
| tagaagcaat tgaactgtcc acacagatga agggtgagca acatgatat atcntacatg | 600 |
| gaaattatca gc | 612 |

<210> SEQ ID NO 48
<211> LENGTH: 515
<212> TYPE: DNA
<213> ORGANISM: human
<220> FEATURE:
<221> NAME/KEY: misc_feature
<222> LOCATION: (512)..(512)
<223> OTHER INFORMATION: n is a, c, g, or t

<400> SEQUENCE: 48

```
ggaaataatt tatattttga ttgaagcatg gtgagaactt ttatagaaaa tcctattttt      60 aaaaatttt ctttccttta tcacagatta caatggctaa tctacatgaa tgactatttt     120
tcttctattg acaactcctt ctgcaaaatt attttattt atttcttga gttatagatt      180 tagggggtac aaatgcagct tgttacatg acatattgt gcatggcgaa gtctggagaa      240
atcttccgca tacacctatt cagaaacact agatttcacc taatttaaat caccattctc    300
taacaggtca agaatttaaa taaaaactga ttacaaccaa catcatcatt ctaactttta    360
aacaaaagca tgtaagaaat tgcattaaat ataagtagaa aagtggtcaa ttcaagataa    420
aattcaagaa tgttttgaa accatgtatt tacaaaaaaa ttctaaaata cgccacaaag     480
atactcctcg agaagagcag ctagatccta cngac                              515

<210> SEQ ID NO 49
<211> LENGTH: 324
<212> TYPE: DNA
<213> ORGANISM: human
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t

<400> SEQUENCE: 49
tctcagccag gaacagggaa gataatctca gnttgcctat gtcttattca tcttttctgg    60
tgggtctagc cctctctctc ctcgccagtc ccagatcatt ctttgtcttt gtggtagctg    120
gaaatacagc tcagatccca cattaaaaaa atatatatat tatactttga gttctgggat    180
acatgtgcat gagttctggg atacatgtgc agaatgtgca ggtttgttac acaggtacat    240
acatgccata gtggnttgct gcacccatca acccgtcatc tacattaggn attctctccta  300 atgctatccc gcccctagcc cccc                                           324

<210> SEQ ID NO 50
<211> LENGTH: 471
<212> TYPE: DNA
<213> ORGANISM: human

<400> SEQUENCE: 50
gccaaatttt tacaattcat aagagcaaat aatataaagg tttatctgtc taatatctat    60
gttttatata ataactaaac caatgttgca tcccagatgt ctctcaaagt tttctttctc    120
cacttcttcc attggaaaaa tttataattt gagtaaattt catttctatg tctatttgga    180
ggtaataata ataataaaac agccctttgt gaattatat aaatggaaat aacagaaact    240
ccagtttgga ataacatgat ttatgtgtgc aattctttaa tatcctgtca atttgaatag    300
tgatgttttt atattcacag tcagttgaag atgccaataa cagcggcatg aatctattgg    360
accagtctgt cattaaaaaa ggtatggata attccccca aaaagtaagc aaagttctct    420
catgcattaa cgtctttatg atgaatttca ctttggggga ttcattattg a             471

<210> SEQ ID NO 51
<211> LENGTH: 594
<212> TYPE: DNA
<213> ORGANISM: human
<220> FEATURE:
```

<221> NAME/KEY: misc_feature
<222> LOCATION: (540)..(540)
<223> OTHER INFORMATION: n is a, c, g, or t

<400> SEQUENCE: 51

| | | | | | |
|---|---|---|---|---|---|
| cgaatttaat | acgacccact | atagggaatt | tggccctcgt | gccgggcctg | ggacgcacca | 60 |
| acaagttgta | tatgtttcaa | agtctattac | aagttggaac | actcataagt | ttaggaggcc | 120 |
| aggtgccgtg | gcttatgcct | ataattccac | gtacttggga | ggagtgcctg | aggctaggaa | 180 |
| tctgggacca | acctgggcga | catagggaga | cttcatgtct | aaaataaata | aataaataaa | 240 |
| ttattagctg | ggcatagtgg | tgcccaattg | tagtcccagt | actcagaagt | gtgagtcagg | 300 |
| aagatcgttt | gaatccagga | gttcgacacc | aacctgggta | acataatgag | acccctctca | 360 |
| tctcaaaaaa | ctaacaaatt | aagaaaaata | gactggtttc | tgcaagggt | aaaaacaata | 420 |
| agaaaaaata | aatttaaaaa | ccctgagtgg | acatttttt | caaagaagac | atacaaatgg | 480 |
| ccggaaagca | aatgaaaagg | gacttaatat | cactaatcat | tagagaaatt | caaatcaaan | 540 |
| cccaattaca | tgttacctca | tacatgcaag | gatgggtact | atcaagagag | atta | 594 |

<210> SEQ ID NO 52
<211> LENGTH: 515
<212> TYPE: DNA
<213> ORGANISM: human

<400> SEQUENCE: 52

| | | | | | |
|---|---|---|---|---|---|
| gccatacttc | ccaaggtaat | ttatagattc | aataccatac | cccctggcac | ccaccttcat | 60 |
| cagaaagagt | agaaagaatg | aaccaaaccc | taaaaagcca | tctaaccaaa | ttagttttaa | 120 |
| aaactcgatt | atcatggacc | aagtgccttc | ctattgcctt | attaaaggtc | cgaactgtcc | 180 |
| ctcagaaaga | agttggctta | tctccttgtg | aaatgctgta | taggctgcct | tactcacact | 240 |
| tcactgttga | cattcctacg | tttgaaacta | aaagtcagtt | tctcaagagc | tatgtacttg | 300 |
| gtctctcttc | cactttctct | tccctcaaag | ctaaaggctt | tttagtacag | atgccaccct | 360 |
| tggagttccc | agcacatcag | catcagcctg | gggatgatgg | tctcatcaga | agctggaaag | 420 |
| aaggaaactc | aaaccagctt | gggaaggacc | ctatctcgtg | cttctaccac | agactgcagt | 480 |
| ccaacaacaa | caaaaaatgc | agaccctcat | accca | | | 515 |

<210> SEQ ID NO 53
<211> LENGTH: 383
<212> TYPE: DNA
<213> ORGANISM: human

<400> SEQUENCE: 53

| | | | | | |
|---|---|---|---|---|---|
| gcaacgagtc | tgcgaggccg | aatggaagcc | agctggctgc | aggggagaga | gcaagagagt | 60 |
| ctggcagaag | gtgcacctgg | agaaggaagt | agaggccagg | ccagcatatg | cttacaaaat | 120 |
| ttgaagacca | caaccactct | ccaaatacaa | atgcagcaag | tgatttgaag | atcatagaaa | 180 |
| tgataataca | ggcaaaaaat | gcaagaaatc | tcccctgcca | aattattcaa | ctatgtatga | 240 |
| cttctgcctt | tcacagcgc | caatttgcca | tgctatgcgt | tcatctttg | catcattttc | 300 |
| aatactggat | gtataaattg | tgaaagactt | tcagagttct | aattcttta | tgcatttttt | 360 |
| gcaatttgat | ccatgaagtg | cat | | | | 383 |

<210> SEQ ID NO 54
<211> LENGTH: 389
<212> TYPE: DNA
<213> ORGANISM: human
<220> FEATURE:

```
<221> NAME/KEY: misc_feature
<222> LOCATION: (244)..(244)
<223> OTHER INFORMATION: n is a, c, g, or t
<220> FEATURE:
<221> NAME/KEY: misc_feature
<222> LOCATION: (340)..(340)
<223> OTHER INFORMATION: n is a, c, g, or t

<400> SEQUENCE: 54
cagctgtgag agcaaactgc tgcagcagtg ctgacaggaa cgggaaggag catgcccctt    60
cttcctgcag catggaagct tccctctact ggaaaaatcc aacaggatgc cagctgcgaa   120
gcagagatgt ttgcagagtt ctgtcgctgg tatcacaaaa gcagagctaa aaagagcggg   180
tgtggaactg agagcgagc ttcctaactg gcacagcccc tgttagccac tcagcatctg    240
cacncagcct tctacacctt tgaacttctg tcccaccaca aaagcaattc tttgtgccca   300
aggagatgta attaattggg agctgttacc ctctctcaan gatgaggaca tgtaaagctc   360
accagtcact gtcaatctct gagctgggg                                     389

<210> SEQ ID NO 55
<211> LENGTH: 506
<212> TYPE: DNA
<213> ORGANISM: human

<400> SEQUENCE: 55
caaaattata tctcccttct actactgcag ctggcaagct cttgaaagca tcacttcctc    60
gctagaggcc aatgaactca agccactaca gcaactcaga acaactctgc cccagagaag   120
gagaatacaa caggtaattc taccacctgc acaccctagc taactagagg tcctgagtct   180
atccttgtga caacttcact gctaacataa ccagcattca agaaaaccag tgcactaaat   240
tacaaccaag gactcccaca gagtccactt tactcccctg ccacctccaa tggagcaggt   300
gctggtatcc atggctggga gacctgaagg tggatcacat cacagtactc tttgcagaca   360
ttccccattg ccagcctgga gtctggtagc cctgaagggt ggctagaccc agaagggcag   420
taacaatcac tgcagtctgg ctctcaggaa gccccattcc tagaggaagg gggagagaac   480
ccatcaaggg atcaccccat gggaca                                        506

<210> SEQ ID NO 56
<211> LENGTH: 462
<212> TYPE: DNA
<213> ORGANISM: human
<220> FEATURE:
<221> NAME/KEY: misc_feature
<222> LOCATION: (455)..(455)
<223> OTHER INFORMATION: n is a, c, g, or t

<400> SEQUENCE: 56
atcatctgtg ggaaggaggg gagcatctag ttgtctactg ctagtgagct aggagttcta    60
ggattgtcag gttctaggat tgttaggttg ggcttagcct gctagatttt attctgtctg   120
tattccggca ttgttacccc tttctggcta atcatccagc accatttccc tccatttgag   180
gatttatagt cataattggg ctgggggatg ggggactccc ttttatcag gtgatgctgc    240 ccttgaagcc tccaatagct tattagtttc aagattctca gaattcttag gcctctcaaa   300
ttaaattttc cagtactaca taaaacattt ctatacactg cggggtgaa aaactaccac    360 tctctatacc taactgaacc tgctatggc caagcacagt ggctcatgcc tgtattgcca    420
cactttggca ttcagccttg ggagctgaag gggangatag ct                      462

<210> SEQ ID NO 57
```

<211> LENGTH: 567
<212> TYPE: DNA
<213> ORGANISM: human
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (550)..(550)
<223> OTHER INFORMATION: n is a, c, g, or t

<400> SEQUENCE: 57

| | | | | | |
|---|---|---|---|---|---|
| gcggatatat | agtgttactg | ccaagagaat | ttaagaatat | ccaattttga | atgtgttaat | 60 |
| cattaactat | tcaagttctt | atgggtagaa | tcaccattgt | ttatcctaag | agaattgcca | 120 |
| ggtattacat | atcatatttg | cagtcaaaaa | cctgagagcc | tgcttgtggt | taaagggaca | 180 |
| tggatggagc | cggaggccat | tatccttagc | aagctaccac | aggaacagaa | aaaccaaata | 240 |
| ccacatgttc | tcccttataa | gtgagagcta | aatgatgaga | acacatggac | acacagaggg | 300 |
| gaacaacaca | cactggggcc | gtttagaggc | tgcagggtgg | gaggagggag | agaggatcag | 360 |
| gaaaaataac | tgataagtac | taggcttaat | acctgggtga | tgaaataatc | tgtacaacaa | 420 |
| accctcatga | cacaagttta | cctatgtaac | aaacctgcac | ttgtaccctg | nacttaaagt | 480 |
| aaaaantaga | acaaacagtc | agaaccatgc | accatttggg | atcgataaca | cataaaggca | 540 |
| gcattcatgn | tatttagtga | gtcgctt | | | | 567 |

<210> SEQ ID NO 58
<211> LENGTH: 465
<212> TYPE: DNA
<213> ORGANISM: human

<400> SEQUENCE: 58

| | | | | | |
|---|---|---|---|---|---|
| taatcccagc | tacttggaag | gctgaggtgg | gaggatcact | tgagcctggg | aggtcaagac | 60 |
| ttcagtgagc | tgtggttgtg | ccactgcatt | ccagcctggg | caacatagcg | agacactgtc | 120 |
| ttaaaacata | acataacag | aaaagtaaaa | agatcatttt | acacagataa | agtggcacaa | 180 |
| gttttgtagt | attatattaa | acctcatatt | tgaggtgttt | tcaaaatctt | atccatgcca | 240 |
| attttctaat | gcttttccta | aagaagaact | atattataga | tttgtggact | aatttcaaat | 300 |
| tgaaaatgca | gcttttccca | caggaacagg | caagaaaaat | acaagaatt | aacaatccgt | 360 |
| atgtttatt | tgtagttaaa | aaataatgat | gatgttttgt | ttgtttcatc | ttggcctaag | 420 |
| gagttacagt | aaattaaaag | tacagaattc | tttttcattc | tattg | | 465 |

<210> SEQ ID NO 59
<211> LENGTH: 366
<212> TYPE: DNA
<213> ORGANISM: human

<400> SEQUENCE: 59

| | | | | | |
|---|---|---|---|---|---|
| gattctagaa | gcctgtaatc | tttcgaattt | gcccagtcaa | ccaagcctgg | ggtttaaatg | 60 |
| aattttcaac | acctttctgc | tgacagtcac | acatgttaaa | ccttgatttg | cttaaaagta | 120 |
| ttattaagga | tgagaatgta | atactgccag | tggtatgtgg | tgatattatt | gtggcgctgg | 180 |
| ggggatgaaa | ctaacgtctt | tcagtaaatg | tttaatttta | cacaccatat | aatcagttgt | 240 |
| attattgcaa | gtgcacagca | ggtatgtaga | aaaatagaat | gcatatattt | aacatattag | 300 |

```
aaataacttt attaatattc ctatttcatg ttctcatgaa attttaatca tttgcatttt    360
ttagct                                                                366

<210> SEQ ID NO 60
<211> LENGTH: 425
<212> TYPE: DNA
<213> ORGANISM: human

<400> SEQUENCE: 60
gctgtcctga ttagaattaa ttttcataaa gagaacaaga atcttgactg gttcacccct     60
caattccttg tgcccgcaac agtgaccggc acatggaaag cattcaggga ataaaagcac    120
aatggaaaat taaaacatac tcactgcatg cctgccacct atagaaccaa attaaatcac    180
tgccaatatg catggggaaa accttcccat ttttctggaa taatgttaca aaggatggaa    240
aataagtgca catcacctgg atggcattta ataaacgctg tgacccagta gtgtacattt    300
cagtgaatat tgccaaagga agtaggccaa catcaggtaa tctgagttaa ctttcctgta    360
cattgtgtat tcgtttcctg atgatcaaaa ctggataatt agtctacaat gtatctttcc    420
tggta                                                                425

<210> SEQ ID NO 61
<211> LENGTH: 591
<212> TYPE: DNA
<213> ORGANISM: human
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t

<400> SEQUENCE: 61
gagatctcca aggattttca tattgccaag cagtcacata atataaacta aatgagttcc     60
caaatgagtt gtgtcaagtg tccatgttgt tttttagagt caagatatat ttagtttaaa    120
tgtgaaaaga aatttcaagt agtctttctg tttcagtcaa cagtctgtga aatgccaaat    180
actcactatt gttacattgg cttcttagga aaactgcccc taggtactat ggcttgtgtt    240
gattttcagt gaagccagcc ttgtttatcc tggtctacaa atgtttggac actataaaga    300
ctagacatga aggaggctga cctcctgtca gctagagtgg cataaaattc aagccaattt    360
tggcactcca ttttgaatgg tgattttttgg atctaataac attctctctg tcttggaaag    420
taagacgcat tgtgaattaa gagaattcag gtcattagag tttaggcatg attccagttt    480
tccataagnc tgctccctat tgcttcccat cttggaagtg cttaaaaaac tctatactga    540
aagaaacatc cggggctact tacatccact gtgtcntgcc aaacctcctt g             591

<210> SEQ ID NO 62
<211> LENGTH: 525
<212> TYPE: DNA
<213> ORGANISM: human
<220> FEATURE:
<221> NAME/KEY: misc_feature
<222> LOCATION: (478)..(478)
<223> OTHER INFORMATION: n is a, c, g, or t

<400> SEQUENCE: 62
cttgggtcaa gagacgccct tgtgaagcca ctccactaga gccttcagtc tgacatacag     60
atatggggag tcttggcaga gcagctgctc cggcacaggc aaagacccag gaactccaaa    120
```

```
cttcccagca aaagtaactg caactccagc aaagcaggat gttagacccc cgtacatacc    180
cttaggaaaa aaggctgaat caagaggacc aagtagagac agtctgcagg tctcactttc    240
ataacacctc acaggataag acccactggc ttggaattcc agccagccac cagtagcagt    300
tttgagccta cctgggatgg aactcccagg ggaagggaca ggctgccatc tttgctgttt    360
gggtgactca gctgttctgc aggctttgga gagtacaaac caaccagagg cagagaggat    420
tccccagcat agcatgactt ctttaccaaa tgtggtcaga ctgctggtta agcaggtncc    480
aatccattcc tcatcacaga gcaggacctc acaactggga ctcca                   525

<210> SEQ ID NO 63
<211> LENGTH: 388
<212> TYPE: DNA
<213> ORGANISM: human

<400> SEQUENCE: 63
gtgaatgtct ggtccaccgc tccccggctt ctttccccgc ttttgctttt cccttccccc     60
gctcccgccc tcccgcctca cgacccgacc accgcccagc tgagccccg cggctccact    120 gcgcagaagg tgcactggag gccctgcccg ttgcccgccc cgcggggtgc cgagaagtca    180
acctgaataa acgccttgta aaagaacttc ctaatggaa aaaatatctt atgatttcca    240
ttctcaacgc tcttcagagg actaaaagat aaaggccatg atggattcat tcaacaagtc    300
ctaatcctgc gccctggtgt gtgccagacc ctgctccccg cgaggggatc cacgagcgac    360
cctcaccagg gcctgtcatg gggtgggg                                       388

<210> SEQ ID NO 64
<211> LENGTH: 344
<212> TYPE: DNA
<213> ORGANISM: human

<400> SEQUENCE: 64
gcttggagag gctcttcctg ggtgtgtcta gttggccctc ttttccctcc tcttcttagg     60
atacttttta tttctttgct atcagttgta acgtttcctc tttcatttct gattttgtt    120 attcgaatct tctttctttt tcttagtct ggttaagaat ttgctgaatt tacctttaaa    180
aaaccgaact ttccattgtg aagacattg tggcgattcc tcaaggatct agaactagaa    240
ataccatttg acccagcaat cccattactg ggtatatagc aaaaggatta taaatcatgc    300
tgctataaag acacatgcac acacgtatgt ctattgtgaa aaag                    344

<210> SEQ ID NO 65
<211> LENGTH: 459
<212> TYPE: DNA
<213> ORGANISM: human
<220> FEATURE:
<221> NAME/KEY: misc_feature
<222> LOCATION: (446)..(446)
<223> OTHER INFORMATION: n is a, c, g, or t

<400> SEQUENCE: 65
gcttatatta taaatactat ataatattga aattataagt ataatataaa tatagcttta     60
agtaaatcat tacaaaaatg tcagttaaca atggaagact gtgagagaga ggattaaaac    120
aagagcaaaa cagaaaacta ttaacaaaat ggcagttagt aagtcctcag caatcagtaa    180
ttattttaat gtaaatggct taatatccca ataagaatg cttaaagtag ctgagtgaat    240
caagtcactg gatcttgttt tcttcataat tcagtcttga cgtattgtta tattagttca    300
ttttcacagt gctataaaga aatacccaag actaggtaat ttataaagga aagaagttta    360
```

| | |
|---|---|
| attgactcac agttccatat ggctgtgctg ggggaggtca agtacttaca atcatggcag | 420 |
| aaagcaacgg agaagtaagt acttcntcca aggcagcgg | 459 |

<210> SEQ ID NO 66
<211> LENGTH: 450
<212> TYPE: DNA
<213> ORGANISM: human
<220> FEATURE:
<221> NAME/KEY: misc_feature
<222> LOCATION: (5)..(5)
<223> OTHER INFORMATION: n is a, c, g, or t

<400> SEQUENCE: 66

| | |
|---|---|
| tttantttag tctagattct gagaacttga agaatgcata tttgaaatga caaatattgc | 60 |
| catgttgccc tacaaaggac catagttatt gactcaccca ctgttagtgt atgggggcac | 120 |
| ctgtctttcc acactctctg ccatgctggg taatgccaat ttttttaaag tttttgcgag | 180 |
| atatttggaa cagtgttacc taactaatac agtaagcact atgcatgtat ggctatataa | 240 |
| gttgattaga atgaaataaa ataaaaaaat tcagctcccc agccatacca gtcaaattcc | 300 |
| aaatgtttga taactgcaca ttgccctaga ggcgatcata ttaacaatga tcatacagag | 360 |
| catttctgcc atcacagaaa gttctgccag acagtgctgc tcttgcacaa aaaatgaaat | 420 |
| ctcattggtg tttcatgcct gttcccgata | 450 |

<210> SEQ ID NO 67
<211> LENGTH: 545
<212> TYPE: DNA
<213> ORGANISM: human
<220> FEATURE:
<221> NAME/KEY: misc_feature
<222> LOCATION: (519)..(519)
<223> OTHER INFORMATION: n is a, c, g, or t

<400> SEQUENCE: 67

| | |
|---|---|
| gttttcataa atctaactaa ctcctatttg aaagagatga ctgcatttat gcttggtggt | 60 |
| cttcatgtta caatgaacat gtctttagtt tcttatgatt tgtatatgcc acttgtttac | 120 |
| aagatagcct agggttttcc atctattttt ttatccagag gacctcagct tacatctctc | 180 |
| tattaacatc tatgcctaat gagagaaggt tgcttccctg tgacttatac aaaatcagtg | 240 |
| accagctgtg gcattaatgg aagaggggcc agaatgcatc tcggtaatat atcagtgttc | 300 |
| tttttcttgt aacttagttt ttaaatttct cgcccatgta tacctttcga ggatctccaa | 360 |
| aagcccatgt atatactcct tccaagtttc tctcactggc catagaccat taacgcatca | 420 |
| agaatggaaa atgaaggtag ccataggcca aaaatacctc ctccctgagt gctctgcatt | 480 |
| ctgatccagg gatagcaatg atctcaatca agcaaatnc tcgcaacttc tctagatctc | 540 |
| cctcc | 545 |

<210> SEQ ID NO 68
<211> LENGTH: 501
<212> TYPE: DNA
<213> ORGANISM: human
<220> FEATURE:
<221> NAME/KEY: misc_feature
<222> LOCATION: (467)..(467)
<223> OTHER INFORMATION: n is a, c, g, or t

<400> SEQUENCE: 68

| | |
|---|---|
| ggtgccacta agaacccat tcccaaaaag tcatggataa agaaaagaa actgagcttt | 60 |
| taagtgtctc aaaagaggtc ggctggaaaa taagttcaga agaaaataca ttaccacaaa | 120 |

```
catgaacaat atagcaaaca tgagagcaaa ttacacttag acatttcctt tatcagaatt      180
tcctttaaat tcattccatg gccacggcct ttcttaggct aactacagta gacatagctc      240
ttctattatg atatctcctc tgcactttct agtatacttt acatcacaac atgagttttc      300
tttttcaagc aaggtttagt tattgttccc ttctgtagct gtgccttccc aaagctacca      360
gttgtcctca atcaaatta aaacatctaa acataggatt caaggctcca taaattcctg       420
ggcccaaacc actccagctt tatcatccta cagtcaatgc acactgnctc acattttcta      480
tctatttact ttcatttcta c                                                501

<210> SEQ ID NO 69
<211> LENGTH: 514
<212> TYPE: DNA
<213> ORGANISM: human
<220> FEATURE:
<221> NAME/KEY: misc_feature
<222> LOCATION: (452)..(452)
<223> OTHER INFORMATION: n is a, c, g, or t

<400> SEQUENCE: 69
gaatgcatca gtgtctccat aacagaattt atcaagcaga agaataaatt agtgagtttg       60
aaaacatgaa aatatagagg agaaaaagaa agaagaataa aaaggatgaa gtatgcctac      120
aagatctaaa aaataacttc aaaaggacaa atctataact tattggcctt gaagaagatg      180 taagaaaga gatcaggata taaagtttgt tcaaagaaat aataacagag aacttgccta       240
gcatagagaa agataagaat atccaggtac aagacagcca aaatcactaa cagattctat      300
ctaaataaga cttcttcatg gcatataata atcactctta aaggccaagg acaaagaaaa      360
gattctaaaa gcagcaagac aaaagaagca aataacatat aaagaagctc cgtatgtctg      420
gcagcacatt tctcagtgga accctcacat gncatgaggg aggggatga catatccaga       480 gtgctaaggc aaaaaaagct tccacttaaa tatt                                  514

<210> SEQ ID NO 70
<211> LENGTH: 445
<212> TYPE: DNA
<213> ORGANISM: human

<400> SEQUENCE: 70
ccatatactg aggacttaca aatgtatata ctcagcgcag acctctcctc tgaattctag       60
actcatatat ccgaatgtct tcttgacaaa ttcttttcaa tgtctagtaa ttcaaactta      120
gctaatatgt ccaaaacctg agctttaacc cccaacaaga tcctccagtt tttctcattt      180
cagtaaataa ttccattctt cccttacagt tattgagccc aaaaaccttg gagctattct      240
tgactcccta actctctctc ctccccccagg ccagtatgcg agcaaatcct gttggcttta      300
aaatgtagcc aaaatcagcc aggagcggtg gctcacccct gtaatcccag cactttgaga      360
tgcagaggcg ggcggatcat ttgaggccag gagttcgaga ccaacctggc caacatggcg      420
aaacgctgtc tctactaaaa aaaaa                                            445

<210> SEQ ID NO 71
<211> LENGTH: 321
<212> TYPE: DNA
<213> ORGANISM: human
<220> FEATURE:
<221> NAME/KEY: misc_feature
<222> LOCATION: (312)..(312)
<223> OTHER INFORMATION: n is a, c, g, or t

<400> SEQUENCE: 71
```

```
gtgttgatgt tccaccagaa acaccttaag tgtatactgt tgtgtaatgt ctctagaaag      60
gaatcctgtc ttaaaactgg ttttgctgt ttttgaagt ttctacctaa aatcattttt      120
ggtatatcct gataatctct ataatactag aattgtctgc aaaatatagt aagaagaatt    180
ggagcctaat agctgattcc tcccaattta tctgttatgt tttgtcacta ttcacatttt    240
agtcttttct acgataaaaa ttgtatgtgt actttcatgc cagtatagga aacctcaatc    300
tttttttttt tncccctta a                                                321

<210> SEQ ID NO 72
<211> LENGTH: 527
<212> TYPE: DNA
<213> ORGANISM: human

<400> SEQUENCE: 72
gttaaactaa agaaaccata tacaaatttc aagtcaggtg cttttactca ttttataccT    60
tgattcttga atggccagat tttctgaaaa tacccagtta atgattagat tatgctactt    120
cagtcaccac gtgtttgaag gctgatcaca gaaaactaga agcaatgtaa ctagtttcaa    180
aatataatta aatggaggag gaagtgtttg ctttttttcc ctccagacca caaattggta    240
ggtaaagtaa aagttagatt tgaaaattgg gcctgggtgt ggtggcttac acctctcagc    300
acgttgggag gccaaggtga gtggatcgt tgagtcccag agtttaagac cagcctgggc    360
aacatggcaa aatgccattt ttactaaaaa tacaaaaatg tagctgaatg tggtggcgca    420
tgcctgtagt cctagctacc caggaggctg aggtgggagg atcatctaac ccaggaagtt    480
gaggctgcag tgagcatgat aatgccctgt atgcatcctg ggcaatg                  527

<210> SEQ ID NO 73
<211> LENGTH: 363
<212> TYPE: DNA
<213> ORGANISM: human
<220> FEATURE:
<221> NAME/KEY: misc_feature
<222> LOCATION: (362)..(362)
<223> OTHER INFORMATION: n is a, c, g, or t

<400> SEQUENCE: 73
ggcagtcagt catctgttct gggagacaaa ccagtccagg acaagtagcg tttggacaat    60
atgccaaatc ctgtcacatc acattgttgc tctaaaatgg gtggatggat tgggttgatg    120
gcatacgcta agctccatga gggcagggat tgtggctgga ctaagtctag tggcaattaa    180
atagagctca aattaaatag agcttttgct ttgaggtctg aatccatctc catgatttgt    240
cactagacta gtgacaaaca gtggctggat agcatatgtt gtttagacag cttttgcttg    300
ttctaaagtt tgaatgtgaa ttggggtttg caactcaaaa ttgggggttaa tatttgcacc    360 tna                                                                   363

<210> SEQ ID NO 74
<211> LENGTH: 509
<212> TYPE: DNA
<213> ORGANISM: human
<220> FEATURE:
<221> NAME/KEY: misc_feature
<222> LOCATION: (496)..(496)
<223> OTHER INFORMATION: n is a, c, g, or t

<400> SEQUENCE: 74
ctcgtgccgc acttaatcat caaaaccatt atattaggga catatgattg ttatcattac    60
cttagtttta tagatgacat gacttaggta cataacaatg ttcttataaa ggtattaagt    120
```

```
ggaatagaag gcagtcagta ctcagagttt agtgtgcacc actactcact tgctattcat      180
ttattcattt cattattaca atatgagaag gaatgaggtt cagaaaagaa acataagttc      240
tgttattagg agattatcaa ggttaagctt tcctaagact ttaacaggtg aggtgaaaaa      300 tatattttc ctgaggaaat aagtttgttt taaatcataa gcacatttac gtaggcttcc       360
attcacctgt tttcctcctt gccttcatat aaagatactc atacaaattt attcgttttt      420
tgtgattatg aaaacccagt caatgtagat cctttatgtg ctttcttaat acaagccaca     480 tgcattttc tgctgngcca tattagcat                                         509
```

```
<210> SEQ ID NO 75
<211> LENGTH: 306
<212> TYPE: DNA
<213> ORGANISM: human

<400> SEQUENCE: 75
```

```
catatctatt gttgtatcct cccacccatt ttccatagag gagctagagt cgactggtcc       60
taaaatgcaa atctaggctc ttcactcccc tgcgtaatcc cccttgcatt tacaaagatc      120
ccagtccttc cctctgatgt cctctctgac ttggcctcct ggcctctctg gcttcacggc      180
atcccactcg cccttactag gcacgctttt cataaatgcg ccagcctcgc tctcccttct     240
ggtcttaggc ccttctccca cctccatcca cacactcaga cataaaaaaa tcctcagcca     300
aaaaaa                                                                306
```

```
<210> SEQ ID NO 76
<211> LENGTH: 587
<212> TYPE: DNA
<213> ORGANISM: human
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t

<400> SEQUENCE: 76
```

```
canggggtggc ngccaaatcc agtttacagt agctatagat ttcactgcct caaacgggga     60
ccccaggaac agctgttcct tgcactacat ccacccttac caacccaatg agtatctgaa     120
agctttggta gctgtggggg agatttgcca agactatgac agtgacaaaa tgttccctgc     180
ctttgggttt ggcgccagga tacctccaga gtacacggtc tctcatgact ttgcaatcaa     240
ctttaatgaa gacaacccag aatgtgcagg aattcaagga gttgtggaag cctatcagag     300
ctgtcttcct aagctccaac tctacggtcc caccaacatt gccccatca tccagaaggt      360 tgccaagtca gcgtcagagg aaactaacac caaggaggca tcgcaatact tcatcctgct     420
gatcctgaca gatggtgtta tcacagacat ggccgacacc cgggaggcat tgtccatgcc     480
tccccctccc atgtcagtca tcatcgtggn agtaggnacg ctgactcatg aatgcaatgc     540
```

```
tgacgtgatg atggatctga gtnccaggag gctgtctcaa aatgtca          587
```

<210> SEQ ID NO 77
<211> LENGTH: 520
<212> TYPE: DNA
<213> ORGANISM: human

<400> SEQUENCE: 77

```
aagaatttgg tatacatatg aaaaataacg ttgattctta cctcatacag aaaaattaat    60
tcaaaatgga tcactatgtt aaattcaaaa atgaaaatta ttgagcttct agaagaaagc   120
ataggataaa atccttgttg tcttgggagg caaagatttc ttaggacaca aaacccacta   180
actgtaaaaa aattataaat tgtattttat caaaagtatt ctcttttgtt tttgaaaaat   240
gccattaaga aaaaggaga ttgtgagttg tgggacagtt ggaacttacc tacctggctg    300
tccacggctt aaaatgatat agccacttga caatttctta caactcagga attctactac   360
tccctggtac aaagtaagga actactgcta gctgcaacaa aatggatgaa tctcacagaa   420
atatggtgag caaagaattg gacacaaaag gatatacgga tcattcattc tatggggtcc   480
agataagcag aatgccctta tgatgatgag gggactggga                         520
```

<210> SEQ ID NO 78
<211> LENGTH: 500
<212> TYPE: DNA
<213> ORGANISM: human
<220> FEATURE:
<221> NAME/KEY: misc_feature
<222> LOCATION: (449)..(449)
<223> OTHER INFORMATION: n is a, c, g, or t

<400> SEQUENCE: 78

```
gggaaacaag gatttgaaat cttgggacta gagttataga gatttattaa tgtagtgtag    60
catgtttggg aaaaaaatgg agttggaggt cagaggtctg tttgcattga atcctggctt   120
aactaaaaat acattaggtg tgtccagttt acaaaatagc ttagaaatga gatcttttaa   180
gaaactctat acaccatgga ataatataca gccatagaaa agaatgagat catgtccttt   240
gcagggacat ggctggagct ggaggccgtt atccttagca acctagtgta ggagcagaaa   300
accaaatgct gcctgttctc ccttatgggt gggagctgaa tgatgagaac acatggacac   360
atagaaggga acagcacaca ctgccgcttg tggaagggtg gaggatggga agaggggagaa   420
gatcaggaag aataatggat acttattcnt cctgaatcac ccgggggatg aaataatata   480
tacaacaaac ccgcatgaca                                               500
```

<210> SEQ ID NO 79
<211> LENGTH: 449
<212> TYPE: DNA
<213> ORGANISM: human
<220> FEATURE:
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t

<400> SEQUENCE: 79

```
tggaagtcca gtgtcttaaa tcattcatga aggagtccat ttcctgcact gtggtgcaat    60
gtcgccttgc ngancnancc ccttccccac aggtggggtg attttatggg ctgtcttttc   120
tgttcctgta gtctgtgtat ccctgcactc ttgccagatt atgttaatga ctattgcttt   180
gtagtcagtg ttgaggtccc taaaacaggg gccctccacc cctgggcctc ccgggcctcc   240
cgtggcctgg aatgggggct ccacagcagg aggtggggat tacagcctga gccccgcctc   300
ccgtcagacc agcggcagta ttagattctc ataggggtgc aaaccctatt gtgaactgca   360
catggaaagg atctaggttg catgctccaa tgagaatcta atgtccctg cccacagccc   420
gtgaaaaatt gtcttccaca aatcaatcc                                    449
```

<210> SEQ ID NO 80
<211> LENGTH: 505
<212> TYPE: DNA
<213> ORGANISM: human

<400> SEQUENCE: 80

```
ggcccagaaa agtctataat gggtagattc aattgacagt ctggagactt gattttatgt    60
cctggctcct tccccagatt gtacaccata atctctctct gtctcaaatt ccccatcctt   120
caaacatgtc caacaacccg ctatgtaacc ccaactttaa ctgcattgct tatgagtttg   180
aatgaaataa caatatgagt aaaggacaca ggaaaaaaaa tcaactgtct atgccaatat   240
caggcttgta aagggtatgg tcactttcta tcaagaaacc ttggtagttg agtgaaccac   300
atttttcttt agtgtgcctt tagtgaaaaa tgactaattg aatagaattg ctagcaccag   360
aacttcagct ttcaaaatac taagctatcg ctgtgaagga gacagtcctg aaatctgtga   420
ccttggatca ggcacaacaa cctatctgct ctcaggcaca aaagcagact tgcaagcaaa   480
tattcctgga gtcatttcct gatga                                        505
```

<210> SEQ ID NO 81
<211> LENGTH: 547
<212> TYPE: DNA
<213> ORGANISM: human
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (473)..(473)
<223> OTHER INFORMATION: n is a, c, g, or t

<400> SEQUENCE: 81

```
gagactcagc ctactgtttc tagggtctga catgatcacc agtcccactc ccaccaaaga    60
gcagcccaag tccactgcca gcgggagctc tggtgaaagc atggactctg tcagcgtgtc   120
atcctgcgag tcgaaccact cagaggctga ggagggctac attactccca tggacacccc   180
tgatgagcct caaaaaaagc tctctgagtc ctcctcatac tgttcttcta tccattccat   240
ggacacaaat tcctcaggga tgtcttcctt aatcaacccc ctctcctccc ctccgtcctg   300
caacaacaac cccaaaatcc acaagcgctc tgtctcggtg acgtccatta ccttgactgt   360
gctgcctcct gtttacaacc aacagaatga agacacctgc ataatccgca tcagtgtgga   420
agacaataac ggcaacatgt acaagagcat catgntgacg agccaggata aanccccgct   480
gtgatcagag agccatgctg aagcacaatc tggactcaga cccgccgagg agtacgagct   540
ggtgcag                                                            547
```

<210> SEQ ID NO 82
<211> LENGTH: 486
<212> TYPE: DNA
<213> ORGANISM: human

<400> SEQUENCE: 82
gagaactgaa tgggtgtatt ctttgatacc tagttaacca gttggtgctt aacaggagaa    60
tttttcattg gagaattgct accaggtaac attttggtga gtgaaaagga ggcccttttgg   120 tacaggtatt tgactagaga cattgcttct acaatttctt agtcattgtg aaaaatcaca   180
tatttaaatg ggattattta aattttaaa tactgtatag tatttgtagg caggtatagt    240
ttttatcttt atttggtgtt ttatatgcag ttatttaagt tctgaaaatg accatataat   300
ttgaagacaa cttatttgac ggaatgtttg aaatgaagtt tgttgagggg cttttgtttg   360
atttagcgaa tgggatacag tgttgaatga tgtcctaagt ggtaacagcc attttcctta   420
aggaaacttg ctgtgagctc ttaaaagcat gtatcctact gtttcaaagg ttcttggttt   480
aacctc                                                             486

<210> SEQ ID NO 83
<211> LENGTH: 310
<212> TYPE: DNA
<213> ORGANISM: human
<220> FEATURE:
<221> NAME/KEY: misc_feature
<222> LOCATION: (292)..(292)
<223> OTHER INFORMATION: n is a, c, g, or t

<400> SEQUENCE: 83
gagagagcta gctgatcttc aacaaacctg acaaaaacaa gcaatgggga aatattccct    60
attgaataaa tgctgctggg ataactgagt agccatttac agaaaattga aactggacct   120
tttccttaac catatacaaa aattaactca agatggatta aagacttaaa tataaaacct   180
aaaactataa aaaccctgga agacaaccta ggcagtacct ttcaggacac aggcacaggc   240
aaagatttca tgatgaagat gccaaaaaaa ttgcaaaaaa aaaaaaaaaa anaatttta   300 ttaaggggggc                                                        310

<210> SEQ ID NO 84
<211> LENGTH: 523
<212> TYPE: DNA
<213> ORGANISM: human

<400> SEQUENCE: 84
ggtctcctgt aattttcagg aagatgattt gttctttcca gaagaggaga caaaagcaag    60
atagccaaat gtgacatcaa gctccattgt ttcggaaatc caggattttg aattcgagat   120
gaaacaacca gcaatcacag ttaaatctta actttgcctc cactctttgt aggaatgatc   180
agaaatttat ctttatcatt ctgagtgctt caggagtaca ataggaagaa agatactgga   240
gaaagcacta gtgtaatcac catgaagtct gacaacagga gcccattatt tgcgtactgt   300 cccacccctgt atcatggttc tctgggaaca agctttatga ttctcattag agtttatttg   360
ttgattgtca gtagttgcga cttttaaatt atatttcccc cactcaaaga atggtatctt   420
tatatatcaa tgacattcaa taaatgtgta ttatttctaa tgagaatcag ttacaagagg   480
agacttgata gttcagtagt ggctcaaaat ggttgggctg atg                    523

<210> SEQ ID NO 85
<211> LENGTH: 483
<212> TYPE: DNA

<213> ORGANISM: human

<400> SEQUENCE: 85

```
cccgtggtac caggatgatc ttgatctcct gaccttgtga tccacccgcc ttggcctccc      60
aaattgctgg gattacaggc atgagccacc agaaagtttg tgtttaatcc tgaatatgat     120
cactgtttca cttctaattg gagattctgc ctaaggaaag aagttagagt aggtaaagac     180
tattgtcacc cagagtacat tcttgggacc ctaagcggag aagttgccat taatgaggaa     240
ggatgagctc accaaataga tatgccttgt acatacttaa aattgcatga tcattctgat     300
agttatgaaa tggagcttgc atgattctga gcccactgcc tcagctagca ttcctttgta     360
ctggtgttgg aagtttctga ccaaggctgg cagccttggt agcaaggatt accacgtaaa     420
tactatttct gtgtttggta gtgatattag ctattgatct tcaccccccc agaaatttgg     480
cag                                                                   483
```

<210> SEQ ID NO 86
<211> LENGTH: 526
<212> TYPE: DNA
<213> ORGANISM: human

<400> SEQUENCE: 86

```
gaatatattt caagttttat acatattaga tgaattgcat ggtatttag gcaacttaac       60
tataaacaaa tttattcata gaagcattgt tgccaacaat ttagatgacc tcgatgaaaa     120
aacacaccaa ttgacaaaac tggctcaaaa ggaaataaaa aatccaaaca gacctgtaac     180
aagtaaagag attgaaccag taatcaaaaa tctcccaaca aagaaagtcc aggactaaat     240
gagtttactg gcaaactatg ccaaacatat aagaagaat taacactaat ccttctcgaa      300
ctctcccaaa aaatggaaga gaaggagca ccctgtgaca ttctataagg cggacattac      360
cttaacacca aagccagaca aagacctcac aggggaagct acagaccaat atcccttatg     420
aatatagatg caaaaaactt caaatactag caggccaaat ccagcagctt attaaatgat     480
caccagcatg accagtgaga ttatcaaaga atgcagggtg gttcta                    526
```

<210> SEQ ID NO 87
<211> LENGTH: 317
<212> TYPE: DNA
<213> ORGANISM: human

<400> SEQUENCE: 87

```
gggtactcca taaatattag taattattag aaattgacta agatttacat tgagtaagat      60
tattcattg aataagattt tttttttaat cctgagcttc agttttcgca tctctaaata      120
agaatctatt caatcaacag atacttatct ggctcctgga gctatacagc aaaagacctg     180
tggctatagc agagcgtaga attcagggag ttaataacac ctacctgcag aatgtatgtg     240
aaaatttaat gagacaatgt atagttgaag tacttgcttg ttacacttcc tggcatactt     300
tattcactaa ataaatg                                                    317
```

<210> SEQ ID NO 88
<211> LENGTH: 207
<212> TYPE: DNA
<213> ORGANISM: human

<400> SEQUENCE: 88

```
ctagcaccat gagcttcaat accctgttac taaaaataca aaaaattagc caggcatggt      60
ggtgtgtgcc tgcaatccca gctactcagg aggctgaggc aggagaatca cttgaacctg     120
```

```
ggggcagagg ttgcagtgag ccgagatcgt gccattgcac tccagcttgg gcaacaagag    180
tgaaactcgg tctcataaaa aaaaaaa                                        207

<210> SEQ ID NO 89
<211> LENGTH: 401
<212> TYPE: DNA
<213> ORGANISM: human

<400> SEQUENCE: 89
gaatttctgc cgaaaactga ttccatctta tcggatccaa cagaccactt ggggattgaa    60
ttcatggaga gtgaagaagt ttatcaaagg caggtgctgt caatttcatg tatcatcttt    120
ggaattgtca tcgtgggcat gttctgtgca gcattctact tcaaaagcaa gaaacaagct    180
aaacaaatcc aagagcagct gaaagtgcca caaaatggta aaagctacag tctcaaagca    240
tccagcacaa tggcaaagtc agagaacttg gtgaagagcc atgtccagct gcaaaataaa    300
atgtcaggct tctgagccca agctaagcca tcatatcccc tgggacctgc acgtgcacat    360
ccagatggcc ggttcctgcc ttttctgatg acattccccc c                        401

<210> SEQ ID NO 90
<211> LENGTH: 475
<212> TYPE: DNA
<213> ORGANISM: human
<220> FEATURE:
<221> NAME/KEY: misc_feature
<222> LOCATION: (474)..(474)
<223> OTHER INFORMATION: n is a, c, g, or t

<400> SEQUENCE: 90
ggaaattgta aaagtattat ttgagaactg ataaatatcc gtattaagat gaaatcttca    60
caatttacgt tcctctgctg tggctccagc tggtccctct cttcggggtc cctgacttcc    120
cataacacca cttcagtttg taactcagtg ttaatttttat tctgaagtag ccatgcttgg   180
tcggctgtgt gtgtccagtt ctccatgtac tgagctgttt gaatagaatt atgcaaagct    240
acagaggaca tcacaacaga agttattagt gcgaccaagg aaacaatagc taaaattatt    300
atgtctaagg ctctacagac atgatgagta agctcagtta aagaagtttt cacaaaatgc    360
aaagcaggtg tggcagccca agcctcggac agattaacag gaatacatag cccaggggat    420
gtggcctaaa atcatcaaag tagagatatt atgtgtttgc aatgtgctat gatna         475

<210> SEQ ID NO 91
<211> LENGTH: 398
<212> TYPE: DNA
<213> ORGANISM: human

<400> SEQUENCE: 91
gacaaaataa attaatacag atacacaaac acatgtatgc aaaattatac ttttaacaaa    60
gatatatgtt ttacttttga aatatgtttc atttagactg caaacaagc aagaagattt     120 attatgaatc agagttgttt gtgctctcag gaaggaagat aatgatctaa ccaatctctt    180
tcactgggaa ctgttttctg aatattataa ggccccaggg attccagatg gaatacagta    240
taattaactc ttcaccacca aatacctatg ttagaagacc ttgagaataa atgattgcct    300
aatagcaaat ggcatcctac ttcttgacta cacttgcacc tgaggataca aaaggacaag    360
gtgtatttaa ccttagaatg tctctataag atgaaaac                            398

<210> SEQ ID NO 92
<211> LENGTH: 492
<212> TYPE: DNA
```

<213> ORGANISM: human
<220> FEATURE:
<221> NAME/KEY: misc_feature
<222> LOCATION: (467)..(467)
<223> OTHER INFORMATION: n is a, c, g, or t

<400> SEQUENCE: 92

```
gctgcttcac aatcaactgc gaaaggtctt taaatgtcaa gaataaagaa gtccggacga        60
actctgctaa ggtacaattt gtggtaaatt gcctctccac ctcccaatca tgtaatttgc       120
acttcccaga tggttaagga ccatggttcc accaagctct gtgttcatta gaacatggtt       180
tcaagctgag atctccacgc aaaggctatt cagtttcaat ccaaccctg cctcaaattt        240
tggaactttg ggcgatattt ttacccacct cagcttcccc ttcagagaac aggaaataat       300
ctacattgta gagttgtttg gagctggaac tggtaaccat gctcaccaaa gatttaatat       360
tagatttaat attatacaaa tgctgccctc tttctcctgc tctcaccaca tgactgacat       420
acctgccccc attttgcctt ctaccatgat tgtaagcttc ttgaaancct caccagaagc       480
caaggagata at                                                           492
```

<210> SEQ ID NO 93
<211> LENGTH: 278
<212> TYPE: DNA
<213> ORGANISM: human

<400> SEQUENCE: 93

```
ggtttgaaac acatattaaa attgaggcac acaggaaaga actggctcaa gtttagtccc        60
caagttcctt atagtaggaa taggaatcct tagagtataa gcaatccatg catagtattc       120
tgttatctat catgtagatc atttaatctc taatttttg gggtgggat tctcttgttt         180
ctaaatctta cactttcagt ttcttctgtg tcttaaaat agattattga ctgttgtctt        240
aaatactaat aaatacatta aatgtatctt aaatacta                               278
```

<210> SEQ ID NO 94
<211> LENGTH: 544
<212> TYPE: DNA
<213> ORGANISM: human
<220> FEATURE:
<221> NAME/KEY: misc_feature
<222> LOCATION: (425)..(425)
<223> OTHER INFORMATION: n is a, c, g, or t

<400> SEQUENCE: 94

```
ggcccaagaa tctacctgcc tggatccatt aacaccagtg ccagcgtatg ctgccttggg        60
gccaaaggac acacaggctc agaccactgc tgccaccact ggggcctgaa gactggccca       120
cctggtattt caatttctgg caaaacttaa ccagtctgca ctaaaaacca cactctaatc       180
taccaacgaa accagatacc aatgactcta tggccaaaag aaatgataga gactatgcta       240
ctgcttgcat ccagaaccaa agccaagtgt cctctccaac catcaccata gatacatctt       300
caggaaaatg ttctccacta caaaccaaat tcaaaaaatt ggaaaaagca actgttacac       360
caggtgcaca atatcaaca taaaaacaca gagaaatcaa aaagcaagga tatgtgacac       420
atccnaagga acacagtaat tcttcagcaa caaatcccaa tcaaaaggaa ttctcaaatc       480
ctggaaaatg atccacatac tgatactagg aagctcaggg ggagaaagag attctggaag       540
acat                                                                    544
```

<210> SEQ ID NO 95
<211> LENGTH: 509
<212> TYPE: DNA

<213> ORGANISM: human
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t

<400> SEQUENCE: 95

```
ggccatcagt acctatgatg gctcgaaggc tctccatgtc accaacatca aaaaatggaa      60
ggagccctgc cgaatagaac tctacagagt cgtagagagt ttagccaagg cacaggagac     120
atcaggagaa gaaatttcca aattttacct gccaaactgc aacaagaatg gatttttatca    180
cagcagacag tgtgagacat ccatggatgg agaggcggga ctctgctggt gcgtctaccc     240
ttggaatggg aagaggatcc ctgggtctcc agagatcagg ggagacccca actgccagat     300
atattttaat gtacaaaact gaaccagat gaaataatgt tctgtcacgt gaaatattta      360
agtatatagt atatttatac tctagaacat gcacatttat atatatatgg atatggatat    420
atatatagna actactttt atactccata cataacttga tatagaaagc tgtttattta     480
ttcactgnaa gtttattttt tctacacag                                       509
```

<210> SEQ ID NO 96
<211> LENGTH: 468
<212> TYPE: DNA
<213> ORGANISM: human

<400> SEQUENCE: 96

```
gaggagcttg agtttcctca gacttcacaa tacatggaca tatttaatga tacctctgtc     60
cactggttcc ctgtgcaaaa gctagaacag ctctccatag atatttggga gtttcgggaa    120
gaaccagatt atcaggactg tgaggacctt gaaatcatca ggaacaagag agaagatcct    180
tctgctactg actgaactcg ttgtgaggta ctcagtgttg gctgaggtag aagctgccac    240
cagagactaa agggaaggct gctatggagg aactacagag aactcctttg ccaggaaaga    300
acatcaactt ggctgtcctg ttttgaggac gatacccac atgaggactt ggtataaga     360
ttcctgccct acgtggcatt gtcccgtttt acatccttcc ctcatgacct ggcctgatgt    420
ggagtagctc ctgagtaaga agttacccctt ttgaaaaaaa aaaaaaaa                 468
```

<210> SEQ ID NO 97
<211> LENGTH: 352
<212> TYPE: DNA
<213> ORGANISM: human

<400> SEQUENCE: 97

```
gatattagag tacagtgtct taaaatattc atgttttact tggatatcta gaagataaaa     60
ggcattctgt attttatgtc aactattgct agtagcttt acctatggga gtaaatccgt    120
ggaagaagtt ttgctcaatg tatgctaaca tgaagcagct ttctgttttc agtttattcc    180
ctcagatatt agtttgtttt ttctctttt aatttggaaa gcaaaatgag gccagcattc    240
gttctatgtt tgtgttagag cagcggtctc cagaatgtat tgaagggcca caagtgttat    300
aaagttaaat gatgactgct gactttcagg cttcctctct atacttaagt ac            352
```

<210> SEQ ID NO 98
<211> LENGTH: 490
<212> TYPE: DNA
<213> ORGANISM: human
<220> FEATURE:

-continued

```
<221> NAME/KEY: misc_feature
<222> LOCATION: (489)..(489)
<223> OTHER INFORMATION: n is a, c, g, or t

<400> SEQUENCE: 98
aaatatttaa ggcctctgac attggagcat caatgacgat ccatgccttt ggggcctact      60
ttggcttggc tgtagcaggc atcttgtatc gatctggact gagaaagggg catgaaaatg     120
aagagtccgc atactactca gacttgtttg caatgattgg gactctcttt ctgtggatgt     180
tttggcccag ctttaactcg gccattgctg aacctggaga caaacagtgc agggccattg     240
taaacacgta cttctctctc gctgcctgtg tgctcacagc ctttgccttc tccagcctag     300
tggagcaccg aggcaagctc aacatggttc acattcagaa tgccacccttt gctggaggag    360 ttgctgtggg cacttgtgcg gatatggcaa ttcacccatt tggttctatg attattggga    420
gcattgcagg aatggtctct gtgcttggat acaagttcct gactccactc tttactacta    480 actgagganc                                                            490

<210> SEQ ID NO 99
<211> LENGTH: 534
<212> TYPE: DNA
<213> ORGANISM: human
<220> FEATURE:
<221> NAME/KEY: misc_feature
<222> LOCATION: (528)..(528)
<223> OTHER INFORMATION: n is a, c, g, or t

<400> SEQUENCE: 99
ggcttttcaa tctgaagttc tgcgaacaaa aagaaaaagg tcatatgctc ctttccccac      60
agcaaccaat gtaaaacagc aggggcaggg agataactgc tatagacact cctgttccaa    120
caggtggaaa ccaaggtgca cagaagtcac tggttcatag caattctgaa atccatttga    180
gtacaggttt gcagttctac actcaaagcc tgggaataac tccctatggc ttttggttcc    240
accttctggg ctcttggttt tatcctctaa gtcatccttt tttgtgtgaa agggagatgt    300
gtttggacct aaatagtttt cttagcctgc ttcctgtttg tagaaatgcg tttgtagaaa    360
gggtccaaag gccccttttcc tttttgtact ctttttcagc tcaagctgac agtatttctg    420
acaatacaat tctcttaaaa caattttga atctactgtg aatcttactg ggttttagtc     480
caggagacaa aagccatggc agcaaatacc tttgagatat gtcttttnct acct          534

<210> SEQ ID NO 100
<211> LENGTH: 482
<212> TYPE: DNA
<213> ORGANISM: human
<220> FEATURE:
<221> NAME/KEY: misc_feature
<222> LOCATION: (436)..(436)
<223> OTHER INFORMATION: n is a, c, g, or t

<400> SEQUENCE: 100
gcttcaatac cctgcgtctc cctgaaactt tctaatgggt atgggtagta tataagaaag     60
ctattgacat ttatctgctt tgtcctatag ctgactatat tattcccta ttaaactttt    120 aaattatgga accactatgc ttttactaga gaaatttaa acacacacat aaaaattcag    180
atcatttgca gtcctaccat caaagacaac tactttaac agctgctata aattttttct    240
gcacggcata tcataaatta aaatatattt tataaaaata ggatcatatt gtgcatgttg    300
ttttactgtc acctagtaaa gatttagtga atgtaggtta atactaatgt tataatcaac    360
attattatca actgtcaaca taaatcttcc tgcgtaaaga tcaggattca gactgattta    420
```

```
aaacataaaa actaanaaat gggctgggtg tggtggctca cgcttgttat ccagctcttg    480
gg                                                                   482

<210> SEQ ID NO 101
<211> LENGTH: 495
<212> TYPE: DNA
<213> ORGANISM: human
<220> FEATURE:
<221> NAME/KEY: misc_feature
<222> LOCATION: (453)..(453)
<223> OTHER INFORMATION: n is a, c, g, or t

<400> SEQUENCE: 101
gagatttgac agaaaaagaa tcagcaaact tgaagacaga tctgttgaaa ttaacctctc     60
tgagaaaaag aaagaaacaa gaatgaagaa caatgagcaa aacttctaaa acctttggga   120
taccaccaaa tgtacccata tacacataaa aaaagagaaa ggggcagaat attggaagaa   180
agaatggttg aaaatgtctc acatttgatg gaaaatatta atctacctat ccaagaagct   240
cagtgaactc caagtaggtt aaactcaaag agctccatac ctagacatat cataatcaaa   300
ccctcaaaag acagaatttt gaagaggca agataaaagc aactcatcac acaagggagt    360
ctcaataaga tttacaactg acttctcatc agaaaccatg gaaacaagaa ggcaatgggt   420
acatttaaaa ataactaagt ataattggat tgnttgtcac aaaggataaa tgcttgaggc   480
actagatacc cattt                                                    495

<210> SEQ ID NO 102
<211> LENGTH: 405
<212> TYPE: DNA
<213> ORGANISM: human
<220> FEATURE:
<221> NAME/KEY: misc_feature
<222> LOCATION: (389)..(389)
<223> OTHER INFORMATION: n is a, c, g, or t

<400> SEQUENCE: 102
ggaaatgcaa ggggctgcat gacctaccag gacagaactt tccccaatta cagggtgact    60
cacagccgca ttggtgactc acttcaatgt gtcatttccg gctgctgtgt gtgagcagtg   120
gacacgtgag gggggggtgg gtgagagaga caggcagctc ggattcaact accttagata   180
atatttctga aaacctacca gccagagggt agggcacaaa gatggatgta atgcactttg   240
ggaggccaag gcgggaggat tgcttgagcc caggagttca agaccagcct gggcaacata   300
ccaagacccc cgtctcttta aaatatata tattttaaat atacttaaat atatatttct    360
aatatcttta aatatatata tatattttna aagaccattt ttggg                   405

<210> SEQ ID NO 103
<211> LENGTH: 502
<212> TYPE: DNA
<213> ORGANISM: human

<400> SEQUENCE: 103
actcaatgtc aggtgggctt tctccttgtg gtgggtgcca cagctccagg ctgtcatatt    60
catagcttct agtccagtga aaagaaatca ctaagtgtgc tgatgagggt cctagaacta   120
attctcattg gcttaacttt gatcatgtgg ccatggcact gcataaccca gttggattat   180
gcctgaatta tgtgctcact tttggagcta gggagagagt cagctccata tagactacat   240
agactgggtt cacatgggtc acatggctaa tgaagaagcc agggtttgag tccaggactg   300
tctgattgcc acttgttctt agccacttct ctacctgcct tcagtgttag aaaacaaatg   360
```

```
cataccgatc acagaatatt tgaaaaatag agagcttgct ttggcagcat gtatgctaaa    420
atcggaagga tacagagaag attagcatgg cccctgtgca aggatgacat gcaaatttgt    480
gaagtgtcca tattttgaa ta                                             502
```

<210> SEQ ID NO 104
<211> LENGTH: 303
<212> TYPE: DNA
<213> ORGANISM: human
<220> FEATURE:
<221> NAME/KEY: misc_feature
<222> LOCATION: (167)..(167)
<223> OTHER INFORMATION: n is a, c, g, or t

<400> SEQUENCE: 104

```
ggaaataacc attgtttgta ggtctgacag caagaaatag agatagaaga gcttcatttg     60
aagttttgaa ctgtttaccg taaaaatatt aatggtgaat gcttatcaat catgtctgtg    120
tgtcaggcac tgttctaagt gctttatgtt cattaaccat ttgcagnaaa tactgttttc    180
cttcccacaa acaagtgag gaaagagagg cttagagagg ggaagtcagt gtccccaaat    240
cctgcagttg ataagtgatg tacttaacca ggatttaacc ctcggcagtc tgatcccgag    300
ctc                                                                 303
```

<210> SEQ ID NO 105
<211> LENGTH: 512
<212> TYPE: DNA
<213> ORGANISM: human
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t

<400> SEQUENCE: 105

```
cccttccccg aaactcaacc acccttgtaa tactgagatg accaccaggc taggaggagg     60
agaggagcct aaattctgct aaggtgtaga caaaaacaat tgtgaggcgt tattccagaa    120
gccacaagat atgcaacttc ctcagttacc cctgcagata atgttacttt tgtagaacct    180
aggattggcc ttctgagata tcttctcagg attttgcatg gtctgatgac cgatggctcc    240
accgggacca gccaacggct tctgtgtccc cacccagaag cgactcagan aaagaggaca    300
gcttcgacac cctatgattt catctctgac ccaaccaatc agcactcccc ataccctagc    360
ctgctaccta ccaaattacc tttgaaaaat ccctaacctc cnagccttag atgagtttga    420
tttgagtaat aactctgcct cccacatggg ggggctggca tcatgtcatt tacctctttc    480
tttactggca ggggcctggg tctcctgnaa ct                                  512
```

<210> SEQ ID NO 106
<211> LENGTH: 504
<212> TYPE: DNA
<213> ORGANISM: human
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (444)..(444)

```
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (485)..(485)
<223> OTHER INFORMATION: n is a, c, g, or t

<400> SEQUENCE: 106
ctcatggaat gccttatcta ccatcatact attccacaca gcattgcctc tgaccaaggc      60
actcacttta ttgctaaaca atggccgcag tggactcatg ctcatagaat tcactggtct     120
taccatgttc cccatcatcc tgaagcagct ggattgatag aacagtagaa tggccttttg     180
aagtcatgat tacaatgcca actaggcaat agtttgcagg gctggggcaa agttctccag     240
aaggccatgt atgctctgaa tcagcatgca atatgtggta ctgttttttcc catagccagg    300 attcacaggt ccagggaatc aaaacacatg gaagtggaag tggcaccact caccattgcc     360
cctaatgatc ctcccgcaaa attttttgcat actgttcctt gacattatgt tctgctggcc    420
tagaggctta ntttcagagg gagnaaactg ccacaggaga cccacatgnt tccttaaact     480
ggaanataaa attgcccccg ggcc                                            504

<210> SEQ ID NO 107
<211> LENGTH: 381
<212> TYPE: DNA
<213> ORGANISM: human
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t

<400> SEQUENCE: 107
ggttggggaa agggcccctc cccacctgac acccactggg gtgcacttta atgttccggc      60
agcaagactg gggtaacttc aggctcccag tgggcactgt gcccatccct cagcctctgg     120
attctcttca tggncaggtg gctgccaggg agcggggagc ttcctggagg cttcccaggg     180
ccttggggaa gggtcagaga tgccagcccc ctgggacctc ccccatcctt tttgcctcca     240
agtttctaag caatacattt tgggggttcc ctcagccccc caccccagat cttagctggc     300
aggtctgggt gcccctttttc ctcccctggg aagggctgga ataggatana aagctggggg    360 tttttcagagc cctatgtgtg g                                              381

<210> SEQ ID NO 108
<211> LENGTH: 500
<212> TYPE: DNA
<213> ORGANISM: human
<220> FEATURE:
<221> NAME/KEY: misc_feature
<222> LOCATION: (418)..(418)
<223> OTHER INFORMATION: n is a, c, g, or t

<400> SEQUENCE: 108
cagaaacatg gactacacat aaggttctct atttaagtta aatacaaatg caacttttta      60
gtgagctttt aggactactc ttcaaaaaaa gtgtattgct cagaatgatg acctgtaaat     120
gtaagagtgg caggcctctg tctgtgaaag tcagaacaca gggctcgagc ctctggaact     180
gaccctttgc aagtctttac aaaagaaaaa aggcagtggg gagagagagt gttttggtta     240
```

```
catcagaaat aattgagatg ggaaagaata gtgcagctcc atagaggaga cggactgtag    300
acaatgagat taagcttcaa tcactgctcc tcagcaatgt gaagaatcaa agtcagggca    360
agaaagcgaa agcttggact tctattcaaa gtggcagcag agtgggaggg cggtaccntt    420
ctagcccagt gctgctgagc ttgtgtgaaa tcagacctga gatggcttga agcagcaaga    480
acacatgggc attgcccaga                                                 500
```

<210> SEQ ID NO 109
<211> LENGTH: 509
<212> TYPE: DNA
<213> ORGANISM: human

<400> SEQUENCE: 109

```
gtttgagacc agcctgggca acattgtaag accctgttcc ttgaattgcc ctgggagatt     60
tcctcagctt gtactggagg tgtgtggccc catgaagccc atagtcaccg ttcaccctga    120
gagacgctgg cttttgggct cacacgcctg ctgcggggca gccccaggag atggccaccc    180
tgtttctcct ggagctggag ctgcacgtgt tctcagcaac tgtggtggct gtcctgtttt    240
gtttgcatct tataaacctt tacctgatta cattttcctc ttcaatttag ctgctagaaa    300
acttaaagtc agattggtgg ctcgccagta atgagagttt agagtagagg taaacttttat    360 gacatagtct tagactcttc actttctcct cagccaacat gattcacatt tactttattt    420
tgctgtactg tgagtgtctt tgtgtttcct gaattccttc tggaataagg caggttgtta    480
gtaagcacag gtttctggtc catctcata                                       509
```

<210> SEQ ID NO 110
<211> LENGTH: 514
<212> TYPE: DNA
<213> ORGANISM: human
<220> FEATURE:
<221> NAME/KEY: misc_feature
<222> LOCATION: (487)..(487)
<223> OTHER INFORMATION: n is a, c, g, or t

<400> SEQUENCE: 110

```
gatatatata gtttaaatct gattgtatga ccccaaatcc cccttctctc tgttctcaca     60
cttccctgct agtttttctac ccttataatt ttgcaaaaag tcaaagaag aaaaagtact    120 aaaacttaca ccatttgatt tttctctttg ctactgctag tttgaaaggg ccctctgcat    180
agcctgtttt cacatttcct ttgcattgct ttattttctt tcactgttgg cgtgatgatc    240
tgatttgagg aggtgccgcc gtgggctttc ctgatagtag ttcatctttt acagtttctg    300
tctctcaggg tgtgagtctc tctttgacac tgaacacagc agccattcca ctgaactgac    360
ttgcttccaa gagaccatcc tcacttcact aagacagtag ctcattcctg gagagatttc    420
ctgccttgat ggttttttagg caaatcttta gtcctaggga gttttattga gacctgacag    480
aagtatnaga ccaaaacaca tcacttgaga tagc                                 514
```

<210> SEQ ID NO 111
<211> LENGTH: 544
<212> TYPE: DNA
<213> ORGANISM: human
<220> FEATURE:
<221> NAME/KEY: misc_feature
<222> LOCATION: (475)..(475)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t -continued

<400> SEQUENCE: 111

```
gattttaact agatttccag gagattcatg aacatattac agcatgggaa gtactgactt     60
gttgaaaaca tattcagtac atggtaacca ttattatagt cctgatctac tcaattcatt    120
ttttccttat cccaggcata ttcttgctct tctcgtgttg ctcacaacta cctgcctgga    180
tgaatttagg aaagttgcag gatacaaggt taaaacacaa gatcaaatga acaatccgaa    240
aatgttatta agaaaacagt tccggccggg cgtggtggct cacgcctgaa atcccagcac    300
tttgggaggc cgaggcaggt ggatcacgag gtcaggagat caagaccatc ctggctaaca    360
cggtgaaacc ctatctctac taaaaataca aaaaaattag ccaggtgtgg tggcacgcac    420
cagtagtccc agctactcgg gaggctgagg caggagaatt gcttgaacct ggaangcaga    480
gattgcagtg agctgagacc gcaccctgca ctccatcctg ggnaacagag ggaaatttgt    540
ctcc                                                                  544
```

<210> SEQ ID NO 112
<211> LENGTH: 457
<212> TYPE: DNA
<213> ORGANISM: human

<400> SEQUENCE: 112

```
ggtggtatga tatcaaatag tttaatgtgt aattaaagtc ccaagtggaa aggatagagg     60
ggagaagtag tttgaagaaa taacagctaa gcatttttga acatctgggc catctctagg    120
tctgcttcta ttgaccattt cccctcttga ccatgggtca tatatctagc tttgttgtgt    180
atctcatcat ttttttgagg tatgctgtaa cttttttgtgt aaagagtaga ggctgcagta    240
atgtatttac ctctggtaaa gatgtgctct tttctcaagc agttagtgtg tgagacaggg    300
tcaatctaat ttgtaattga tcatctctga gctttgttac attcagaaaa tcactggctt    360
tccatgcttt gagggtggca tcaatacttt cccttccagc agagtttgac atttggccct    420
catgaaattt ctgagatgtc ttattttttac actggag                            457
```

<210> SEQ ID NO 113
<211> LENGTH: 529
<212> TYPE: DNA
<213> ORGANISM: human
<220> FEATURE:
<221> NAME/KEY: misc_feature
<222> LOCATION: (521)..(521)
<223> OTHER INFORMATION: n is a, c, g, or t

<400> SEQUENCE: 113

```
gggcttcaga gggtagaggc cccaagcatt ggcagcttcc atgtgatgtt gagcctgtgg     60
gtgcagagat gtcaagaatt gagatttggg aacctctgcc tagatttcag aatatatatg    120
gaaacacctg gatgtccagg caaaagtttg ctgcaggggc agagccctca tggggaacct    180
ctcctagggc agtgtggaag ggaaatgtgg ggcagagccc ccacacagag tccctgttgg    240
ggcactgcct agtggagctg tgagaagaag gccacagtcc cagaacggta gaccccagaa    300
tggtagaccc cagaatggta gatcaaccac caacttgcat cttgtgcctg aaaagctac    360
agacactcaa catcagcctg agaaagcagc caggagggag gctgtactct gcaaagccac    420
aggggcggag ctgcacaaga ccatgggaac ctatctcttg catcagcatg acctgaatgt    480
gagacatgga gtcaaaggag atcattatgg agctttaaaa ntttgactg                529
```

<210> SEQ ID NO 114
<211> LENGTH: 239
<212> TYPE: DNA

<213> ORGANISM: human
<220> FEATURE:
<221> NAME/KEY: misc_feature
<222> LOCATION: (205)..(205)
<223> OTHER INFORMATION: n is a, c, g, or t

<400> SEQUENCE: 114

```
ggatcacctg aggtcaggag ttctagacca gcctggccaa catggtaaaa caccgtctct    60
aataaaaatg caaaaattag ctgggtgtgg tggcaagcac ctgtaatccc agctacttgg   120
gagactgagg caggagaatc acttgaatcc aggagtcaga ggttgcagtg agccgagatc   180
acaccactgc actccagttc tgggngataa gagtgaacct gcatctcaaa aaaaaaaaa    239
```

<210> SEQ ID NO 115
<211> LENGTH: 380
<212> TYPE: DNA
<213> ORGANISM: human

<400> SEQUENCE: 115

```
gcctcgtgca ggtccgttac ataggtatac atgtgccatg gtggtttgct gaacccatca    60
acccgtcatc ttcaaagata aggccttcag tatatcaaga tcagtggatc aaagaaacat   120
cctcaagaaa ctaagaaaca acacaagatt ctctctgatg aaatgcttaa gtataaggaa   180
aatgatggaa gacacagaag agcagcagaa ttgggtagaa gactactaca gatgccagat   240
cgccacttct gaaagaaagg cttacgacaa ctggctctgt gtttaagcct cgcagaggga   300
gatgcaagag aagaaggctg cctacaagca gcacagatag gaaatgattg aaaaacagag   360
agtgctggag agacccatta                                               380
```

<210> SEQ ID NO 116
<211> LENGTH: 530
<212> TYPE: DNA
<213> ORGANISM: human
<220> FEATURE:
<221> NAME/KEY: misc_feature
<222> LOCATION: (518)..(518)
<223> OTHER INFORMATION: n is a, c, g, or t

<400> SEQUENCE: 116

```
tttgctcata gaaattctcg gaaattaggt gcctgaagtc ttacactcat ttttttaaaag    60
tatagcatct gcttccagtt ttcagtgact ccattgatga tgcatgcggt ttggccgtat   120
catactgagc tttaaacaca agatttataa acatggtatg tagtgcatct tttgcaaaca   180
ggttggcagc ggtactgtgt gacttggtct tttgtggctt ttttgagaaa aatgaaacac   240
tttgcatgta tagtttttc tcccaactac ttgtgagtag ttcctggtta taaaacgtta   300
tgaaggtagc acataaccct tttctagaat gaagaggctt tgagctacc agtgtaaggg    360
gataggtaga aatagagatg aaaggcacta agatgtccta ctctttaaga gcattgaacg   420
ccagttgtgc catttattca agtcatcttt gaacttatgt taaatggggg taaaacagg    480
taactacttc aggccgggct catgcttgta atcccagngc tttgggaggc               530
```

<210> SEQ ID NO 117
<211> LENGTH: 320
<212> TYPE: DNA
<213> ORGANISM: human
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (315)..(315)

<223> OTHER INFORMATION: n is a, c, g, or t

<400> SEQUENCE: 117

```
ggacatctat actctatagt caggtctaac atatgaaata attaacttgt gtgttgaagt    60
acaaatact ataatttgtc atttaaggga atgtaagatt tagatgatcc ttaatgctcc    120
ttgcaactta aagattctgc gcctcactga cgttaagctt gtatgagacc tgtagtctgt   180
tggaatacat aagcagctgc ctgtgttaca cagttgtgag gtgggnaata tacttgtgat   240
gattttaaag agctctttct attgtcactg acaacagagt ctaaaaaaac ctgaattatt   300
gcataatcaa ataanaccta                                               320
```

<210> SEQ ID NO 118
<211> LENGTH: 501
<212> TYPE: DNA
<213> ORGANISM: human
<220> FEATURE:
<221> NAME/KEY: misc_feature
<222> LOCATION: (499)..(499)
<223> OTHER INFORMATION: n is a, c, g, or t

<400> SEQUENCE: 118

```
gggagaaagt gtttgcaaaa gattcatcca gcaagggact aatatccaga atatgcaagg    60
aagccaacag taagaaaaac aaccccatta aaaagtgggc aaaggacatg aatagacgtt   120
tctcaaaaga agacatacaa atggccaaaa ggtatgtgaa aaaatgtgca acatcactaa   180
tcgtcaagga aatgtaagtg aaaaccacag tgaggtgtct taccccagtc agaatggcta   240
ttgttaaaaa gacaaaaaaa tatactactg gtgagagtgt gaagaaaagg caactgttac   300
agactgttgg tgggaatgtt acaataatta ggacaggcac tatgaaaaac agtttggaaa   360
tttctcagaa aaccgaaaac agaactacca tatgatccgg cagttccact gctgggtatc   420
tatctaaagg aaaagaaatc agtatatcaa agaaatacct gcactcccat gtttatcatg   480
tcatttgcag cagcttgang g                                             501
```

<210> SEQ ID NO 119
<211> LENGTH: 599
<212> TYPE: DNA
<213> ORGANISM: human
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (515)..(515)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (572)..(572)
<223> OTHER INFORMATION: n is a, c, g, or t

<400> SEQUENCE: 119

```
gcaaaatatc tcatgtaccc ccataaacat atacacctat ttgtacccac aaaaatttaa    60
aaataatttc aatgtttgaa gactcattat taaaataata gcagtttcta taaatttaat   120
atttcaataa aactcccaat atttattctt aacactggaa aaactttcc aaaatgcata    180
tggcagaaat atgggcgttg atgaaaggac agcatcaatt aatgagggat cctccccctt   240
gacgaaaata ccttccacca agacccacct ttaatgctga ggattacatc tcaaaatgag   300
```

| | | |
|---|---|---|
| atttgggcag ggacaaatat ccaaactata tcactagcta tatcaggagc tgtaactata | 360 | |
| actatatcag gaactataac aattctatag aaaaaaaatt aatctgaaaa ctggacaaaa | 420 | |
| atctgaatag gcatttctcg aaagaagaca tacaaatggc aaacaggcat atgaaaagna | 480 | |
| ctcaacatca ttgatccatt agagaaagca aatcnaaact acaangagat atcatctcac | 540 | |
| cccgttaaaa tatcttctgt ccaaagacag gnacacaatg ctgagagatg tgggaaaag | 599 | |

<210> SEQ ID NO 120
<211> LENGTH: 255
<212> TYPE: DNA
<213> ORGANISM: human
<220> FEATURE:
<221> NAME/KEY: misc_feature
<222> LOCATION: (231)..(231)
<223> OTHER INFORMATION: n is a, c, g, or t

<400> SEQUENCE: 120

| | | |
|---|---|---|
| gacatttact gtactacagg gaatctctca tttcaaaatg acctgtgttg cagttattgt | 60 | |
| ttataaaact gttcatttat ctgacgtaag gggctaatca aactgcttaa gtacattcct | 120 | |
| ggatgtttgg aagattttta agcgccatag agagggtact tatgctatgg aaattgtgtt | 180 | |
| tatatatata tgcataattg ccactgaaat tctgaacaga cccaaaggaa naaaaatact | 240 | |
| gtgatttaaa taaag | 255 | |

<210> SEQ ID NO 121
<211> LENGTH: 504
<212> TYPE: DNA
<213> ORGANISM: human

<400> SEQUENCE: 121

| | | |
|---|---|---|
| tcgtctgata ttagggaaga ttgaattgcg ttaatctctt agccatgtgt ggggaggcca | 60 | |
| gatggacctg ctactttgta gccacagcca cacttgacct cttttgaggtt cctttctcc | 120 | |
| accagcctgg ctgcagcgtg gtgaggaaaa gcatgtggtt tgaagttgca gccctgagtt | 180 | |
| caagtcctag tttcttccct tacaatgtaa ccctggccct gctcccctta ctgcagattc | 240 | |
| tgccaagagc cttaccctct ctaagcttca ttcagtcctg tatcgtgggc atggtaatag | 300 | |
| tactgaatgc agagttgctg aggattaaat gcacgttaag tacatagtac agttcccagc | 360 | |
| acacagtgat catatatgtg atagcccttt ttgcagttat ttttatcaaa tggcaatcag | 420 | |
| agaagccttc caggacaact ttatctaaaa tagcactccc tcctctgctt tatttttata | 480 | |
| caaaatttta tatagcattc ctta | 504 | |

<210> SEQ ID NO 122
<211> LENGTH: 509
<212> TYPE: DNA
<213> ORGANISM: human
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t

<400> SEQUENCE: 122

| | | |
|---|---|---|
| tttttttaact ctataaaggc aaattaactt tttccagtga taaatggtag cagaggactg | 60 | |
| gtgttacaac acttgtactt aattaggaat ttatttcagt ctgacaatat caactacagt | 120 | |
| atgccttcca gtaagtaaat gaggtctttta tgttaaagtc tgaccaaatc atggttagaa | 180 | |

```
tgcaaaactt acttttaat agtaggaaga aggataaaga ccttaaactc aggacagatg    240
aaacatggct tgatgaattt atacctctta tctgtcttct caaagatctc caaaaaacaa    300
aagtacagtt aacacactgc aaggagttgt aggacagaac ctacaatatc cctacttcct    360
tatccttcct cttccaatac acaaaaacga atactgaaag ggttnaagtc tttagagttg    420
ttcatcaaaa tttctggtat gattgtactt tctggctgtc gtgtggctgg gaggggttag    480
gtgcctantc tggccattgt aagtcaaag                                     509

<210> SEQ ID NO 123
<211> LENGTH: 500
<212> TYPE: DNA
<213> ORGANISM: human
<220> FEATURE:
<221> NAME/KEY: misc_feature
<222> LOCATION: (487)..(487)
<223> OTHER INFORMATION: n is a, c, g, or t

<400> SEQUENCE: 123
catgaacttt aatagggaaa gatgtaaaga aaaatgtcag ttctctccaa attaatctct     60
gtattcagtg tacttccagt cataattaca aggaaatttt tcatggatct tgaaaaactg    120
attgtaaaat tgatatagac aagtaaatac tcaagaataa tcaagagaac cctagaaaaa    180
tgtattgcat ctgacagcaa gatttactac aaaatcataa tagacagtat ggtttgatgc    240
taggatggac aattaggtca ttggagcgta atggaaagcc cagaaacaca ttgagatcct    300
tgtgaaattt taatatatag gaaagagacc ctacaaatca acatttattt aataatactg    360
agtgagcctc tactgcattc tatgcactgt tttagtccct ggtgacataa cagtgaataa    420
aagcaagtag taggcagggt gcggtggctc atacctgtaa tccagcactt tgggaggatt    480 gcatganccca ggagtttcag                                              500

<210> SEQ ID NO 124
<211> LENGTH: 566
<212> TYPE: DNA
<213> ORGANISM: human
<220> FEATURE:
<221> NAME/KEY: misc_feature
<222> LOCATION: (442)..(442)
<223> OTHER INFORMATION: n is a, c, g, or t

<400> SEQUENCE: 124
aaagaataga gaaagtgaaa tagatgacat ttggcttcca tctcattccc caccgccctc     60
gcccagcgtc ctcttcccag cccttcattt tctctagtag gggtgtgtct atgagagaga    120
ggatattgct tgttactgat ggaagccaga atcctcccca tttcttctcc cgcaatccag    180
actctcacta gaatatctaa atgatgtcct ctgaacttaa gtcctttatt tctgtatgtt    240
ctcaaatggc agatccattc aaaaaattct ggagccaatt atttaagttc cagataacaa    300
ggccgggcac tgtggctcat acctataatc ccagcacttt gagaggctga ggcagatgga    360
tcgcttgagt ccaggaattc aaggccagct ttgacaaaat agtgagaccc catctttaca    420
aaaacaaaca aattagctgg gnatgatggt gcacacctct agtggctact caggaggctg    480
aggcagaaga ttgcttgaga caggagttgg agctgcagtg agctatgatg atacacccac    540 tcccctggg gacaagcaga cccatt                                         566

<210> SEQ ID NO 125
<211> LENGTH: 467
<212> TYPE: DNA
<213> ORGANISM: human
<220> FEATURE:
```

<221> NAME/KEY: misc_feature
<222> LOCATION: (466)..(466)
<223> OTHER INFORMATION: n is a, c, g, or t

<400> SEQUENCE: 125

```
gaccatctcc tgcattgtag gatgttcagc attttttggtt tccgcctact aaatatcagt    60
tgggcatgcc agtcgtgtga cagccaaaaa tgaagtgggg ggtaccagct tctgttatta   120
ataccctcag gcctgtgatc tcctggctcc ttacagctct taggaaggga acagtagtct   180
ttccctgcac attgttctgt gcagttagta gcgacataca ctgacgcccc aggccaaagt   240
tcctactgtg tcctacttga aggatgattt tgttttcttg agaccctgtc tgaaagaaag   300
agagaaagaa agaaagaaag agagagaaag aaagaaagaa agaaagggaa agatggaagg   360
aaggaaggaa aaagaaagag aaagagagag agagagaaag aaaaagaaag aaaagtaaga   420
agaaaaagaa aaagaaagaa agtagaaaga aaaaaaaaaa aaaggng                 467
```

<210> SEQ ID NO 126
<211> LENGTH: 444
<212> TYPE: DNA
<213> ORGANISM: human

<400> SEQUENCE: 126

```
ggcgtagttc ttcagattta ctttttctgaa cagtattttt tgaagtataa tttgctgctt    60
gcattttgaa attagattac cacgttgggt gatctttata tttgaaattc aagtctttaa   120
aattttaaaa aaatggagaa aagtacagag gataacttgt atgtaccaca tgtataatat   180
tcatttttaat gttttaatgt tcattttcaa acagtgaaac aaaagaacct ctgacatgat   240
tgttctttta gcttgctaag actgccagaa ttttcccaaa actgttctta ttaaaataaa   300
atttttaggct aggcatggtg gctcatgcct gtaatcctag cactctggga ggctgaggca   360
ggcagattgt ttgagcccag aagttcaaga tcaggatggg caacatggtg acacctcgtt   420
tgacaaaaaa aaaaaaaagg gggg                                          444
```

<210> SEQ ID NO 127
<211> LENGTH: 455
<212> TYPE: DNA
<213> ORGANISM: human
<220> FEATURE:
<221> NAME/KEY: misc_feature
<222> LOCATION: (448)..(448)
<223> OTHER INFORMATION: n is a, c, g, or t

<400> SEQUENCE: 127

```
gggggtgtct gagaacctca tttcctcatt acatccctcc ctggtcagcc atatgtgttc    60
agcagccaaa tggcaaaatt caccccaga actgtgattg tcttccctaa tctggaaggc   120
ccacaagtgt ggagaagcac tggagaccct ccagaagcag tagtgctagc agtcaggggc   180
tactctccct gccgggcccc gtgcaagggc ctggccaccc tatcccaggt atgtgacact   240
tggctggctg ttctttattg tcctgctagt acctgttgta aagcttcttt tattaaagaa   300
gagcaggaga ttgaagtgtc ataaattgaa gagattcaca ccaacacggc acatgtatac   360
atatgtaaca aacctgcacg ttgtgcacat gtaccctaga acttaaagta taataacaaa   420
atatgtatta aaaaaataaa taaataantt gagag                              455
```

<210> SEQ ID NO 128
<211> LENGTH: 500
<212> TYPE: DNA
<213> ORGANISM: human
<220> FEATURE:

```
<221> NAME/KEY: misc_feature
<222> LOCATION: (499)..(499)
<223> OTHER INFORMATION: n is a, c, g, or t

<400> SEQUENCE: 128
agttaattgc tgctatcatg tttaaatcaa taagagtaaa aacaagtata acaagtaact      60
aacatttatt gatgaatgaa tactatgtga taagtgttgg acacagcatt tacataaaat    120
atctaactta atatttacag tgattctagg aggttttcat tattatttttt gtctctagtt    180 tacatatggc taaatgaagc tataaagtgg ctaagtcacc ttttgaaatt ctcgcagtaa    240
atgatgatgc tgggatcccg agtcggatct gttgcactcc tagaccccaa agtctgttga    300
ggaaattcat atttcttttg gcctctactg aagagtgagt ttgatttttt tttccctaga    360
aatcatgaga atagttaaca tttttttataa gcaaactttt gggggttaca aatttgatgt    420
tataataaac gttcctgtcc aggcacggtg gctcacgcct gtaatcctag cattttttgga    480 ggccaggtgg gcagatcant                                                500

<210> SEQ ID NO 129
<211> LENGTH: 471
<212> TYPE: DNA
<213> ORGANISM: human
<220> FEATURE:
<221> NAME/KEY: misc_feature
<222> LOCATION: (449)..(449)
<223> OTHER INFORMATION: n is a, c, g, or t

<400> SEQUENCE: 129
agccattaat gaaagatga ataaagtcaa ctgtgtaaaa atgtttaaca aattttacct      60
ggtaccaacc actacaaaca aaagacaacc tgagaaaaga atatatgcaa cttgtcacag    120
gcaaaaggct aatttccgta atatatacag cattcctaca aactaacaag gaatgcattg    180 ttaattttttg tgcattgcta gtgagaaggt aaagtagtgc gatctttgca gcaacaattt    240
gtaagtatca aaattataaa tgcacatgcc ctttgactta ggaattttac ttatagaatt    300
gtgaatgtac agcttattca ttgtagcatt gtttaaatgg cagtacctca aaaatctatc    360
agtagggact aattaaatga actctggtcc attatatagt catagaaatt aatgaagagc    420
caggcacagt ggctgaagcc tgtaatccng cactttggga ggatcacttg a             471

<210> SEQ ID NO 130
<211> LENGTH: 444
<212> TYPE: DNA
<213> ORGANISM: human

<400> SEQUENCE: 130
cccaagccat agttgtgagg aaagctaagg aagcgattac tttgtattttt cagcctgtac      60 catcaaggga ggtaggttct tccagcgggg aagctggttg aaagaatgcc tgtcatgtag    120
gcaactaaca atgtcaaccg tagttactat atcatatttta ttcttcttaa atatctatcc    180
tttttgtcct cttgttcatt ttcctactgc cactacttta atcaggtcct tatctttttt    240
tcccccttag accattacaa gaactctact actcttgctt ccaatctgtc tctcctccaa    300
actgttatct cagtgttgta gtagtgatct tcctaattgc agatatggtc ttgtcactta    360
cctacctcat gttcttcagt ggctctgtaa aaaaatccta gactggtatc tggaacactt    420
taaagcatat actttggtgg tcag                                           444

<210> SEQ ID NO 131
<211> LENGTH: 487
<212> TYPE: DNA
```

```
<213> ORGANISM: human
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t

<400> SEQUENCE: 131
gcatcattat agtactcaag acactaaaac agcttctagc aaaatatatt aaagcttgca      60
gaggccaaaa atagaaaaca tctccctgtc tctcccacat ttccctcaca gaaagacaaa     120
aaacctgcct ggtacagtag ctcacacctg taatcccagc agtttgggag actgtgggaa     180
gatggcttga gtccaggagt tctagacagg cctgagaaac ctagtgagac atccttctct     240
taaacaaaac aaaacaaaac aaatgtagcc atgcgtggtg gcatatacct gtggtcccaa     300
ctactcagga ggctgaaacg gaaggatctc ttgggcccag gagtttgagg ctgcagtgag     360
ctataatctt gccattgcac tccagcctgg gtgaaaaaga gccagaaaga anggaaagag     420
agaaaagaga aaagaagag agaaaagacn gaaagaccgg aaggaaggaa ggaaggaagg     480
aaggaag                                                              487

<210> SEQ ID NO 132
<211> LENGTH: 571
<212> TYPE: DNA
<213> ORGANISM: human
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (539)..(539)
<223> OTHER INFORMATION: n is a, c, g, or t

<400> SEQUENCE: 132
gagggagacg gttgagagca cacaagccgc tttaggagcg aggttcggag ccatcgctgc      60
tgcctgctga tccgcgccta gagtttgacc agccactctc cagctcggct ttcgcggcgc     120
cgagatgctg tcctgccgcc tccagtgcgc gctggctgcg ctgtccatcg tcctggccct     180
gggctgtgtc accggcgctc cctcggaccc cagactccgt cagtttctgc agaagtccct     240
ggctgctgcc gcggggaagc aggtaaggag actccctcga cgtctcccgg attctccagc     300 cctcccmtaag ccttgctcct gccccattgg tttggacgta agggatgctc agtccttcta     360
aagagttttg gtgcttttct gggtccctca gctcccgaag ctcttgagaa aactatcaaa     420
ggctagaatc cccttctaac tctttttttc cccatgataa gcgcagtcgg tcacagttca     480
ggtgagttct tacttggcat tcagnaaatt acaaatctgg gtagttgtct gggcacganc     540
gaaatggcgt ctatccctgg tgctgacctg g                                   571

<210> SEQ ID NO 133
<211> LENGTH: 508
<212> TYPE: DNA
<213> ORGANISM: human
<220> FEATURE:
<221> NAME/KEY: misc_feature
<222> LOCATION: (79)..(79)
<223> OTHER INFORMATION: n is a, c, g, or t

<400> SEQUENCE: 133
gataacagaa gaataactgt gtatttggat ttacataggt agactttgtg agagtagatg      60
```

```
ttttaaaaaa atgactcana ttagtacctt ttaactgttc agaaaaacaa aacctcaatt      120
ttctggtttt cctgcccatt ttctctgctt cttcacttgg ggcagagaaa aagcaagttg      180
cagaatatgc actacatgct gctatttgtt tgaaatttta aaagacaata taatactgca      240
tacagataaa ggatacatac acatctagta agagtataaa catgcatgag aataataaac      300
accaaattca gggtaatagt tgcctctgga aggggaggta tggaggggtc acagaggact      360
tcagctttat tggtaaaatt tcataagttg ggtagcaagg acacaaatgt atgttattca      420
ttgtaccttt ttgtatattt aaatatttca taatcaaatt tttcctgaga atgaaactct      480
ttgtgacttc ccatggtagt ggaacaaa                                         508

<210> SEQ ID NO 134
<211> LENGTH: 391
<212> TYPE: DNA
<213> ORGANISM: human

<400> SEQUENCE: 134
gaattaaggg gaagtttcaa taaaaaagat gatgtcccaa agaaagtgaa tggagaaaac       60
ttcatagtaa ggacaatctt gaatatattg cacaacattg aaacaaaaaa aattaaatgt      120
tggaaacgga tccaaattta gaaagagtat gataactggc caagttataa aaaggattct      180
catttcatat tgtgcattat aaaatgagaa ggcaaacaat gttcaaatta ctcttgataa      240 gatttttttca aagaaacaaa acaattatca atgtttctaa tattgtatat aactgtgtaa      300
aataaatatt tgattatttt tgaattttcc catatattta tcaccaacaa taagagaatt      360
ttagtgttct gacacaattg tttaaaggaa a                                     391

<210> SEQ ID NO 135
<211> LENGTH: 496
<212> TYPE: DNA
<213> ORGANISM: human

<400> SEQUENCE: 135
aaacaacaaa agcactggag gggctcaata gttagttagt ttgtcccaga cccttctaga       60
atattgagat cctggacagt gcttctgaga aacctgcagt ctctgtccaa ggagccctta      120
aggaagaaag gcaggagtgt ggggcaggaa gaccggcttc ccctttccat tccacacggc      180
tggctcgcaa tattctgttt ctcctgcgac agcctggttc ctccctgctc ccagctcgc      240 ctctgccacc attcttccct cagtccagat caagagttca agggacgggg acagatgatc      300
agaaaggccc agctcaggca agggaagggg agaaaaggga actcgtatat gcggtgggtg      360
ggaatggaaa agtagtacag tcactatggg gggaggttcc tcaaaaaact acaaatagaa      420
cggccatatg atccagcagt cccacgactg ggcatttatc caaggaagg gaatcagtgc      480 atcagaaaaa ccctgc                                                      496

<210> SEQ ID NO 136
<211> LENGTH: 471
<212> TYPE: DNA
<213> ORGANISM: human

<400> SEQUENCE: 136
gattttctat aaccttcata caaagaggag acatgggatc ttacccttt ctctaatccc       60 agctaaaact gacagtatcc tttctattgg ctgatgtgtg gcatgagagt cgttattgca      120
actgttagtt ggaccaagat atatgtcaca gtcttacctg tgggtaggga gcaaacagga      180
gagtcacatc acctgtattc tgggccagga atatgtcaca atcttccctg acacaaggga      240
```

```
ccaggcagaa gagtcacatc acctgggtac tcagccagga atacgttaca accoctgcag    300 ggtgcaggct gcagagtcac ctcacctcag taataagccc agcaatatgt caaaatgctt    360
tctgtgggca aggcccaatt acgagagaca catcgtctgt ttgctgatgc cagcaatatg    420
tcacaatctt ccctgtaagc agggttcagg gagaaaagac agccaatctc t             471
```

<210> SEQ ID NO 137
<211> LENGTH: 629
<212> TYPE: DNA
<213> ORGANISM: human
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t

<400> SEQUENCE: 137

```
agtaagacat ctctgatttg gaggatatat tttttagtct acaaagaatc cttgaataca     60
tcaagataga gcatatctta caaacatatg ggcaaccata tgacatcatc ctgtgtcact    120
actagttttg gtcatgtgaa tccaaagggc cctttggtga tgttactcac caatacactt    180
cccagtcata taaaattaga taccttccca tccttaacca cttttagtag aaagaatgcc    240
cttcagtcca cactgtgtta ctaggcccaa agcagtgtta ctagtagtct atttcttaca    300
gcatacaaaa ctgctctgta tcagtttgcc agggctgtca taacaaagta ccacagactg    360
tggcttaaac aacagaaata acaaagtagc acagactgtg gcttaaacaa cagaaattta    420
ttttccacaa ttctggaggc cgaaagtctg agatcaagga ggcagcaaag gtggtttctt    480
ctgaggcctt tctccttggc tgnagatgcc attatctcct gngtctaata tggcctcoct    540 cctgcaggct gggcctantc cctttttagaa acacagtata tgcataggcc acctatgctc    600
atttactcga tcttaagact gcccaatcg                                      629
```

<210> SEQ ID NO 138
<211> LENGTH: 515
<212> TYPE: DNA
<213> ORGANISM: human
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:

```
<221> NAME/KEY: misc_feature
<222> LOCATION: (457)..(457)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t

<400> SEQUENCE: 138
taagtaaaag aantagcaaa ttgaaagant tttaagagac gaagacagaa taaaaagcnc    60
cctacgttta aaggagtttt ttagaagaaa atagaaacaa tgggggaaga tggttaaaaa   120
ttaataataa cnttccagac ttgaagaaaa aaaactgaat cttcacatta cagaagcaca   180
ctatgtctag ggcaggataa ataacaaatc tacactagga cacatcctga tctgcaacac   240
actgaagata aagagagaac agtaaaaata tagattacta cctgtaagat tactacctac   300
aaactaagag ggctcagact aacagcagat tttttcatta gttaacactg aggcaaggag   360
acaatagaac agtatcttca aggcacagca gacagtacta aacaactcaa ctcggtcaan   420
ctactttctg gccgcacttg tgaaatcaan gctcccngta tttgatagca cttcatcatt   480
tgnatctata acacntctca gtgggagaat accaa                              515

<210> SEQ ID NO 139
<211> LENGTH: 481
<212> TYPE: DNA
<213> ORGANISM: human
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t

<400> SEQUENCE: 139
gctgagcttt tttgtgctca actaaggatt gtgagagttg agagcttgat tgaacnctta    60
agtttcataa agattacttc aaaaatattt agtatcaaca aaaatagagg tctgtattgt   120
aggtttaaaa actcattttt aaataattat ttggtggtaa ttcattatac taaacttctc   180
agtttctttt tattcaggct ccttcctcag agaagcttcc tgttatgtac cttatggatt   240
ctattgtgaa aaacgttgga agagagtatc tcactgcctt tactaaaaat ctagttgcaa   300
catttatttg tgtgtttgaa aaggtggatg aaaatactag gaaaagttta tttaagttac   360
gttctacatg ggatgaaata ttcccttttga agaactttat gccctggatg tcagagtcaa   420
ttcattagat cctgcttggc ctattaacct ctaccccaa tgtgatacgt ctagcatccn   480
g                                                                  481

<210> SEQ ID NO 140
<211> LENGTH: 359
<212> TYPE: DNA
<213> ORGANISM: human

<400> SEQUENCE: 140
gctgttcttg agattgtccc agctattctt ggccctttgc atttctatat aaatttata     60 atcaggtgat caatttttac aaaactctgc tgggattttg attggaattg agttgaatca   120
atagatcaat ttggggaggt ttggcatttt acagtattta gtcatctaat ctgtgaatac   180
```

| | |
|---|---|
| aacacacccc tttattaggg tttccttcat ttgtcttagt gttttgttgg agattttgt | 240 |
| ataaagtctt tcacagctta tttaagactt attcctaggt cttcaagatt tgcatgtgga | 300 |
| tgagaaagga attaaaattt ttttaccctt ataattgttg ggggaccagt atatagaga | 359 |

<210> SEQ ID NO 141
<211> LENGTH: 516
<212> TYPE: DNA
<213> ORGANISM: human
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t

<400> SEQUENCE: 141

| | |
|---|---|
| gtgtataatg acaactgtgt aatgtatcca ccattatagt atcatataga atagtttcac | 60 |
| tgccctaaaa ttcccctctg ctccacctat tcattcctcc gttcccccctt attcctggca | 120 |
| accactgatc tttttactat ctcaacattt ggttttgcat tttccagaat gtcatatatt | 180 |
| tagaatcata caatatctag ccttttcaga ttgattggcc tctttcactt aataatgtgc | 240 |
| attcaaggtt cttctatgtc tttgtctttt cttggnttgg taactcattt ttgtcattag | 300 |
| atagtatttg ttgtatgggt ataccacagt ttgtccattc actttcctta cttcaagttt | 360 |
| tagcaattat gactaaaact actgtaagca tttttccttt cataattgag attttgttgg | 420 |
| ttgtgttgag gaccagtcca cagatatctc aatttgtaca caattcttaa catacgtacc | 480 |
| aagaatctaa aaagcttatg tggtgcagnt cttttt | 516 |

<210> SEQ ID NO 142
<211> LENGTH: 449
<212> TYPE: DNA
<213> ORGANISM: human
<220> FEATURE:
<221> NAME/KEY: misc_feature
<222> LOCATION: (434)..(434)
<223> OTHER INFORMATION: n is a, c, g, or t

<400> SEQUENCE: 142

| | |
|---|---|
| gactcagagg aaagctgccc tggtcctgag tgtgactccc atggtccccg tggggtctgt | 60 |
| gtggttggca atgagctctg tgctgtcagc tttcatgagg gagctccctg gctggttcct | 120 |
| gttctttggg gtcttcctcc ccatgacttt gctgctgctc ctcctcatcg cctacttcag | 180 |
| gatcaaactg attgaggtta atgaagaact gtcccagaac tgtgatcgcc aacataatcc | 240 |
| caaggatggc tcttccctgt accagagaat gaaatggacg tgaagttggg gactttccaa | 300 |
| taactaaagc acaatgagtt tctactggtc agcaagcaat ggccaacagt tcagctaata | 360 |
| aagtaggttg ataactagaa ccatagcaaa atagaaagaa tactaagata ctcattctga | 420 |
| acatactgaa aagnggcagc tattatcta | 449 |

<210> SEQ ID NO 143
<211> LENGTH: 512
<212> TYPE: DNA
<213> ORGANISM: human

<400> SEQUENCE: 143

| | |
|---|---|
| catgaaggat atataataca tagtaagaac ttttaatgta catataattg gagtctcaga | 60 |
| aagataggag agacagttag gcaggggcaa tatttgacaa gataaagatc aagaaatttt | 120 |

-continued

```
gaaaactatt gaaagatctc agctcaagaa ttaaagaaat ttaatgaaac ccaagcagaa      180
taactacaaa aagactaca cacatgcatg ttgatatagt ttggatattt gtcctctgaa      240
atctcatgtt gaaatgcgat ccccaatgtt ggaggtgtga cctagtggga gatgtttggg      300
tcatgggagt ggatccctca tgaatggctt ggtgccatcc ccttcatgat tagtgagttt      360
ttgctctatt agttcacgta agaactggtt gtttaaagag cctagcacct ccttcctgcc      420
tccctcttgc tctgtctcac catgttgaca tgcctgctct gcgtttgcct tccgctacaa      480
gtaaaatctt cctgaaactt cccagaagct ga                                   512

<210> SEQ ID NO 144
<211> LENGTH: 459
<212> TYPE: DNA
<213> ORGANISM: human
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t

<400> SEQUENCE: 144
ttccaggtgg acttagccat aggaaaatan tactaatgta atttaacaaa ttgctgcatg       60
tattccattt aaaaatatgt ttaaattgtc ctaaaacaaa ataattttct ccctaggagt      120
atgcatttgg ctacagtgtt ttgaaacaga aaccttagaa taggtcattg gtatgggctg      180
aactgtgtat cccccaattc atttgttgag gtcctaactc ccatttcttt tgaatgtgac      240
tgttcggaga tgaggccttt aaagaggtga cttaagttca aaggaggctg ttagtctaat      300
ccaacatggt gtcctttgga cataagagat accagcaatg tgtgcacaga acaaagacca      360
ggagaggaca cagtgagaag gcagttatct gcaagcaaag agagaggctt cagaanaaca      420
aaatcaccag caccttgatc ttgactccta tctcaaata                            459

<210> SEQ ID NO 145
<211> LENGTH: 517
<212> TYPE: DNA
<213> ORGANISM: human

<400> SEQUENCE: 145
gggtataggt ggacctaaat tccttatcat atcctttatt aattcagcca gtgtatccac       60
cagttttttg tttatgtttt taagtaacct attatctctg gatttcatga aggtgtaata      120 tcgttttttgt taaactgaat agaattgtat agcgatgact tcttaattat aatttgattt      180
gactgcaaaa cttttttcctc ctctaagagg agatgatgtc tgctttaagc tgtaatgttt      240
tgccatgttg caaaaagcca taataataag tataaaaaag ctttttcctt tacaatttca      300
tgttaatctg gttgtctgt ccaccagaga cagatcttct gtgacagcct ccttatgcag      360
gtctatcatt atttgataga atgtcttcta aaatacttca ctcacattgt aattcaaatt      420
agaaagtcat tccaaaagga tcatgtcatg ttgacctcat ttcatcggaa ctgcagtata      480
tttttggtgg gtaattatat tagggttttc tattttg                              517

<210> SEQ ID NO 146
<211> LENGTH: 491
<212> TYPE: DNA
<213> ORGANISM: human
<220> FEATURE:
<221> NAME/KEY: misc_feature
<222> LOCATION: (482)..(482)
```

<223> OTHER INFORMATION: n is a, c, g, or t

<400> SEQUENCE: 146

```
cacacataaa cggcagtgtt aaaacatgaa tgactgtgtc tgcctgtccc caaacaggac      60
agcactggga acctagctac actgagcagg gagaccatgc ctcccagagc ttgttgtctc     120
cacttgtata tatggatcag aggagtaaat aattggaaaa gtaatcagca tatgtgtaaa     180
gatttataca gttgaaaact tgtaatcttc cccaggagga gaagaaggtt tctggagcag     240
tggactgcca caagccacca tgtaaccect ctcacctgcc gtgcgtactg gctgtggacc     300
agtaggactc aaggtggacg tgcgttctgc cttccttgtt aattttgtaa taattggaga     360
agattatgtc agcacacact tacagagcac aaatgcagta tataggtgct ggatgtatgt     420
aaatatattc aaattatgta taaatatata ttatatattt acaaggagtt attttttgta     480
tngattttaa a                                                          491
```

<210> SEQ ID NO 147
<211> LENGTH: 527
<212> TYPE: DNA
<213> ORGANISM: human
<220> FEATURE:
<221> NAME/KEY: misc_feature
<222> LOCATION: (525)..(525)
<223> OTHER INFORMATION: n is a, c, g, or t

<400> SEQUENCE: 147

```
gaaattattc aaacttcaaa ccagtattga aagcagttgg aaaccagcta atagtttctt      60
aatctcagat ttcgagatga atgtaaactg tattcttttg aaatgtgcaa gtgtttgatt     120
catgccattt gataaacttc tgccttgtag tcattgtttg atgggaccaa cttgtaaagt     180
atgagcctta ataaatctc catgctgaaa atgtgttct aatgcaacac aaaaacatga      240
agtgactgcc cagaggtaga gttagtgttt aggtggaaag ggagatgaca gctttccaaa     300
gaaggaccta aaacacacca agattgtctt ctacaggaat tgctgggcag gtctccgact     360
aaaggtctta tgatgaaaag gaagaaacaa gcccccaaca caaggctctg atactactgg     420
taaatgtagg agagaattaa gaatctgtta attaaaatcc aaacagagct tatttcagta     480
gtcaagttac ctgacatgat aattatttct gcaggatatt gatgntt                   527
```

<210> SEQ ID NO 148
<211> LENGTH: 465
<212> TYPE: DNA
<213> ORGANISM: human
<220> FEATURE:
<221> NAME/KEY: misc_feature
<222> LOCATION: (458)..(458)
<223> OTHER INFORMATION: n is a, c, g, or t

<400> SEQUENCE: 148

```
gggtataaag tgtccctttt tattctagag gcttttcctt taattcagag attagtggag      60
ataataacgt cagtcaaggc taatgtggta catggaactt gctaatggag gttggacatt     120
ctgtttcagt cttacatgga tattgtttca ttggtgttga ggaagaaaaa aattagatac     180
taccatgcat tgggacagca taattctaat attacattga atatggcttt ttaaaaataa     240
gtattaaaaa gccaatcgtt ttctccattt atctatcttt tttgtttgtt tttaatttgg     300
ttgattgata tgcacccagg ccgtcttatt tttacttgtt aatgtctgtc taggaagaac     360
tgtgattgga aaggaattaa ttattataca aataaatctg gtaggatatg agtggagtaa     420
gtttgcttga aacagaagta tatttctact ttgaatcncc cacca                     465
```

```
<210> SEQ ID NO 149
<211> LENGTH: 574
<212> TYPE: DNA
<213> ORGANISM: human
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t

<400> SEQUENCE: 149
ggccttgcag cagcgggaag agaaattggc agctgttttc cagttcatag agaaagacct        60
gatattactt ggagccacag cagtagaaga cagactacaa gataaagttc gagaaactat       120
tgaagcattg agaatggctg gtatcaaagt atgggtactt actggggata aacatgaaac       180
agctgttagt gtgagtttat catgtggcca ttttcataga accatgaaca tccttgaact       240
tataaaccag aaatcagaca gcgagtgtgc tgaacaattg aggcagcttg ccagaagaat       300
tacagaggat catgtgattc agcatgggct ggtagtggat gggaccagcc tatctcttgc       360
actcagggag catgaaaaac tatttatgga agtttgcaga aattgttcag ctgtattatg       420
ctgtcgtatg gctcccctgc agaaagcaaa gtaataagac taataaaaat atcacctgag       480
aanctatnac attggctgtt ggngatggtg ctaatgacgt aagcatgata cagaaaccca       540
tgntggcata gaatcatggg taaaaggag acgg                                   574

<210> SEQ ID NO 150
<211> LENGTH: 452
<212> TYPE: DNA
<213> ORGANISM: human
<220> FEATURE:
<221> NAME/KEY: misc_feature
<222> LOCATION: (451)..(451)
<223> OTHER INFORMATION: n is a, c, g, or t

<400> SEQUENCE: 150
gggttttaga agctgaagcc aagcctaggg tagcatcgtc tgtacggtgg tgaggcccag        60
cacagcggta gctgcctagt gggaatgacc ccctgagcat gcagagccca gagtcactgt       120
ccatctgcgt tcccagagaa caattgtgaa gagtcctaga acaggaactc tgaatcagac       180 tgtcagggc ctatgtagcc aaaatgttac taaatataaa attcctgtcg tcttcagtct        240
tcatgctttg tcactgtaaa aagaacaaaa agcatttta ctataattta aaggagctgc        300
ttttttatag cacatactat ttcgctttgt actatatttg atagttgcag ataatttag        360 actgtagaaa aactttgttg tatttgtact gttcttgaat gtttcaaaga aagtgcttta       420
cttggttgcc ataattttct tgtactgctg na                                    452

<210> SEQ ID NO 151
<211> LENGTH: 475
<212> TYPE: DNA
<213> ORGANISM: human
<220> FEATURE:
<221> NAME/KEY: misc_feature
<222> LOCATION: (410)..(410)
```

```
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t

<400> SEQUENCE: 151
gagtttttag aagacagcta ccaagtatat atttggggtt gtagagttca aataataaat      60
ctctagcttc ataatgtttc taagcttctc tcccttttaa aattttttggt attagggatg    120
gattgataac tttaatggac caagtggtct ctttattgcg gtaagtaaac cttttgattt    180
atttaatatt ctatacattt ttctgttttt tgtatatctt taaatatata tacactatgg    240
cttatatctt aaggtgttgt ttttaatttc aacaaaggca gggaaaggaa ttcttcgaac    300
aatacgtgcc tccaacaatg cccttgcaga tcttgttcct gtagatgtag ttgtcaacat    360
gagtcttgcg gcagcctggt attccggagt taataggtat atgaggggan atggcgctta    420
ttaaaatata gtaactgaaa agggagacat agcttttgan aaaggtaata atccc          475

<210> SEQ ID NO 152
<211> LENGTH: 563
<212> TYPE: DNA
<213> ORGANISM: human
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t

<400> SEQUENCE: 152
gggcctccaa aataaacaac aggactgctc agtagtcaga gtgaattttg ggtggggttt      60
gaaagagttc cagcttttcct ctgctaatgg tgacataaaa tgttcatttc atacccatgc    120
atatacactg atgtatacat gtagttgagg aggcagtggc agaagccaga aggctttctc    180
tgccatgagc tcctcctagg agccctgggt tgcagagggt gaggactgct aggaaagtcc    240
gtcagttaag gccgaaggga cattagcttt gccttaaacc acattggctg tgcttgcctt    300
tgtgtcttca cctgatttaa tgggttttag ctcacactct ccgaatctat ttacctccaa    360
gtcagttaag gcagactgta ctgttgacaa agctaagcag aacagaattt ccccatggct    420
tctagcttca aggaatccca gctatttatc catcaccaag aaatgaancc catgggtggc    480
tgacggttca tttactccag cccagggtgt tggatttcaa ttagtgcatt cgcttttcct    540
ctagnagagc tcacctttaa gtc                                             563

<210> SEQ ID NO 153
<211> LENGTH: 407
<212> TYPE: DNA
<213> ORGANISM: human

<400> SEQUENCE: 153
gcatttaggc atctttctat tatcagtcta cacagacctg cctttgtctt gtatatggtt      60
tcagagtatt attttgtatg tctctaaaat gcattaataa atcccctaca gataaatatt    120
cgagactatt tttagtcttt tgctattaaa aacaatgctg cagttaaaaa tcttgcattt    180
atttctttgc acaggtataa tttctctgca tgttaaattc cctagctgca taattataaa    240
gcttgtttac ttaaaactgt gtctatcccc ctcagaaaag atggtttcac tgaattacac    300
tcacaccata taggtgtgag aagtactttt agctctgact ctgacaaata ctgtgtacgt    360
```
caaaccttgt aatctttgcc agtctatgaa ggaaaaaata tatcttg 407

<210> SEQ ID NO 154
<211> LENGTH: 534
<212> TYPE: DNA
<213> ORGANISM: human
<220> FEATURE:
<221> NAME/KEY: misc_feature
<222> LOCATION: (511)..(511)
<223> OTHER INFORMATION: n is a, c, g, or t

<400> SEQUENCE: 154
ggataagggc tttcttaagc tttcaggtgt atgtatcctc tagatgtaga caataatgtc 60
ccatttctaa gtcttttcct tttgcttctc cttaaattga ttgtacttcc aaatttgctg 120
ttatgttttt ttcctaatac tgtgatctat ctgatctgca gacaagaacc ttgtctctgt 180
tgaagagcat caaggggaga ttatgtacac attgaaactg aagtgtggtg ttactgacgg 240
aatgtgcagt aactcctcag atatctgtta aggcatttcc cagatgtgat gccagccttc 300
ttacctgtac tgaaagatgc ttagcttaga aaaaaacaaa acagatgcaa aatcagataa 360
ttttattttg tttcatgggt tttcttattt acttttttaaa caaggaagga atattagaaa 420
atcacacaag gcctcacata catgttattt aaagaatgaa ttgggacgga tgtcttagac 480
ttcactttcc taggctttta gcaaacctaa ngggggtatc catattttgc gtga 534

<210> SEQ ID NO 155
<211> LENGTH: 546
<212> TYPE: DNA
<213> ORGANISM: human

<400> SEQUENCE: 155
gtgctgatta gaggtgatgc tgtagaggta aacagaggca acccggtcaa gacatctggg 60
cttcctgaaa acagcaagga accactgaag gatcttaagc aggatttgtc atgtatcttt 120
ttcaccaaac tgcaaattcc aggagcccag tagcagtgtc tcttttttct tcttcacatt 180
atttatccag ggcctaaccc agtgcatgat acatagaaaa tgctcggtaa acatctgaag 240
aataaatggg atgatcagat atgcagaaac atcacttgtc aataatgtga aaacgtgtg 300 agaaataaat gctgaaaaaa ttaaaacagt agccacggag aaaggcacag attaaagaga 360 ttctgttta agggatgatg cctttgatga gcagaagtta tcaatgataa ctccataaat 420
ttgacctggg gaagagtgca tattactatt ctgcacttaa tagaggaatt caggtagaga 480
gcagttaggg agtcagaaaa gatatatatg ctgggcttat attcttggaa actccactct 540
ccaccc 546

<210> SEQ ID NO 156
<211> LENGTH: 501
<212> TYPE: DNA
<213> ORGANISM: human
<220> FEATURE:
<221> NAME/KEY: misc_feature
<222> LOCATION: (494)..(494)
<223> OTHER INFORMATION: n is a, c, g, or t

<400> SEQUENCE: 156
gcgagggtgt tcaagcagtt aatggttgtg ctaactcttg tttctactga agcgggtttt 60
gcaaagctga catcccttaa agataacttg ggctttcgga agcggcaagg aaatggcacc 120
cgtagttgcc aggacaggtg gtgtcctcgg ccaggactaa gagccagctc atctttgtaa 180
cattcataat acgggaaact gaggaccagg tggctcggaa aagagatgag ttccagcttt 240

```
tacctaacac agggttctct cgtcgtcccc caacccctcc agctcggctt ctttgtgtcc    300
agggttgtag attttttggat agaggtgttt ctgattctag tgagtctgag aactggaaaa   360
gaccaaggag gggttgatga tttacaaggt ccatagaaaa acttttttgtg tggtcggaag   420 ttggccaagc agaggcccca gcctgatgct actgccccccc cccccccaag atctgaattc   480
cctaaagaac agaggggttca g                                             501
```

```
<210> SEQ ID NO 157
<211> LENGTH: 465
<212> TYPE: DNA
<213> ORGANISM: human

<400> SEQUENCE: 157
gcaacagagg cttcatcttt tgaaaacttc attggctaaa agtgtcttct gtaatactga    60
tagtgaagaa actgttttta catccgagat gtgtttgatg aaagaagata tgaaagtgct   120
gcaagacagg cttcttaagg acatgctaga agaggagctt cttaatgtac cagagaact    180 gatgtcagta ttcatgtctc atgaaagaaa tgctaatgtg tgaaatctag ttttttatcac  240 catactttat ctaattatta ttctctgtat ataactgagg aaataagaat agtcctacaa   300
agagaaaaat atacatgtca ccgaagcaag tgtacccttt ataggaaccc tcaaattaaa   360
aaaaatgtct tttaatggat gagagggacc actatacatg agtccagcca gaagacttct   420
gctatacata ttttttttaa tttggagaaa agcttagaaa ctttt                    465
```

```
<210> SEQ ID NO 158
<211> LENGTH: 354
<212> TYPE: DNA
<213> ORGANISM: human
<220> FEATURE:
<221> NAME/KEY: misc_feature
<222> LOCATION: (10)..(10)
<223> OTHER INFORMATION: n is a, c, g, or t

<400> SEQUENCE: 158
ggcgaggggn tgttacatct gatcagggca aaaggggctg tgctccttgg acactttgca    60
cagccccagt gggcttcttt ctcctctgtt agtgtggtta atgttcatct gcctgcatcc   120
ctgagtcacc caagtgtaac ctcagccata acacgtactg cagccggaac ggtgtccgca   180
agctcagcgt ccctctcccca tgcactttct gaactttggt cttttaacca ggttaccag   240 ccgctttctg cctctttgtg cttttgaggg ttttttggat tgtttggttc tgttctgatt   300
ttaaataaag atgattattt ggcccaggat gagggtgcaa acaagaaact cttc          354
```

```
<210> SEQ ID NO 159
<211> LENGTH: 276
<212> TYPE: DNA
<213> ORGANISM: human
<220> FEATURE:
<221> NAME/KEY: misc_feature
<222> LOCATION: (267)..(267)
<223> OTHER INFORMATION: n is a, c, g, or t

<400> SEQUENCE: 159
gtgaaatggg gtgcccgggt tcctctcgtt tttccttcaa tctacctagc atgcatttta    60
cacacattgg aggagtcgta tgcactgttt ttctgttgct gatggaggca agcaggcctt   120
ctaattagtc taacttaaac ggatgggatt cacttaacaa aagcaagaag aaaagcacac   180
gaacaggtgt cttaatgcat ttggatagtt tctttgcggg gtgtgtgtgt gtgtgtgtgt   240
gtgtgtgtgt gtgtgtgtgt gtgtgtntct tggaga                              276
```

```
<210> SEQ ID NO 160
<211> LENGTH: 446
<212> TYPE: DNA
<213> ORGANISM: human

<400> SEQUENCE: 160
gtgccgttag aaagacattg aaacgtgatg cattaaaggg ttctttattc ctctccttta      60
ttcaaacttt ttatttaaac tacctccttt tttgtaattc atccactaaa ctactaaaaa     120
ctccattata attatcctcg gattgaacca agtcgatgat accagccctg tggtccgcta     180
gtgtatcatt actgtgaacg gtctggcctg gctttgtgct ttaattgctt ggggaggctg     240 acagggagc agccctggga ggaagctgct ggttccctgg gcacaggaag tgcttgttcc      300
ttgttctgga gactcaagac attcccagaa tcttcttaag cagagctgct ggggagtagc     360
ccctgtagca agtaccatgc tcttgacagg cagcatgaga gcgtgactcc catgacccac     420
ctgtgctcaa aaaaaaaaa aaaaaa                                            446

<210> SEQ ID NO 161
<211> LENGTH: 576
<212> TYPE: DNA
<213> ORGANISM: human
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (471)..(472)
<223> OTHER INFORMATION: n is a, c, g, or t
<220> FEATURE:
<221> NAME/KEY: misc_feature
<222> LOCATION: (482)..(482)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t

<400> SEQUENCE: 161
ggttaatttg aaatctaaca aggtggtttg taataatgct gaggagatat aagaccctta      60
aaatgaaagt tacaacattg ttcttataaa aggtaactaa aattgttact gttggaaata     120
actgattttc tgagtaatgt tttaaactaa tttggtgaca ttttaacagt aattagctat     180
tttgagtgga atattttca tttctcttca acaaaagca aaggtacgat gctgttttct       240
atcattttgg aataactgca ccctgccttt tgtgttttg taaactcctt gactcattct      300
ttcatgtgtc accaagtact tttctcatga gagtcaacat atatttgttt ccaaatgtcc     360
acaagtgtac aatagtgtaa aggtggtttt taaaaacata gcccggtgtg gtggcacgtg     420
cctttagttc cagctactca ggaggctaan gcaggaggat tgcttgancc nngctgtgtg     480
gntcaccata ntgtgtttgt gactagctct gcactccacc tgggcacata gngggacttc     540
atctctaaac aaacaaacaa attaccttag cctatg                                576

<210> SEQ ID NO 162
<211> LENGTH: 538
<212> TYPE: DNA
```

```
<213> ORGANISM: human
<220> FEATURE:
<221> NAME/KEY: misc_feature
<222> LOCATION: (509)..(509)
<223> OTHER INFORMATION: n is a, c, g, or t

<400> SEQUENCE: 162
gctcaaactc ctccttaacc ggccaggttt acattttgat gtgaatctgg acttctctcc      60
ccttcgaagt cttgatcttc ccatattcac attatatata ctgtccattt tgctcaatct     120
gtcttctact caagtgattt ctgcatgtat cttatctccc cactaggcag tacttgatta     180
agtgccagat gactagcaga ggcaagacat gctctgagtt agaaggagtc atcatgattt     240
ttgaagtttt caccaagtag agagttaatt tggtctttta aggttgggga ggtttctgca     300
gtcaggaata gggggagagt accagggaca tggagtggtt tatgcaaagc aaacaaataa     360
gaaagcaaaa atgaacagag attagacaac tttgctatca aggggagtag ctgcgatctg     420
gctggaaaaa ctgtgaataa gaggcaagta tttgttcggg agggcggggt ttctctactt     480
attcatgata aaatttgata tattgcatnc atcaaaaaca acagaacgct tttgagaa     538

<210> SEQ ID NO 163
<211> LENGTH: 412
<212> TYPE: DNA
<213> ORGANISM: human
<220> FEATURE:
<221> NAME/KEY: misc_feature
<222> LOCATION: (375)..(375)
<223> OTHER INFORMATION: n is a, c, g, or t

<400> SEQUENCE: 163
aaatttctac gcatacggct tttctgtcac ctacagctgt gaccccgct tctcactctt       60 gggccatgcc tccatttctt gcactgtgga gaatgaaaca ataggtgttt ggagaccaag     120
ccctcctacc tgtgaaaaaa tcacctgtcg caagccagat gtttcacatg gggaaatggt     180
ctctggattt ggaccatct ataattacaa agacactatt gtgtttaagt gccaaaaagg     240
ttttgttctc agaggcagca gtgtaattca ttgtgatgct gatagcaaat ggaatccttc     300
tcctcctgct tgtgagccca atagttgtat taatttacca gacattccac atgcttcctg     360
ggaaacatat cctangccga caaaagagga tgtgtatgtt gttgggactg gg            412

<210> SEQ ID NO 164
<211> LENGTH: 533
<212> TYPE: DNA
<213> ORGANISM: human
<220> FEATURE:
<221> NAME/KEY: misc_feature
<222> LOCATION: (526)..(526)
<223> OTHER INFORMATION: n is a, c, g, or t

<400> SEQUENCE: 164
ggcagcacac gccccagctg ctgaccctgg tgcccagggg ctgggatgcc cacaccacct      60
gccaggccct cggggtgtgt gggaccatgt ccagccctct ccagtgtatc cacagccccg     120
acctttgatg agaacagcag cgagcaggcc ataccacagg caatgctcca ggcctgtgtt     180
ggctcctggc tggacaggga aaagtgcaag caatttgtga agctgagccc cgcctcacac     240 ccaccccat gcactcaaag attggatttt acagctactt gcaattcaaa attcagaaga     300
ataaaaaatg ggaacataca gaactctaaa agatagacat cagaaattgt taagttaagc     360
tttttcaaaa aaatcagcaa ttccccagcg tagtcaaggg tggacactgc acgtctggc     420 atgatgggat ggcgaccggg caagctttct tcctcgagat gctctgctgc ttgagagcta     480
```

```
ttgctttgtt aagatataaa aagggtttct ttttgtctttt ctgtangggg act         533
```

<210> SEQ ID NO 165
<211> LENGTH: 400
<212> TYPE: DNA
<213> ORGANISM: human
<400> SEQUENCE: 165

```
gggcgaaggc actggctggc caggccaagg ccttttcggc cgccgcctcg ctgcgccgcc    60
tcaattcggc agtggaatgc gtgccgtaca ctcaggccct tacgccagcc actgccctag   120
acctggtccg ccgatatgat gtggtggctg actgctcgga caacgtgccc actcgctacc   180
tggttaatga cgcatgtgtg ctggcgggtc ggcccctcgt gtctgccagt gccttgcgct   240
tcgagggcca aatcacagtc taccattatg acggtggccc ttgctatcgc tgcatattcc   300
cccaaccacc cccagcggag acagtgacca actgcgcgga cggcggggtg ctcggtgtcg   360
ttaccggggt cctgggctgc ctgcaggcct tggaagtgct                         400
```

<210> SEQ ID NO 166
<211> LENGTH: 367
<212> TYPE: DNA
<213> ORGANISM: human
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<400> SEQUENCE: 166

```
gctccacact gacctggcct cccacttggc ccctcagcgt actgatttcc tcctcatggt    60
tcttcttcag gtaggccagc tcttccttca ggccttcgat ctgcatctcc aggtcggtcc   120
tggccagggt cagctcatcc agcaccctgc gcaggccgtt gatgtcggcc tccacgctca   180
tgcgcagagc ctgttccgtc tcaaaccttt caaaggaaat agttgcagcc aggcagagct   240
tcctcagcat ctctgnaaga cttccctacc tccccagagt tcaggagtcc ataggggggt   300
tagcttcagg ccatctaggc taggngaggg cagattctaa acccccccaac ccctacccca   360
gtcctgg                                                             367
```

<210> SEQ ID NO 167
<211> LENGTH: 508
<212> TYPE: DNA
<213> ORGANISM: human
<220> FEATURE:
<221> NAME/KEY: misc_feature
<222> LOCATION: (467)..(467)
<223> OTHER INFORMATION: n is a, c, g, or t
<400> SEQUENCE: 167

```
gaagagccaa tttaacaaac taggaagatg aaaagggaaa ttgtggccaa aactttggga    60
aaaggaggtt cttaaaatca gtgtttcccc tttgtgcact tgtagaaaaa aagaaaaac    120
cttctagagc tgatttgatg gacaatggag agagctttcc ctgtgattat aaaaaaggaa   180
gctagctgct ctacggtcat cttttgcttaa gagtatactt taacctggct tttaaagcag   240
tagtaactgc cccaccaaag gtcttaaaag ccattttttgg agcctattgc actgtgttct   300
cctactgcaa atatttttcat atgggaggat ggttttctct tcatgtaagt ccttggaatt   360
gattctaagg tgatgttctt agcacttttaa ttcctgtcaa attttttgtt ctccccttct   420
```

```
gccatcttaa atgtaagctg aaactggtct actgtgtctc tagggtnagc caaaagacaa    480
aaaaatttta ctacttttga gattgccc                                      508

<210> SEQ ID NO 168
<211> LENGTH: 584
<212> TYPE: DNA
<213> ORGANISM: human
<220> FEATURE:
<221> NAME/KEY: misc_feature
<222> LOCATION: (422)..(422)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (576)..(576)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t

<400> SEQUENCE: 168
gaaaccttgc aatatcagct agatttacac tccgggacgt tgcccaaagg taggaagaaa    60
gcagagggaa atatttcagt catcatttcc aaagtcatta tcaaaatctg tgaggaagtt   120
taatcttcca aagagtcaat gtcagacatc aggcctctgt tgcctgcttc tctcgaggca   180
ctagattagg agtcttcaat aagagactta acatgaggta tatggaagat gaggcaccga   240
gataagttca tcattaggtg tgagcactgc tcacccttgc tggcaagttc tccttaaggg   300
cctgaagcac aggtgtccaa agaaaagcgt taagtccatc ttaatagaat ctatgtggta   360
tatgatgtgg tcagcccctg gtctgtgatc agcaagaacc tacagcacag attatgccct   420
gnccacttca atgaatacct actctcctcc attctccatc acttttttgc tatcaagaac   480
tccggacttg cccatggaga agtttagaga gnactcttgt ggagagctgg tttatttctg   540
cctgtgcgac gagttcactg gccagaagga gtcagntatn aaag                   584

<210> SEQ ID NO 169
<211> LENGTH: 447
<212> TYPE: DNA
<213> ORGANISM: human

<400> SEQUENCE: 169
gcgatccagc tgccagcgca gccgccagcg ccggcacatc ccgctctggg ctttaaacgt    60 gaccccctcgc ctcgactcgc cctgccctgt gaaaatgttg gtgcttcttg ctttcatcat   120
cgccttccac atcacctctg cagccttgct gttcattgcc accgtcgaca atgcctggtg   180
ggtaggagat gagttttttg cagatgtctg gagaatatgt accaacaaca cgaattgcac   240
agtcatcaat gacagctttc aagagtactc cacgctgcag gcggtccagg ccaccatgat   300
cctctccacc attctctgct gcatcgcctt cttcatcttc gtgctccagc tcttccgcct   360
gaagcaggga gagaggtttg tcctaacctc catcatccag ctaatgtcat gtctgtgtgt   420
catgattgcg gcctccatta tacagac                                       447

<210> SEQ ID NO 170
<211> LENGTH: 495
<212> TYPE: DNA
<213> ORGANISM: human

<400> SEQUENCE: 170
```

-continued

```
ggagaggagg cagcccctc cacaccagtg gcctcgtggt tattagcaag gctgggtaat      60
gtgaaggccc aagagcagag tctgggcctc tgactctgag tccactgctc catttataac     120
cccagcctga cctgagactg tcggagaggc tgtctggggc ctttatcaaa aaagactcag     180
ccaagacaag gaggtagaga ggggactggg ggactgggag tcagagccct ggctgggttc     240
aggtcccacg tctggccagg cactgccttc tcctctctgg gcctttgttt ccttgttggt     300
cagaggagtg attgaaccag ctcatctcca aggatcctct ccactccatg tttgcaatgc     360
ttttatatgg cccagccttg taaataacca caaggtccac tccctgctcc acgaagcctt     420
aagccatagg cccaggatat ttctgaaagg aaacatgact gtgacacttc tgtccccagc     480
cctgtcctgg ttctt                                                     495

<210> SEQ ID NO 171
<211> LENGTH: 528
<212> TYPE: DNA
<213> ORGANISM: human
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t

<400> SEQUENCE: 171
gatttgattg atcaggtcct aattcctgat tctgccaaac aagttattga gctggctgga     60
aaacagcaaa ccaccttcac ggatcttgtg gcccaattag gcttggcatc tgctctgagg    120
ccagatggag aatacacttt gctggcacct gtgaataatg catttctga tgatactctc     180 agcatggatc agcgcctcct taaattaatt ctgcagaatc acatattgaa agtaaaagtt    240
ggccttaatg agctttacaa cgggcaaata ctggaaacca tcggaggcaa acagctcaga    300
gtcttcgtat atcgtacagc tgtctgcatt gaaaattcat gcatggagaa agggagtaag    360
caagggagaa acggtgcgat tcacatattc cgcgagatca tcaagccagc agagaaatcc    420
ctccatgaaa agntaaaaca agataagcgc tttagcacct tcctcagcct acttgaagct    480
gcagacttga aagagctctg acanacctgg agactggaca ttattgtg                528

<210> SEQ ID NO 172
<211> LENGTH: 529
<212> TYPE: DNA
<213> ORGANISM: human
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (509)..(509)
<223> OTHER INFORMATION: n is a, c, g, or t

<400> SEQUENCE: 172
gatagtgctt gttcggggcg ctccgctggc ttcttggaca attgcgccat gtgtgctgct     60
cggctagcgg cggcggcggc ggcccagtcg gtgtatgcct tctcggcgcg cccgctggcc    120 ggcgggagc ctgtgagcct gggctccctg cggggcaagg tactactat cgagaatgtg     180 gcgtccctct gaggcaccac ggtccgggac tacacccaga tgaacgagct gcagcggcgc    240
ctcggacccc ggggcctggt ggtgctcggc ttccgtgca accagtttgg gcatcaggag    300
aacgccaaga acgaagagat tctgaattcc ctcaagtacg tccggcctgg tggtgggttc    360
```

```
gagcccaact tcatgctctt cgagaagtgc gaggtgaacg gtgcggggc gcaccctctc    420 ttcgccttcc tgcgggaggc ctgccagctc cngcgacgac gccaccgcgc ttatgaccga    480
cccaagctca tcacctggtc tcgggggnc gcaacgatgt tgcctggaa                529
```

<210> SEQ ID NO 173  
<211> LENGTH: 533  
<212> TYPE: DNA  
<213> ORGANISM: human  
<220> FEATURE:  
<221> NAME/KEY: misc_feature  
<222> LOCATION: (411)..(411)  
<223> OTHER INFORMATION: n is a, c, g, or t

<400> SEQUENCE: 173

```
gctcagcctg cagcctctgg atggcccggt tcatctctga aatctcattc cgggtatttc    60
ggaggtcgtc cccatgcttc ccagcctggg cctggagggt ctcaaacttg gtctggtacc   120
aggcttcagc ctcagcccgg ctgcatttgg ccatctcctc atactgcgcc ttgacctcag   180
cgatgatgcc gtccaggtcc agggagcgac tgttgtccat ggacagcacc acagatgtgt   240
cggagatctg ggactgcagc tctgtcaact ccgtctcatt gagggtcctg aggaagttga   300
tctcatcatt cagggcatcc accttggcct ccagctccac cttgctcatg taggcagcat   360
ccacatcctt cttcagcacc acaaactcat tctcagcagc tgtgcggcgg ntaatttcat   420
cttcgtactt attcttgaag tcctccacca catcctgcat gctccgcagc tccgcctcca   480
ggcggccccc atccactgca gtgcctcagc tgaccccaaa gccagcaatc tgg          533
```

<210> SEQ ID NO 174  
<211> LENGTH: 521  
<212> TYPE: DNA  
<213> ORGANISM: human  
<220> FEATURE:  
<221> NAME/KEY: misc_feature  
<222> LOCATION: (490)..(490)  
<223> OTHER INFORMATION: n is a, c, g, or t

<400> SEQUENCE: 174

```
agagggggc cagaaatccc cactctagaa tgctgtagaa tgttgggaga cacccaggat    60
gtgagccagg gactttctgg aagtgtttgt tctggcccca cccgacccca ggcagtcccc   120
agctgtctgc acagtcggat ggggagggg cttgcacaga gttggagcca gaggagagag    180
ctggctcatc ccctacggta ggatggggaa acctcacaga ccacattgtc acccggcctc   240
agctctccgc cccggcgctc agagggtaac tctcacccac ctcgtccgct tctctgaacc   300
agagtgaccc aggctgcgct ccgcccgct ctcctacccc gagttggcac ggaggcccgg    360
cagccatggc ggtggaagga ggaatgaaat gtgtgaagtt cttgctctac gtcctcctgc   420
tggccttttg cgcctgtgca gtgggactga ttgccgtggg tgtcggggca cagcttgtcc   480
tgagtcagan cataatccag ggggctaccc ctggctctct g                       521
```

<210> SEQ ID NO 175  
<211> LENGTH: 487  
<212> TYPE: DNA  
<213> ORGANISM: human  
<220> FEATURE:  
<221> NAME/KEY: misc_feature  
<222> LOCATION: (458)..(458)  
<223> OTHER INFORMATION: n is a, c, g, or t

<400> SEQUENCE: 175

```
ctaggaatag cccccttttca cttctgagtc ccagaggttg cccaaggcac ccctctgaca    60
```

```
tccggcctgc ttcttctcac atgacaaaaa ctagccccca tctcaatcat ataccaaatc      120
tctccctcac taaacgtaag ccttctcctc actctctcaa tcttatccat catagcaggc      180
agttgaggtg gattaaacca aacccagcta cgcaaaatct tagcatactc ctcaattacc      240
cacataggat gaataatagc agttctaccg tacaaccccta acataaccat tcttaattta      300
actatttata ttatcctaac tactaccgca ttcctactac tcaacttaaa ctccagcacc      360
acgaccctac tactatctcg cacctgaaac aagctaacat gactaacacc cttaattcca      420
tccaccctcc tctccctagg aggctggccc cgctaacngg ttttgccca atgggccatt       480 tcgaaga                                                                487

<210> SEQ ID NO 176
<211> LENGTH: 534
<212> TYPE: DNA
<213> ORGANISM: human
<220> FEATURE:
<221> NAME/KEY: misc_feature
<222> LOCATION: (473)..(473)
<223> OTHER INFORMATION: n is a, c, g, or t

<400> SEQUENCE: 176
gggggtcata gttctccctg agtgagactt gcctgctcct ctggcccctg gtcctgtcct       60
cttctccagc atggtgtgtc tgaagctccc tggaggctcc agcttggcag cgttgacagt      120
gacactgatg gtgctgagct cccgactggc tttcgctggg gacacccgac cacgtttctt      180
ggagctgctt aagtctgagt gtcatttctt caatgggacg gagcgggtgc ggttcctgga      240
gagacacttc cataaccagg aggagtacgc gcgcttcgac agcgacgtgg gggagtaccg      300
ggcggtgagg gagctggggc ggcctgatgc cgagtactgg aacagccaga aggacctcct      360
ggagcagaag cggggccagg tggacaatta ctgcagacac aactacgggg ttggtgagag      420
cttcacagtg cagcggcgag tccatcctca ggtgactgtg tatcctgcaa ganccagccc      480
ctgcagcaca caacctcctg gtctgctctg tgaggggttc tatccaggca gcat           534

<210> SEQ ID NO 177
<211> LENGTH: 564
<212> TYPE: DNA
<213> ORGANISM: human
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t

<400> SEQUENCE: 177
gacctcatca aggcagcaga gtggatgaag gagtaagtct gcccttttgcc atactgaaca      60 gctgtggacc ccgattggtg agggctctgc atatgcctgt atgaaggaga tacaggtgtg     120
tgtgcacatg ccggtatgaa gaagacacag gcatgtgctt ctcagttttg ctaacagtgg     180
gagctcaacg gggcagaggg aggaaggtcc atgatgctca gccacatact gtagagagag     240
gcaatttaat gttaaatgac gcaccatcct ccctcccacc cttctcccag tcaactttttt     300 ttcttttttct agaactacta attatctctc aaggctgaaa aattaattgc cttaggtgga    360
gaacttaatt cctagtatcc accaaactta actccgtatc tccatatggt gtctccatat     420
```

| | |
|---|---|
| ctactgtgtg agctacttaa ctgacgccct cttcctccaa ctgaangatc gcccaacgtt | 480 |
| tttggattat agaantatta ttcctgcttt ctttctttgg gantttgaat tctttggttc | 540 |
| gttttaaaag tacccacatt ccta | 564 |

<210> SEQ ID NO 178
<211> LENGTH: 393
<212> TYPE: DNA
<213> ORGANISM: human

<400> SEQUENCE: 178

| | |
|---|---|
| gctgggactg cagctctgtc aactccgtct cattgagggt cctgaggaag ttgatctcat | 60 |
| cattcagggc atccaccttg gcctccagct ccaccttgct catgtaggca gcatccacat | 120 |
| ccttcttcag caccacaaac tcattctcag cagctgtgcg gcggttaatt tcatcttcgt | 180 |
| acttattctt gaagtcctcc accacatcct gcatgctccg cagctccgcc tccaggcggc | 240 |
| ccccatccac ctgcagtgcc tcaagctgac cccgaaggcc agcaatctgg gcctcaaaga | 300 |
| tgtctgggag gcggctgctc ttggccgact tctgctcctg cagcagcgtc cacttggtct | 360 |
| ccagcagctt gttctgctgc tccagaaccg cac | 393 |

<210> SEQ ID NO 179
<211> LENGTH: 479
<212> TYPE: DNA
<213> ORGANISM: human
<220> FEATURE:
<221> NAME/KEY: misc_feature
<222> LOCATION: (451)..(451)
<223> OTHER INFORMATION: n is a, c, g, or t

<400> SEQUENCE: 179

| | |
|---|---|
| gctcatcatt cagggcatcc accttggcct ccagctccac cttgctcatg taggcagcat | 60 |
| ccacatcctt cttcagcacc acaaactcat tctcagcagc tgtgcggcgg ttaatttcat | 120 |
| cttcgtactt attcttgaag tcctccacca catcctgcat gctccgcagc tccgcctcca | 180 |
| ggcggccccc atccacctgc agtgcctcaa gctgaccccg aaggccagca atctgggcct | 240 |
| caaagatgtc tgggaggcgg ctgctcttgg ccgacttctg ctcctgcagc agcgtccact | 300 |
| tggtctccag cagcttgttc tgctgctcca gaaccgcac cttgtcgatg aaggaggcaa | 360 |
| acttgttgtt gagggtcttg atctgctcgc tctcctcctg gcgcacccgc tggagggagg | 420 |
| ggtcggcgtc cagccgcagg gggccagcag ntctggttaa ggtgacctcg cggatgcgg | 479 |

<210> SEQ ID NO 180
<211> LENGTH: 455
<212> TYPE: DNA
<213> ORGANISM: human

<400> SEQUENCE: 180

| | |
|---|---|
| gggaatcatt ggatgtatat gaactcgatg ctaagcaggg tagatggtat gtggtacaaa | 60 |
| caaattatga ccgttggaaa catcccttct tccttgatga tcgcagaacg cctgcaaaga | 120 |
| tgtgtctgaa ccgcaccagc caagagaata tctcatttga aaccatgtat gatgtcctgt | 180 |
| caacaaaacc tgtcctcaac aagctgaccg tatacacaac cttgatagat gttaccaaag | 240 |
| gtcaattcga aacttacctg cgggactgcc ctgacccttg tataggttgg tgagcacacg | 300 |
| tctggcctac agaatgcggc ctctgagaca tgaagacacc atctccatgt gaccgaacac | 360 |
| tgcagctgtc tgaccttcca aagactaaga ctcgcggcag gttctctttg agtcaatagc | 420 |
| ttgtcttcgt ccatctgttg acaaatgaca gatct | 455 |

```
<210> SEQ ID NO 181
<211> LENGTH: 564
<212> TYPE: DNA
<213> ORGANISM: human
<220> FEATURE:
<221> NAME/KEY: misc_feature
<222> LOCATION: (443)..(443)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t

<400> SEQUENCE: 181
gatctgggac tgcagctccc ggatcttctc ttcatacagc cgcctgagga agttgatctc      60
gtcagtcagc ccttccaggc cagactccag ctctaacttg ttcatgtaag cttcatccac     120
atccttcttg atgaggacaa attgattctc catctctgta cgcttattga tctcatcctc     180
gtacttgttc ttgaagtcct ccaccagccc ctgcgtgttg ccaagctccg tctccagctt     240
cagcttctcc tggcccagag tctccagctg ccgccgcttc tcctggccca gagtctccag     300
ctgccgccta aggttgttga tgtagctctg gaacatgttg tccgtgttgc tcccagccgt     360
ctgctgctgc tgcaggaggc tccacttggt ctcctgcatc ttgttctgct gccccaggaa     420
ccgcaccttg tcgatgaagg agnaaacttg ttggtggggn tcttgatctg ctccttctcc     480
tgggtgcgca tggcctggat gttgagacca cctcctangg ggctcagcag actctggttg     540
actgtgacgc ggtgatgcct ccag                                            564

<210> SEQ ID NO 182
<211> LENGTH: 480
<212> TYPE: DNA
<213> ORGANISM: human
<220> FEATURE:
<221> NAME/KEY: misc_feature
<222> LOCATION: (430)..(430)
<223> OTHER INFORMATION: n is a, c, g, or t

<400> SEQUENCE: 182
gttgaagaat aatcctagaa aactcacaaa atgtgtgatg cttttgtagg tacctggaaa      60
cttgtctcca gtgaaaactt tgatgattat atgaaagaag taggagtggg ctttgccacc     120
aggaaagtgg ctggcatggc caaacctaac atgatcatca gtgtgaatgg ggatgtgatc     180
accattaaat ctgaaagtac cttttaaaaat actgagattt ccttcatact gggccaggaa     240
tttgacgaag tcactgcaga tgacaggaaa gtcaagagca cctaaacctt agatgggggt     300
gtcctggtac atgtgcagaa atgggatgga aaatcaacca ccataaagag aaaacgagag     360
gatgataaac tggtggtgga atgcgtcatg aaaggcgtca cttccacgag agtttatgag     420
agagcataan caagggacgt tgacctggac tgaagttcgc attgaactct acacattctg     480

<210> SEQ ID NO 183
<211> LENGTH: 577
<212> TYPE: DNA
<213> ORGANISM: human
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (536)..(536)
```

<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t

<400> SEQUENCE: 183

| | | |
|---|---|---|
| gggacaatga caagtacatc gccctggatg agtgggccgg ctgcttcggc atcaagcaga | 60 |
| aggatatcga caaggatctt gtgatctaaa tccactcctt ccacagtacc ggattctctc | 120 |
| tttaaccctc cccttcgtgt ttcccccaat gtttaaaatg tttggatggt ttgttgttct | 180 |
| gcctggagac aaggtgctaa catagattta agtgaataca ttaacggtgc taaaaatgaa | 240 |
| aattctaacc caagacatga cattcttagc tgtaacttaa ctattaaggc cttttccaca | 300 |
| cgcattaata gtcccatttt tctcttgcca tttgtagctt tgcccattgt cttattggca | 360 |
| catgggtgga cacggatctg ctgggctctg cctaaacaca cattgcagct tcaacttttc | 420 |
| tctttagtgt tctgtttgaa actaatactt accgagtcag actttgtgtt catttcattt | 480 |
| cagggtcttg gctgcctgtg ggcttcccca ggnggcctgg aggtgggcaa aggaantaac | 540 |
| agacaacgat gttgtcaagg atggtttggn aataaag | 577 |

<210> SEQ ID NO 184
<211> LENGTH: 311
<212> TYPE: DNA
<213> ORGANISM: human

<400> SEQUENCE: 184

| | | |
|---|---|---|
| gaatgtattt gccctccagg actagaggga gagcagtgtg aaatcagcaa atgcccacaa | 60 |
| ccctgtcgaa atggaggtaa atgcattggt aaaagcaaat gtaagtgttc caaaggttac | 120 |
| cagggagacc tctgttcaaa gcctgtctgc gagcctggct gtggtgcaca tggaacctgc | 180 |
| catgaaccca acaaatgcca atgtcaagaa ggttggcatg aagacactg caataaaagg | 240 |
| tacgaagcca gcctcataca tgccctgagg ccagcaggcg cccagctcag gcagcacacg | 300 |
| ccttcactta a | 311 |

<210> SEQ ID NO 185
<211> LENGTH: 475
<212> TYPE: DNA
<213> ORGANISM: human

<400> SEQUENCE: 185

| | | |
|---|---|---|
| ggaaaaacct acgtcctgcc ctcgcccggc ctctccattc gtcccccggg tagagaggtg | 60 |
| cccggctccc acccctttccc agcccagcc ctggagacag cagcccctag actactgagg | 120 |
| gacagcgaca gcatgaaggc tccgggtcgg ctcgtgctca tcatcctgtg ctccgtggtc | 180 |
| ttctctgccg tctacatcct cctgtgctgc tgggccggcc tgccctctg cctggccacc | 240 |
| tgcctggacc accacttccc cacaggctcc aggcccactg tgccgggacc cctgcacttc | 300 |
| agtggatata gcagtgtgcc agatgggaag ccgctggtcc gcgagccctg ccgcagctgt | 360 |
| gccgtggtgt ccagctccgg ccaaatgctg ggctcaggcc tgggtgctga gatcgacagt | 420 |
| gccgagtgcg tgttccgcat gaaccaggcg cccacggggg ctttagcgga tgtgg | 475 |

<210> SEQ ID NO 186
<211> LENGTH: 474
<212> TYPE: DNA
<213> ORGANISM: human

<400> SEQUENCE: 186

```
gccgggtcac accaagcact gtcaggtcag catcccctac cccagtccct ggagccagtg      60
tggctgtcac tgtgtctgcc tggggcctgg aagttgtgtc ctgcctggcc tgagacctcc     120
aggggtcaga ggggcatgca tactgtccaa gcccctgcgt ggggtgggcc tgaggacacc     180
aggggaactg ggcttggcct tggtggctat ggtggcagag accaggtgtc gaacaccagc     240
aggcacagct ccctagcctg gcccagccct tctgaggcaa cagctcaact tcctgtggtc     300
tgccctcccc acagtctgt gatcagcagc tgcccgggcc tgctctacct caacctggag     360
tcctgccgct gccttccccg gggtctgaag cgggcctacc ggggcctgga ggaagtccag     420
tggtgtctgg agcagctgct cacagcccct caccagctag cagccacaga ctgg           474

<210> SEQ ID NO 187
<211> LENGTH: 492
<212> TYPE: DNA
<213> ORGANISM: human

<400> SEQUENCE: 187
gagaagatgt gtaaacaggt atttttttaa atcaaggaaa ggctcattta aaacaggcaa      60
agttttacag agaggataca tttaataaaa ctgcgaggac atcaaagtgg taaatactgt     120
gaaataccct ttctcacaaa aaggcaaata ttgaagttgt ttatcaactt cgctagaaaa     180
aaaaaacact tggcatacaa atatttaag tgaaggagaa gtctaacgct gaactgacaa      240
tgaagggaaa ttgtttatgt gttatgaaca tccaagtctt tcttcttttt taagttgtca     300
aagaagcttc cacaaaatta gaaaggacaa cagttctgag ctgtaatttc gccttaaact     360
ctggacactc tatatgtagt gcattttaa acttgaaata tataatattc agccagctta     420
aacccataca atgtatgtac aatacaatgt acaattatgt ctcttgagca tcaatctggt     480
actgctgatc ct                                                         492

<210> SEQ ID NO 188
<211> LENGTH: 287
<212> TYPE: DNA
<213> ORGANISM: human

<400> SEQUENCE: 188
ggagcagggt gttaagttag ggtctgcctg tatttctggt ccccttggaa atgtcccctt      60
cttcagtgtc agacctcagt cccagtgtcc atatcgtgcc cagaaaagta gacattatcc     120
tgccccatcc cttccccagt gcactctgac ctagctagtg cctggtgccc agtgacctgg     180
gggagcctgg ctgcaggccc tcactggttc cctaaacctt ggtggctgtg attcaggtcc     240
ccagggggga ctcaggaagg aatatggctg agttctgtag tttcaga                   287

<210> SEQ ID NO 189
<211> LENGTH: 564
<212> TYPE: DNA
<213> ORGANISM: human
<220> FEATURE:
<221> NAME/KEY: misc_feature
<222> LOCATION: (406)..(406)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t

<400> SEQUENCE: 189
ggtggtcctg atcgacgacg acgtggagtg caccatggtt gagaagcggg tgctgacact      60
tgccgcagag aatcccttc tcacccacct catctgcacc ttccagacca aggaccacct     120
```

```
gttctttgtg atggagttcc tcaacgggg ggacctgatg taccacatcc aggacaaagg      180
ccgctttgaa ctctaccgtg ccacgtttta tgccgctgag ataatgtgtg gactgcagtt      240
tctacacagc aagggcatca tttacaggga cctcaaactg acaatgtgc tgttggaccg       300 ggatggccac atcaagattg ccgactttgg gatgtgcaaa gagaacatat cggggagag       360 ccgggccagc accttctgcg gcaccctga ctatatcgcc cctganatcc tacagggcct      420
gaagtacaca ttctctgtgg actggtggtc tttcggggtc cttctgtacg agatgctcat      480
tggccagtcc ccttccatgg tgatgatgag gatgaactct tcgagtccat ccgtgtggac      540
cgccacatna tcccgctgga tcac                                             564

<210> SEQ ID NO 190
<211> LENGTH: 549
<212> TYPE: DNA
<213> ORGANISM: human
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t

<400> SEQUENCE: 190
gtgcctggtg accagaagtt tggagtccgc tgacgtcgcc gcccagatgg cctccaggct       60
gaccctgctg accctcctgc tgctgctgct ggctggggat agagcctcct caaatccaaa      120
tgctaccagc tccagctccc aggatccaga gagtttgcaa gacagaggcg aagggaaggt      180
cgcaacaaca gttatctcca agatgctatt cgttgaaccc atcctggagg tttccagctt      240
gccgacaacc aactcaacaa ccaattcagc caccaaaata acagctaata ccactgatga      300
acccaccaca caacccacca cagagcccac cacccaaccc accatccaac ccacccnacc      360
aactacccag ctcccaacag attctcctac ccagcccact actgggtcct tctgcccagg      420
acctgttact ctctgctctg acttggagag tcattcaaca gaggccgtgt tgggggatgc      480
tttggtagat ttctccctga agctctacac gcctctcanc aatgaaaaag tggagacaac      540
atggcctttt                                                             549

<210> SEQ ID NO 191
<211> LENGTH: 487
<212> TYPE: DNA
<213> ORGANISM: human
<220> FEATURE:
<221> NAME/KEY: misc_feature
<222> LOCATION: (391)..(391)
<223> OTHER INFORMATION: n is a, c, g, or t

<400> SEQUENCE: 191
gtgggaacct aagcgtgggt ggccaacatc atatacctct tgaagaagaa ggagtcatcc       60
atcgccaact tgtctctgta gaagctccgg gtgtagattc ccttgcactg tatcatttca      120
tgctttgatt tacactcgaa ctcgggaggg aacatcctgc tgcatgacct atcagtatgg      180
tgctaatgtg tctgtggacc ctcgctctct gtctccaggc agttctctcg aatactttga      240
atgttgtgta acagttagcc actgctggtg tttatgtgaa cattcctatc aatccaaatt      300
ccctctggag tttcatgtta tgcctgttgc aggcaaatgt aaagtctaga aaataatgca      360
aatgtcacgg ctactctata tacttttgct nggtcatttt tttcccttt agtaagcatg       420 actttagatg ggaacctgtg tatcgtgaaa aaagaaaca cttttcattc ctgccccatt       480
```

```
                                                      cccaaaa                                                                 487

<210> SEQ ID NO 192
<211> LENGTH: 504
<212> TYPE: DNA
<213> ORGANISM: human
<220> FEATURE:
<221> NAME/KEY: misc_feature
<222> LOCATION: (503)..(503)
<223> OTHER INFORMATION: n is a, c, g, or t

<400> SEQUENCE: 192
gaggttctaa aaggtggtgg tactgaaaac tcgaaaatgt acctctgttt ctcatttcca      60
aaatctgagg ttgcacctgt gtttctcatt tccaaagcct gaggatgcac ctctgttcct     120
cgtctccaaa gcccgaggtc ccacttctgt tcctcatctc caaagcctga ggttgcacct     180
ctgtttctcg tctccaaagc ctgaggttgc ctgcaagtct cttgaggatt ttttggtgta     240
aacaggttga gttctggat aggtgggcat attggcagct gaatatgtgg gttttgagtg      300
tgaaatacag gttcttagct atgacccagc aatcttctac ttgttctgtg ctcttccaca     360
taaattgctt tttcttgatt gtatttcata gagcaatttc tgaggctgga aggcaggagc     420
attgtaagag acatgtcagt ggatggggac acccaagcag tgtcaagatc tcttaatgcc     480
tgaggcagat tctcacttac tgnc                                            504

<210> SEQ ID NO 193
<211> LENGTH: 507
<212> TYPE: DNA
<213> ORGANISM: human

<400> SEQUENCE: 193
gcttttcttg ttgtttaagt aattaaagtg tttaaaatgt cttcattaga tgtgacgatt      60
gtttaatgag tttgcctctg acgtgtggct ccatgggaga taggcaaagt aattaagaag     120
ttaccagaaa ttggtcggct ggggaaatgc aaaagttagc atttcagtag tgaatttctc     180
ctggaacaaa tgagcaattt ttcctctttc tcttaagtag tataccctt  tctcacttag     240 taatttaatg gtatataaag acatgtgtat aagtgagtgc atacatatga ggtatgacta     300
tagggttgtt tgtgggaatt tcttttccta acatacagaa gatcaaagtg ttcatctcac     360
cccgccctcc ttaaaggtg  tcttttggga gactatgtgc tcattgacta tagtgctgcc     420
aagtaaaaat atcttgggaa ctcttctact agaatggcct tcagggcttg gcatgttcct     480
ttggtttacc cttagagatg aaaatcc                                         507

<210> SEQ ID NO 194
<211> LENGTH: 219
<212> TYPE: DNA
<213> ORGANISM: human
<220> FEATURE:
<221> NAME/KEY: misc_feature
<222> LOCATION: (62)..(62)
<223> OTHER INFORMATION: n is a, c, g, or t

<400> SEQUENCE: 194
ggtcttggct cgtatactag gcttagggtc ccctgcatgc cctgaacccc tgggtgggtg      60
gnacagcagt gccccctgc  agccttcccc tctacacagg acatgcacac acaagtaaca     120
ttgagctgca tggacaggac ccttgagctg gcgtgtgtca attgagcgcc atgtcaggct     180
gttgtgggta tccccctggc agggtcagct aggcctgtg                            219

<210> SEQ ID NO 195
```

```
<211> LENGTH: 305
<212> TYPE: DNA
<213> ORGANISM: human
<220> FEATURE:
<221> NAME/KEY: misc_feature
<222> LOCATION: (251)..(251)
<223> OTHER INFORMATION: n is a, c, g, or t

<400> SEQUENCE: 195
ggtactggcg gcggcagggc tggcggctta ggccgcagag gtctgtgggc ctgagcccac    60
gctggactct gtccgttctg cgatgactgc tgctctggcc gtcgtcacga cgtcgggttt   120
ggaagatggg gtgcctaggt cccgtggcga agggaccggg gaagtggtct ggagcgggg    180 gcccggcgcg gcctaccaca tgttcgtggt gatggaggac ttggtggaga agctgaagct   240
gctccgctac naggaggagt tcctccggaa gagcaacctg aaggccccgt ccagacacta   300
ttttg                                                              305

<210> SEQ ID NO 196
<211> LENGTH: 4797
<212> TYPE: DNA
<213> ORGANISM: human

<400> SEQUENCE: 196
ttctgccctc gagcccaccg ggaacgaaag agaagctcta tctcccctcc aggagcccag    60
ctatgaactc cttctccaca gtaagtgca ggaaatcctt agccctggaa ctgccagcgg    120
cggtcgagcc ctgtgtgagg gaggggtgtg tggcccaggg agggctggcg gcggccagc    180 agcagaggca ggctcccagc tgtgctgtca gctcacccct gcgctcgctc ccctccggca   240
caggcgcctt cggtccagtt gccttctccc tggggctgct cctggtgttg cctgctgcct   300
tccctgcccc agtaccccca ggagaagatt ccaaagatgt agccgcccca cacagacagc   360
cactcacctc ttcagaacga attgacaaac aaattcggta catcctcgac ggcatctcag   420
ccctgagaaa ggaggtgggt aggcttggcg atggggttga agggcccggt gcgcatgcgt   480
tccccttgcc cctgcgtgtg gccggggggct gcctgcatta ggaggtcttt gctgggttct   540
agagcactgt agatttgagg ccaacggggc cgactagact gacttctgta tttatccttt   600
gctggtgtca ggaagttcct ttcctttctg gaaaatgcag aatgggtctg aaatccatgc   660 ccaccttttgg catgagctga gggttattgc ttctcagggc ttccttttcc ctttccaaaa   720
aattaggtct gtgaagctcc tttttgtccc ccgggctttg gaaggactag aaaagtgcca   780
cctgaaaggc atgttcagct tctcagagca gttgcagtac tttttggtta tgtaaactca   840
atggctagga ttcctcaaag ccattccagc taagattcat acctcagagc ccaccaaagt   900
ggcaaatcat aaataggtta aagcatctcc ccactttcaa tgcaaggtat tttggtcctg   960
tttggtagaa agaaaagaac acaggagggg agattgggag cccacactcg aattctggtt  1020
ctgccaaacc agccttgtga tcttgggtaa attccctacc acctctggac tccatcagta  1080
aaattgggcg tggactaggt gatctcatag atccttcctg ctggaacatt ctatggcttg  1140
aattatattc tcctaattat tgtcaaaatt gctgttatta agtatctact gtgtgccagg  1200
cactttaaat aaatattgtg tctaatcttc aaaacaaatt tgcaaggaag gttttttggag 1260 ataaggaaac tgagactcag gattaagtaa cacacctaaa gtcacaggtg agcttggaac  1320
tgaacccaag tgtgccccca ctccactgga atttgcttgc caggatgcca atgagttgta  1380
gcttcatttt tcttagagac tttcctggct gtggttgaac aatgaaaagg ccctctagtg  1440
gtgtttgttt tagggacact taggtgataa caattctggt attctttccc agacatgtaa  1500
```

```
caagagtaac atgtgtgaaa gcagcaaaga ggcactggca gaaaacaacc tgaaccttcc   1560
aaagatggct gaaaaagatg gatgcttcca atctggattc aatgaggtac caacttgtcg   1620
cactcacttt tcactattcc ttaggcaaaa cttctccctc ttgcatgcag tgcctgtata   1680
catatagatc caggcagcaa caaaaagtgg gtaaatgtaa agaatgttat gtaaatttca   1740
tgaggaggcc aacttcaagc tttttaaag gcagtttatt cttggacagg tatggccaga    1800
gatggtgcca ctgtggtgag attttaacaa ctgtcaaatg tttaaaactc ccacaggttt   1860
aattagttca tcctgggaaa ggtactctca gggccttttc cctctctggc tgcccctggc   1920
agggtccagg tctgccctcc ctccctgccc agctcattct ccacagtgag ataacctgca   1980
ctgtcttctg attattttat aaaaggaggt tccagcccag cattaacaag ggcaagagtg   2040
caggaagaac atcaagggg acaatcagag aaggatcccc attgccacat tctagcatct    2100
gttgggcttt ggataaaact aattacatgg ggcctctgat tgtccagtta tttaaaatgg   2160
tgctgtccaa tgtcccaaaa catgctgcct aagaggtact tgaagttctc tagaggagca   2220
gagggaaaag atgtcgaact gtggcaattt taacttttca aattgattct atctcctggc   2280
gataaccaat tttcccacca tctttcctct taggagactt gcctggtgaa atcatcact    2340
ggtcttttgg agtttgaggt atacctagag tacctccaga acagatttga gagtagtgag   2400
gaacaagcca gagctgtgca gatgagtaca aagtcctga tccagttcct gcagaaaaag    2460
gtgggtgtgt cctcattccc tcaacttggt gtggggaag acaggctcaa agacagtgtc    2520
ctggacaact cagggatgca atgccacttc caaagagaa ggctacacgt aaacaaaga    2580
gtctgagaaa tagtttctga ttgttattgt taaatctttt tttgtttgtt tggttggttg   2640
gctctcttct gcaaaggaca tcaataactg tattttaaac tatatattaa ctgaggtgga   2700
ttttaacatc aattttaat agtgcaagag atttaaaacc aaaggcgggg gggcgggcag    2760
aaaaagtgc atccaactcc agccagtgat ccacagaaac aaagaccaag gagcacaaaa    2820
tgattttaag attttagtca ttgccaagtg acattcttct cactgtggtt gtttcaattc   2880
tttttcctac cttttaccag agagttagtt cagagaaatg gtcagagact caagggtgga   2940
aagaggtacc aaaggctttg gccaccagta gctggctatt cagacagcag ggagtagact   3000
tgctggctag catgtggagg agccaaagct caataagaag gggcctagaa tgaaacccct   3060
ggtgctgatc ctgcctctgc catttctact taagccaggg tttctcatat gttaacatgc   3120
atgggaattc cctgggcatc ttcttgtggt gtggagtctg acttagcaag cctcgggtgg   3180
gtttgagggt caaatttcta ccaggcttat atccctggtg atgctgcaga attccaggac   3240
cacacttgga ggtttaaggc cttccacaag ttacttatcc catatggtgg gtctatggaa   3300
aggtgtttcc cagtcctctt tacaccaccg gatcagtggc ttttcaacag atcctaaagg   3360
gatggtgaga gggaaactgg agaaaagtat cagatttaga ggccactgaa gaacccatat   3420
taaaatgcct ttaagtatgg gctcttcatt catatactaa atatgaacta tgtgccaggc   3480
attatttcat atgacagaat acaaacaaat aagatagtga tgctggtcag gcttggtggc   3540
tcatgcctgt attccctaaa ctttgggagc ctaaggtgag aactccttga actcctaagg   3600
ccaggagttc aagaccagcc tggataacat agcaagaccc catctctaca aaaaaccaaa   3660
accaaacaaa caaaaatgat agtggtgctt ccctcaggat gcttgtggtc taatgggaga   3720
cagaacagca aagggatgat tagaagttgg ttgctgtgag ccaggcacag tgctgatata   3780
atcccagcgc tatgggaggc tgaggtgggt ggatcatttg aggccaggag tttaagacca   3840
gcctggtcaa catggtaaaa ccccatctct acttaaaaat acaaaaaagt tagccaggca   3900
```

```
tggtggcata cacctgtaac ccagctactc aggaggctga ggcacatgaa tcacttgaac      3960
ccaggaggca gaggttgctg tgcaccactg cactccagcc tgggtgacag aacgagacct      4020
tgactcaaaa aaaaaaaaaa gaagtttgtt gctatggaag ggtcctactc agagcaggca      4080
ccccagttaa tctcattcac cccacatttc acatttgaac atcatcccat agcccagagc      4140
atccctccac tgcaaaggat ttattcaaca tttaaacaat ccttttttact ttcattttcc     4200 ttcaggcaaa gaatctagat gcaataacca cccctgaccc aaccacaaat gccagcctgc      4260
tgacgaagct gcaggcacag aaccagtggc tgcaggacat gacaactcat ctcattctgc      4320
gcagctttaa ggagttcctg cagtccagcc tgagggctct tcggcaaatg tagcatgggc      4380
acctcagatt gttgttgtta atgggcattc cttcttctgg tcagaaacct gtccactggg      4440
cacagaactt atgttgttct ctatggagaa ctaaaagtat gagcgttagg acactatttt      4500
aattattttt aatttattaa tatttaaata tgtgaagctg agttaattta tgtaagtcat      4560
atttatattt ttaagaagta ccacttgaaa catttttatgt attagttttg aaataataat     4620
ggaaagtggc tatgcagttt gaatatcctt tgtttcagag ccagatcatt tcttggaaag      4680
tgtaggctta cctcaaataa atggctaact tatacatatt tttaaagaaa tatttatatt      4740
gtatttatat aatgtataaa tggttttat accaataaat ggcattttaa aaaattc         4797
```

```
<210> SEQ ID NO 197
<211> LENGTH: 7020
<212> TYPE: DNA
<213> ORGANISM: human

<400> SEQUENCE: 197
```

```
accaaacctc ttcgaggcac aaggcacaac aggctgctct gggattctct tcagccaatc        60
ttcattgctc aagtatgact ttaatcttcc ttacaactag gtgctaaggg agtctctctg       120
tctctctgcc tctttgtgtg tatgcatatt ctctctctct ctctctttct ttctctgtct       180
ctccctctcc ttccctctct gcctccctct ctcagctttt tgcaaaaatg ccaggtgtaa       240
tataatgctt atgactcggg aaatattctg ggaatggata ctgcttatct aacagctgac       300
accctaaagg ttagtgtcaa agcctctgct ccagctctcc tagccaatac attgctagtt       360
ggggtttggt ttagcaaatg cttttctcta gacccaaagg acttctcttt cacacattca       420
ttcatttact cagagatcat ttcttttgcat gactgccatg cactggatgc tgagagaaat      480
cacacatgaa cgtagccgtc atggggaagt cactcatttt ctccttttta cacaggtgtc       540
tgaagcagcc atgcagaag tacctgagct cgccagtgaa atgatggctt attacaggtc        600
agtggagacg ctgagaccag taacatgagc aggtctcctc tttcaagagt agagtgttat       660
ctgtgcttgg agaccagatt tttcccctaa attgcctctt tcagtggcaa acagggtgcc       720
aagtaaatct gatttaaaga ctactttccc attacaagtc cctccagcct gggacctgg        780 aggctatcca gatgtgttgt tgcaagggct tcctgcagag gcaaatgggg agaaaagact       840
ccaagcccac aatacaagga atccctttgc aaagtgtggc ttggagggag agggagagct       900
cagattttag ctgactctgc tgggctagag gttaggcctc aagatccaac agggagcacc       960
cagggtgccc acctgccagg cctagaatct gccttctgga ctgttctgcg catatcactg      1020
tgaaacttgc caggtgtttc aggcagcttt gagaggcagg ctgtttgcag tttcttatga      1080
acagtcaagt cttgtacaca gggaaggaaa aataaacctg tttagaagac ataattgaga      1140
catgtccctg tttttattac agtggcaatg aggatgactt gttctttgaa gctgatggcc      1200
ctaaacagat gaaggtaaga ctatgggttt aactcccaac ccaaggaagg gctctaacac      1260
```

```
agggaaagct caaagaaggg agttctgggc cactttgatg ccatggtatt ttgttttaga    1320
aagactttaa cctcttccag tgagacacag gctgcaccac ttgctgacct ggccacttgg    1380
tcatcatatc accacagtca ctcactaacg ttggtggtgg tggccacact tggtggtgac    1440
aggggaggag tagtgataat gtttcccatt tcatagtagg aagacaacca agtcttcaac    1500
ataaatttga ttatcctttt aagagatgga ttcagcctat gccaatcact tgagttaaac    1560
tctgaaacca agagatgatc ttgagaacta acatatgtct acccctttg agtagaatag    1620
ttttttgcta cctggggtga agcttataac aacaagacat agatgatata aacaaaaaga    1680
tgaattgaga cttgaaagaa aaccattcac ttgctgtttg accttgacaa gtcattttac    1740
ccgctttgga cctcatctga aaaataaagg gctgagctgg atgatctctg agattccagc    1800
atcctgcaac ctccagttct gaaatatttt cagttgtagc taagggcatt tgggcagcaa    1860
atggtcattt ttcagactca tccttacaaa gagccatgtt atattcctgc tgtcccttct    1920
gttttatatg atgctcagta gccttcctag gtggcccagc catcagccta gctaggtcag    1980
ttgtgcaggt tgggaggcag ccactttct ctggctttat tttattccag tttgtgatag    2040
cctcccctag cctcataatc cagtcctcaa tcttgttaaa aacatatttc tttagaagtt    2100
ttaagactgg cataacttgt tggctgcagc tgtgggagga gcccattggc ttgtctgcct    2160
ggcctttgcc cccattgcct cttccagcag cttggctctg ctccaggcag gaaattctct    2220
cctgctcaac tttcttttgt gcacttacag gtctctttaa ctgtctttca agcctttgaa    2280
ccattatcat gccttaaggc aacctcagtg aagccttaat acggagcttc tctgaataag    2340
aggaaagtgg taacatttca caaaaagtac tctcacagga tttgcagaat gcctatgaga    2400
cagtgttatg aaaaaggaaa aaaaagaaca gtgtagaaaa attgaatact tgctgagtga    2460
gcataggtga atggaaaatg ttatggtcat ctgcatgaaa aagcaaatca tagtgtgaca    2520
gcattaggga tacaaaaaga tatagagaag gtatacatgt atggtgtagg tggggcatgt    2580
acaaaaaaga tgaacaaagt agaaatggga tttattctaa aagaatagcc tgtaaggtgt    2640
cagaaagccc acattctagt cttgagtctg cctctaacct gctgtgtgcc cttgagtaca    2700
cacttaacct ccttgagctt cagagaggga taatcttttt atttttattttt attttatttt    2760
gttttgtttt gttttgtttt gttttatgag acagagtctc actctgttgc ccaggctgga    2820
gtgcagtggt acaatcttgg cttactgcat cctccacctc ctgagttcaa gcgattctcc    2880
ttcctcagtc tcctgaatag ctaggattac aggtgcaccc caccacaccc agctaatttt    2940
tgtattttta gtagagaagg ggtttcgcca tgttggccag gctggttttg aagtcctgac    3000
ctaaatgatt catccacctc ggcttcccaa agtgctggga ttacaggcat gagccaccac    3060
gcctggccca gagagggatg atctttagaa gctcggggatt cttcaagcc ctttcctcct    3120
ctctgagctt tctactctct gatgtcaaag catggttcct ggcaggacca cctcaccagg    3180
ctccctccct cgctctctcc gcagtgctcc ttccaggacc tggacctctg ccctctggat    3240
ggcggcatcc agctacgaat ctccgaccac cactacagca agggcttcag gcaggccgcg    3300
tcagttgttg tggccatgga caagctgagg aagatgctgg ttccctgccc acagaccttc    3360
caggagaatg acctgagcac cttctttccc ttcatctttg aagaaggtag ttagccaaga    3420
gcaggcagta gatctccact tgtgtcctct tggaagtcat caagcccag ccaactcaat    3480
tcccccagag ccaaagccct ttaaaggtag aaggcccagc ggggagacaa aacaaagaag    3540
gctggaaacc aaagcaatca tctctttagt ggaaactatt cttaaagaag atcttgatgg    3600
ctactgacat ttgcaactcc ctcactcttt ctcagggggcc tttcacttac attgtcacca    3660
```

```
gaggttcgta acctccctgt gggctagtgt tatgaccatc accatttttac ctaagtagct    3720
ctgttgctcg gccacagtga gcagtaatag acctgaagct ggaacccatg tctaatagtg    3780
tcaggtccag tgttcttagc cacccccactc ccagcttcat ccctactggt gttgtcatca    3840
gactttgacc gtatatgctc aggtgtcctc caagaaatca aattttgccg cctcgcctca    3900
cgaggcctgc ccttctgatt ttatacctaa acaacatgtg ctccacattt cagaacctat    3960
cttcttcgac acatgggata cgaggctta tgtgcacgat gcacctgtac gatcactgaa    4020
ctgcacgctc cgggactcac agcaaaaaag cttggtgatg tctggtccat atgaactgaa    4080
agctctccac ctccagggac aggatatgga gcaacaaggt aaatggaaac atcctggttt    4140
ccctgcctgg cctcctggca gcttgctaat tctccatgtt ttaaacaaag tagaaagtta    4200
atttaaggca aatgatcaac acaagtgaaa aaaatatta aaaaggaata tacaaacttt    4260
ggtcctagaa atggcacatt tgattgcact ggccagtgca tttgttaaca ggagtgtgac    4320
cctgagaaat tagacggctc aagcactccc aggaccatgt ccacccaagt ctcttgggca    4380
tagtgcaatg tcaattcttc cacaatatgg ggtcatttga tggacatggc ctaactgcct    4440
gtgggttctc tcttcctgtt gttgaggctg aaacaagagt gctggagcga taatgtgtcc    4500
atccccctcc ccagtcttcc ccccttgccc caacatccgt cccacccaat gccaggtggt    4560
tccttgtagg gaaattttac cgcccagcag gaacttatat ctctccgctg taacgggcaa    4620
aagtttcaag tgcggtgaac ccatcattag ctgtggtgat ctgcctggca tcgtgccaca    4680
gtagccaaag cctctgcaca ggagtgtggg caactaaggc tgctgacttt gaaggacagc    4740
ctcactcagg gggaagctat tgctctcag ccaggccaag aaaatcctgt ttctttggaa     4800
tcgggtagta agagtgatcc cagggcctcc aattgacact gctgtgactg aggaagatca    4860
aaatgagtgt ctctctttgg agccactttc ccagctcagc ctctcctctc ccagtttctt    4920
cccatgggct actctctgtt cctgaaacag ttctggtgcc tgatttctgg cagaagtaca    4980
gcttcacctc tttcctttcc ttccacattg atcaagttgt tccgctcctg tggatgggca    5040
cattgccagc cagtgacaca atggcttcct tccttccttc cttcagcatt taaaatgtag    5100
accctctttc attctccgtt cctactgcta tgaggctctg agaaaccctc aggcctttga    5160
ggggaaaccc taaatcaaca aaatgaccct gctattgtct gtgagaagtc aagttatcct    5220
gtgtcttagg ccaaggaacc tcactgtggg ttcccacaga ggctaccaaa ttacatgtat    5280
cctactcatg gggcctaggg gttggggtga ccctgcactg ctgtgtccct aaccacaaga    5340
ccccccttctt tcttcagtgg tgttctccat gtccttttgta caaggagaag aaagtaatga    5400
caaaatacct gtggccttgg gcctcaagga aaagaatctg tacctgtcct gcgtgttgaa    5460
agatgataag cccactctac agctggaggt aagtgaatgc tatggaatga agcccttctc    5520
agcctcctgc taccacttat tcccagacaa ccaccttctc cccgcccca tccctaggaa     5580
aagctgggaa caggtctatt tgacaatttt gcattaatgt aaataaattt aacataattt    5640
ttaactgcgt gcaaccttca atcctgctgc agaaaattaa atcatttttgc cgatgttatt    5700
atgtcctacc atagttacaa ccccaacaga ttatatattg ttagggctgc tctcatttga    5760
tagacacctt gggaaataga tgacttaaag ggtcccatta tcatgtccac tccactccca    5820
aaattaccac cactatcacc tccagctttc tcagcaaaag cttcatttcc aagttgatgt    5880
cattctagga ccataaggaa aaatacaata aaaagcccct ggaaactagg tacttcaaga    5940
agctctagct taatttttcac ccccccaaaa aaaaaaaatt ctcacctaca ttatgctcct    6000
cagcatttgg cactaagttt tagaaaagaa gaagggctct tttaataatc acacggaaag    6060
```

```
ttgggggccc agttacaact caggagtctg gctcctgatc atgtgacctg ctcgtcagtt    6120
tcctttctgg ccaacccaaa gaacatcttt cccatagcat ctttgtccct tgccccacaa    6180
aaattcttct ttctctttcg ctgcagagtg tagatcccaa aaattaccca agaagaaga     6240
tggaaaagcg atttgtcttc aacaagatag aaatcaataa caagctggaa tttgagtctg    6300
cccagttccc caactggtac atcagcacct ctcaagcaga aacatgccc gtcttcctgg     6360
gagggaccaa aggcggccag gatataactg acttcaccat gcaatttgtg tcttcctaaa    6420
gagagctgta cccagagagt cctgtgctga atgtggactc aatccctagg gctggcagaa    6480
agggaacaga aaggttttg agtacggcta tagcctggac tttcctgttg tctacaccaa     6540
tgcccaactg cctgccttag ggtagtgcta agaggatctc ctgtccatca gccaggacag    6600
tcagctctct cctttcaggg ccaatcccca gccttttgt tgagccaggc ctctctcacc     6660
tctcctactc acttaaagcc cgcctgacag aaaccacggc cacatttggt tctaagaaac    6720
cctctgtcat tcgctcccac attctgatga gcaaccgctt ccctatttat ttatttattt    6780
gtttgtttgt tttattcatt ggtctaattt attcaaaggg ggcaagaagt agcagtgtct    6840
gtaaaagagc ctagttttta atagctatgg aatcaattca atttggactg gtgtgctctc    6900
tttaaatcaa gtcctttaat taagactgaa aatatataag ctcagattat ttaaatggga    6960
atatttataa atgagcaaat atcatactgt tcaatggttc tgaaataaac ttcactgaag    7020

<210> SEQ ID NO 198
<211> LENGTH: 3159
<212> TYPE: DNA
<213> ORGANISM: human

<400> SEQUENCE: 198
ctccataagg cacaaacttt cagagacagc agagcacaca agcttctagg acaagagcca      60
ggaagaaacc accggaagga accatctcac tgtgtgtaaa catgacttcc aagctggccg     120
tggctctctt ggcagccttc ctgatttctg cagctctgtg tgaaggtaag cacatctttc     180
tgacctacag cgttttccta tgtctaaatg tgatccttag atagcaaagc tattcttgat     240
gctttggtaa caaacatcct tttttattcag aaacagaata taatcttagc agtcaattaa    300
tgttaaattg aagatttaga aaaaactata tataacactt aggaaagtat aaagtttgat     360
caatatagat attctgcttt tataatttat accatgtagc atgcatatat ttaacgtaaa    420
taagtaattt atagtatgtc ctattgagaa ccacggttac ctatattatg tattaatatt    480
gagttgagca aggtaactca gacaattcca ctccttgtag tatttcattg acaagcctca    540
gatttgtcat taattcctgt ctggtttaaa gataccctga ttatagacca ggcatgtata    600
acttatttat atatttctgt taattctttc tgaaggcaat ttctatgctg gagagtctta    660
gcttgcctac tataaataac actgtggtat cacagaggat tatgcaatat tgaccagata    720
aaaataccat gaagatgttg atattgtaca aaaagaactc taactcttta tataggaagt    780
cgttcaatgt tgtcagttat gactgttttt taaaacaaag aactaactga ggtcaagggc    840
taggagaata ttcaggaatg agttcactag aaacatgatg ccttccatag tctccaaata    900
atcatattgg aattagaaag gaagtagctg gcagagctgt gcctgttgat aaaatcaatc    960
cttaatcact ttttccccca acaggtgcag ttttgccaag gagtgctaaa gaacttagat    1020
gtcagtgcat aaagacatac tccaaacctt tccacccccaa atttatcaaa gaactgagag   1080
tgattgagag tggaccacac tgcgccaaca cagaaattat gtaagtactt taaaaaagat    1140
tagatatttt gttttagcaa acttaaaatt aaggaaggtg gaaatattta ggaaagttcc    1200
```

```
aggtgttagg attacagtag taaatgaaac aaaacaaaat aaaaatattt gtctacatga    1260
catttaaata tggtagcttc cacaactact ataaatgtta ttttggactt agactttatg    1320
cctgacttaa ggaatcatga tttgaatgca aaaactaaat attaatctga accatttctt    1380
tcttatttca gtgtaaagct ttctgatgga agagagctct gtctggaccc caaggaaaac    1440
tgggtgcaga gggttgtgga gaagtttttg aagaggtaag ttatatattt tttaatttaa    1500
atttttcatt tatcctgaga catataatcc aaagtcagcc tataaatttc tttctgttgc    1560
taaaaatcgt cattaggtat ctgccttttt ggttaaaaaa aaaggaata gcatcaatag     1620 tgagtttgtt gtactcatga ccagaaagac catacatagt ttgcccagga aattctgggt    1680
ttaagcttgt gtcctatact cttagtaaag ttctttgtca ctcccagtag tgtcctattt    1740
tagatgataa tttctttgat ctccctattt atagttgaga atatagagca tttctaacac    1800
atgaatgtca aagactatat tgacttttca agaaccctac tttccttctt attaaacata    1860
gctcatcttt atattttaa ttttatttta gggctgagaa ttcataaaaa aattcattct     1920
ctgtggtatc caagaatcag tgaagatgcc agtgaaactt caagcaaatc tacttcaaca    1980
cttcatgtat tgtgtgggtc tgttgtaggg ttgccagatg caatacaaga ttcctggtta    2040
aatttgaatt tcagtaaaca atgaatagtt tttcattgta ccatgaaata tccagaacat    2100
acttatatgt aaagtattat ttatttgaat ctacaaaaaa caacaaataa ttttaaata    2160 taaggatttt cctagatatt gcacgggaga atatacaaat agcaaaattg aggccaaggg    2220
ccaagagaat atccgaactt taatttcagg aattgaatgg gtttgctaga atgtgatatt    2280
tgaagcatca cataaaaatg atgggacaat aaattttgcc ataaagtcaa atttagctgg    2340
aaatcctgga ttttttttctg ttaaatctgg caacccctagt ctgctagcca ggatccacaa   2400
gtccttgttc cactgtgcct tggttctctcc tttatttcta agtggaaaaa gtattagcca   2460
ccatcttacc tcacagtgat gttgtgagga catgtggaag cactttaagt ttttcatca    2520 taacataaat tattttcaag tgtaacttat taacctatt attatttatg tatttattta    2580
agcatcaaat atttgtgcaa gaatttggaa aaatagaaga tgaatcattg attgaatagt    2640
tataaagatg ttatagtaaa tttatttttat tttagatatt aaatgatgtt ttattagata    2700
aatttcaatc agggttttta gattaaacaa acaaacaatt gggtacccag ttaaattttc    2760
atttcagata aacaacaaat aatttttttag tataagtaca ttattgttta tctgaaattt    2820
taattgaact aacaatccta gtttgatact cccagtcttg tcattgccag ctgtgttggt    2880
agtgctgtgt tgaattacgg aataatgagt tagaactatt aaaacagcca aaactccaca    2940
gtcaatatta gtaatttctt gctggttgaa acttgtttat tatgtacaaa tagattctta    3000
taatattatt taaatgactg catttttaaa tacaaggctt tatattttta actttaagat    3060 gttttatgt gctctccaaa ttttttttac tgtttctgat tgtatggaaa tataaaagta    3120
aatatgaaac atttaaaata taatttgttg tcaaagtaa                           3159
```

<210> SEQ ID NO 199
<211> LENGTH: 4892
<212> TYPE: DNA
<213> ORGANISM: human

<400> SEQUENCE: 199

```
acacatcagg ggcttgctct tgcaaaacca aaccacaaga cagacttgca aaagaaggca     60
tgcacagctc agcactgctc tgttgcctgg tcctcctgac tggggtgagg gccagcccag    120
gccagggcac ccagtctgag aacagctgca ccccacttccc aggcaacctg cctaacatgc    180
```

```
ttcgagatct ccgagatgcc ttcagcagag tgaagacttt ctttgtgagt atgattcctt      240 cctgtcctt  ctctcttcct gggactgcct gaactagaca ttctcctgga actataagaa     300
ccctcctcct gcgcctccac ctccatcccc aacacctatt cccccaaact taaattctta     360
agagaatcct agatcaagcc atgggtttgg tgagttaagc taagccagat gatacagtaa     420
atgtgcagga aacctgcctt ataaagtaaa tgcgttctct ctcgtgctga gaaacttata     480
agatcctgct ggcgctctat actttattgg ctaggagaag taaagaaatg tctgattcga     540
ggtgaagatg ctccccatgc cttgcagcag ggaaatttaa attgcctctg cttagagcgt     600
ttccagacct gaaagaccag tggtttaggg aagcactcta catgagggaa acctgcatta     660
gaaggagctt cttaatccct gggatctttc caagctaaac tggatgtcta cagtggggag     720
aaagaaaagc agagaacagg acatgagggg ggctcaaggc cccgaagggt tgacataggt     780
gtcccttaaa gccgaatgta gctccgcaga aagaagacca ggactgagtc aagcttctgc     840
tttcccttca aaatcggcca gattttttaa ataacttgac tctgaggagg aggacctgat     900
ttaagtgatg gtcccatcac tgttgaatcc tctgttttta aaactcccct tttgattttt     960
ttgggccaga gccaatttta tttaaaaaaa aaaatctcta aatgaaaggg catcaaaaag     1020
accgcatttc agttatttcc ccaaacctca agttcattct cctttgttc ttcctgcagc      1080 aaatgaagga tcagctggac aacttgttgt taaaggagtc cttgctggag gactttaagg     1140
tgagagcagg ggcggggtgc tgggggagtg tgcagcatga ttaagggaag ggagactctg     1200
cttcctgatt gcagggaatt gggtttgttt ccttcgcttt gaaaggaga  agtgggaaga     1260 tgttaactca gcacatccag cagccagagg gtttacaaag ggctcagtcc cttcggggag     1320
gcttctggtg aaggaggatc gctagaacca agctgtcctc ttaagctagt tgcagcagcc     1380
cctcctccca gccacctccg ccaatctctc actcaccttt ggctcctgcc cttagggtta     1440
cctgggttgc caagccttgt ctgagatgat ccagttttac ctggaggagg tgatgcccca     1500
agctgagaac caagacccag acatcaaggc gcatgtgaac tccctggggg agaacctgaa     1560
gaccctcagg ctgaggctac ggcgctgtgt aagtagcaga tcagtttttt cccttgcagc     1620
tgcccccaaa ataccatctc ctacagacca gcagggacac tcacatccac agacacagca     1680
aagacacaga ctggcagagc tagctgtaaa tgaggaaaga ctcctggagt cagatctctt     1740
gctcatttct ctttgagcag gcgttggggg tggctgctag gcatttacat gtgaaatttg     1800
caaacagctt tcctgttatt tgtgagtcat ttgtgggtta ttaactactc ccctctctct     1860
tcataaaagg agcccagagc ttcagtcagg cctccactgc ctctttgtaa ctagaccctg     1920
ggcggggagc taaggttccc aagcagagga acatcattc  acctctttta atctcaatgt     1980
tttgaaagca aagctctaag aagggcccaa ttgactgaca ggatttcccc tggcatttta     2040
gaagggacaa gggggctatt catccccagg ctagtgtcta tgagtaattc ctccaggtaa     2100
tttatttctc caactgaaat gatgcccctca ctactaatgg tttcccctgt tctgtcacca    2160
atattggaaa atcagttggt gtctatttgt aggacaaggc tatgtgaagg gtttggtccc     2220
agtagcttcc ctcctcagat gcttagaagt gttcctcggt ggctgtgact gacgggagg      2280 aacaggagag agaggcagaa aaggacaggc tgaagaatgc ctcgctcagc actgcaggag     2340
atactgtaga gttctggggg aggaaggaat cccaagacct gggttgtcat ccaagccttg     2400
caaacatctt ggagtgagtc ctggagaaat acatttaact cccagggcca tggaagcagg     2460
gctcagttct ctctgggagc tgtgaggcaa ggcatttgga taaatctggc ctcctcatga     2520
tgccaccagc ttgtccccta agtgtgatgg acatggagct ggaagccagg atcaccaaca     2580
```

```
ctttctcttt tcttccacag catcgatttc ttccctgtga aaacaagagc aaggccgtgg      2640
agcaggtgaa gaatgccttt aataaggtga gcttggatgg tggcagagag ggtctgcaga      2700
gcacaaccca tgcccactcc ccaaccccaa agcatggaag gtggtgggga ctcaataggc      2760
cccattcttc attggagaga gtgtgggaac ctgacagatg gtatgacctg ctcagccagt      2820
gaggagctgc tgccttgatt gtatttgttt tctgttaagt gtctttgggg gtttctaaat      2880
gactgctcgc tgccttttgca ggcttgcggg ttaggctggc cggccagcct gtgaacacag     2940
tgagctgcat gctggggaga gtgacaaagg aaacagaaag tacagaaagt agcttgttgg      3000
gaatctaggc tgaacccaca cgtgcaggaa gctggcacat aaatgtgcac atacaaatac      3060
acctgggggt tcagcccaga ctccccagaa ctcagaatga gcaggaagct ggattctcac      3120
ttaacctgga gttggttcaa gcccgctttc catctgccct tcgcacctgc ggaggtgcct      3180
gagaatgtca gttcccaaac gaaatggggt ttcacacttc caactgtgcg tgaactttt      3240 cagtctgatt tcccagaaac cgtgcggcct atgtcctcct cgtgggctgg ggacagacac      3300
tgcacagagt gccaacatca gggggtgtga atttctcata gtaggtcagg gcggcagggc      3360
agggcctgct cagtgtgttg gtgggagaac acagacattt aaaaggctcc ctcctctcct      3420
ctcaccgtct tgctttcgaa gcgcttcctc taatgtcttt tcatcaaact ctgcataatc      3480
atcatgtgaa tacgtgacct ttaaaattgt tgaaaaggca tcattttgaa gacagtgctt      3540
tgcaaaatga atgctcccct tgctaggggg aggcctggag gagatgaagg tcaatgcaca      3600
gcctttccca aggcagctag gcctatcctc tggtttactt cccagcgtga gggagaacaa      3660
gcaacctctg cactcaaggt catgcccatc catgagcatg agggagggga gcctatttag      3720
tccccagaaa ggattttaac tgtatgtttc ttatctctct gcacagctcc aagagaaagg      3780
catctacaaa gccatgagtg agtttgacat cttcatcaac tacatagaag cctacatgac      3840
aatgaagata cgaaactgag acatcagggt ggcgactcta tagactctag gacataaatt      3900
agaggtctcc aaaatcggat ctggggctct gggatagctg acccagcccc ttgagaaacc      3960
ttattgtacc tctcttatag aatatttatt acctctgata cctcaacccc catttctatt      4020
tatttactga gcttctctgt gaacgattta gaaagaagcc caatattata attttttca      4080 atatttatta ttttcacctg tttttaagct gtttccatag ggtgacacac tatggtattt      4140
gagtgtttta agataaatta taagttacat aagggaggaa aaaaaatgtt ctttggggag      4200
ccaacagaag cttccattcc aagcctgacc acgctttcta gctgttgagc tgtttccct      4260 gacctccctc taatttatct tgtctctggg cttggggctt cctaactgct acaaatactc      4320
ttaggaagag aaaccaggga gcccctttga tgattaattc accttccagt gtctcggagg      4380
gattccccta acctcattcc ccaaccactt cattcttgaa agctgtggcc agcttgttat      4440
ttataacaac ctaaatttgg ttctaggccg ggcgcggtgg ctcacgcctg taatcccagc      4500
actttgggag gctgaggcgg gtggatcact tgaggtcagg agttcctaac cagcctggtc      4560
aacatggtga aaccccgtct ctactaaaaa tacaaaaatt agccgggcat ggtggcgcgc      4620
acctgtaatc ccagctactt gggaggctga ggcaagagaa ttgcttgaac ccaggagatg      4680
gaagttgcag tgagctgata tcatgcccct gtactccagc ctgggtgaca gagcaagact      4740
ctgtctcaaa aataaaaat aaaaataaat ttggttctaa tagaactcag ttttaactag      4800
aatttattca attcctctgg gaatgttaca ttgtttgtct gtcttcatag cagattttaa      4860
ttttgaataa ataaatgtat cttattcaca tc                                   4892
```

<210> SEQ ID NO 200

-continued

```
<211> LENGTH: 4972
<212> TYPE: DNA
<213> ORGANISM: human

<400> SEQUENCE: 200
cacattgttc tgatcatctg aagatcagct attagaagag aaagatcagt taagtccttt      60
ggacctgatc agcttgatac aagaactact gatttcaact tctttggctt aattctctcg     120
gaaacgatga aatatacaag ttatatcttg gcttttcagc tctgcatcgt tttgggttct     180
cttggctgtt actgccagga cccatatgta aaagaagcag aaaaccttaa gaaatatttt     240
gtaagtatga cttttttaata gtacttgttt gtggttgaaa atgactgaat atcgacttgc     300
tgtagcatct ctgataggct gtcatctctt gtaggcagtc attttgagat ttggtgttat     360
tttgttaatt attgactaga tgagttcctt gactaaataa tctagatatt gttttaacct     420
tctgctcagt ttgtatagag acttaaaagg gatttatgaa ttttccaaaa gatgggcata     480
atatgggtat gaagcataat gatgttaata attttgtggt gggaactcat tcagttgtga     540
tagtcaagga gtatgcagat tgaaaaaaat gattggttat tagttttga cttctcagac      600 tctaaggtca agattagcat taaaaaggta ataggaaatg tttacaaatt aaagtcaaaa     660
aggtccttaa agctttggct taaaaaaata actgataggt gattttctcc aaaaagtgat     720
ttcaacattc tgcttctcta tctatattac ttgtgaagta ttccggaact tcgttgctca     780
ctgggatttt ggaagaatta tgattctggc taaggaatgt ttaaaaattt taagtgaatt     840
ttttgagttt cttttaaaat tttattgatg gttaatgaaa agttttaca ttttaaatat      900 ttcattattt gtttaaaact tagctgttat aattatagct gtcataataa tattcagaca     960
ttcacaattg attttattct tacaacacaa aatcaaatca cacacacaca cacacacaca    1020
cacacactcg cacatgtttg gaactatctt ttaaagctcg tataataata ccctacagga    1080
aggcacagta gatgtaatag aaacctgtac cattgggggg cagtatttta tagtggggtg    1140
gctttgctgt ttttttgtttt tgtatttttt agcctagctt gaaaatactt tctttagctt    1200
actatagttt ttgggacctt tggagtatca gctttgttga gctcatttgt gacattgcaa    1260
tttaatggtt atattgggaa ataaaaaagc taaaagaaca taatagtctt tgtctatatc    1320
tcacataagc cttttgggaa tacttattgt tagaactaag cagaagagtt gaaaaggaaa    1380
tcagtgaata ttgtcacatc tgagttcaat gaaacttgaa atatattttt aaggcaattt    1440
atgggctaat tgtaaaccaa ttttttcttt tttttttttt agaatgcagg tcattcagat    1500
gtagcggata atggaactct tttcttaggc attttgaaga attggaaaga ggtaagctga    1560
atattcccat ttggctaatt ttcctgttgc ttgctttctg atggataaat tcacatcatc    1620
ctctgtttgt gctctttcct tccaaggaga gtgacagaaa aataatgcag agccaaattg    1680 tctccttta cttcaaactt tttaaaaact ttaaagatga ccagagcatc caaaagagtg    1740
tggagaccat caaggaagac atgaatgtca agttttttcaa tagcaacaaa agaaacgag    1800 atgacttcga aaagctgact aattattcgg tgaggctatt taaattcttt ctttggtttc    1860
attgccgagg gtcttgcaaa gcatttattc tccagaaagt agacattagc tatttaacag    1920
ttgctaaagc tatgaactca actcatggct gaaactctac cttactattt ccattcgtgt    1980
ttgggtgact ttgcaaagcc agtaagagaa tcgctgaagt atgtaatgta gagaaatgct    2040
ggcattgtaa ctattgcgta aagacaggtg agttgacaaa tccagtgaag aggaagtagg    2100
tgaggaagaa gcggggagta ctgagaagca gttctctcat tgtcccttgc tcatatgatg    2160
gaaattctct tactttgaat gagaggctgt ctgtcttaat ggaaagagca gtgggaggag    2220
```

```
ctgagaagat gtgtgttctc ctcccaactc agccaccaag gaactgtgat gaatcacatg    2280
gctggctggg gctcagtttc ctcatcttaa aaggaaactg ttaggctcac tgtataagtt    2340
tgatgacctt ctttgctcca aaactctaca atgcaaagaa tagaaaatga gaatgagata    2400
gaagaaagct acagtctttg aataggtacc agggacaccc cactgcaagt ctctagccaa    2460
cctatcagat tgtactgccc aattagaagc aagaatggtt gctgtttgtt tgttttagg     2520 gaaaaataga tagaatttat accttatgaa aagattgttc tatcaactct ctatcaactt    2580
tcagaatatc tcagctggag aactccttag actcctaagt cttacctcat gaacttgtat    2640 cttaagtta tggcttctat aaacagaaag ataacgttga ggcataaaga caaatcatgt     2700
ttttcaaaat gttttctaga agacaaaggc ctctagattc ctttggggtt gactttgata    2760
taaatgggct caaatgagag ggaccagggt cttcaagcta gcatttgtgt tcttaggata    2820
tgtgctcagc tttcactatt gctgggcctg cctctcactc ctctcatgta agcccccaga    2880
aacagaaagg agagacatgg caacaggtct cctttggtta taaactagac actcagcact    2940
tgtttctaat ccagtggtgc ccctggctta ctgttcagtc ctggataagt ctcttagttt    3000
cttggtgatg atttgaacat tggaaagtaa aatctgtcac ttgcaaacac acagcttgtc    3060
gaaaattttt tctactctgc aggaactggg ccttaaaaaa atgaaaaaaa atctgtggtt    3120
tcttccttct ggaagctaca aacctcctgt ttcttgatgg gcaatcttga gtgagctcta    3180
ttaattatta ttctctttgg ctcagttgct aagctatttt atgcatgtta tgcccttga    3240 caattagtct ttagctgtaa tcccccagcc atcctcagaa atgtggtgag tagccatagt    3300
gttcccaaga ttagaaaaaa tgtaatggca gagccaagag gaaggtaaat ggtccacatt    3360
ttatgaagca tcatctaaat ggccctattg gttagagtga ggagatgcaa gtagttcaat    3420
ttgcttgcct agaaggcagg gtactggaaa agttgttgca attcttaatt ttaaacttta    3480
tatatcagta agccatatat aaatatgatt gggggtgttt atttaaaat ctattatgga    3540 aattgagaga ctgacctaat ctgggagaaa ttaaaaatta cagttttcac tcgtttgga    3600 tttggtgttt tctagggtac ctaacctaga tcagtggttc tcaaacttag gtggatgtca    3660
gaatcacctg gggagcttag tgaatgcaca gggcacagtc cttccacttc atgcacctgg    3720
atctctgagg tctttgacag gtttccggat taatctgcta tgcacaacag tgagaatcat    3780
tgacctatag ttactcattt gatgcataca ggaaagactg aagtataaag tgatataatt    3840
ggtagattga tgatagagag gtcatagaaa cagtctcatc ctcctttaga tgagaaaata    3900
gaagttcaga gaggttaagt agctggctca aggtcagaat tattgcatgc atgagattca    3960
aacccacctt tttatgctga ctccacaacc aggagtcttt tcactatata atttcaagaa    4020
ttctatagaa gtagatttaa agatatgtga tggactccac cacattatag cacaactaga    4080
aatgtaattg taattttag cttcaactgc tgaagaagta aatattgtat attaaggtaa     4140
tacggtccat tttttaaagg aatactttta ttttcactga ccatcatgac attagcagaa    4200
tatcctgatg gcttatatgc ctgaaattaa ttttgctctt ttctttcccg ataggtaact    4260
gacttgaatg tccaacgcaa agcaatacat gaactcatcc aagtgatggc tgaactgtcg    4320
ccagcagcta aaacagggaa gcgaaaaagg agtcagatgc tgtttcgagg tcgaagagca    4380
tcccagtaat ggttgtcctg cctgcaatat ttgaatttta aatctaaatc tatttattaa    4440
tatttaacat tatttatatg gggaatatat ttttagactc atcaatcaaa taagtattta    4500
taatagcaac ttttgtgtaa tgaaaatgaa tatctattaa tatatgtatt atttataatt    4560
cctatatcct gtgactgtct cacttaatcc tttgttttct gactaattag gcaaggctat    4620
```

```
gtgattacaa ggctttatct caggggccaa ctaggcagcc aacctaagca agatcccatg    4680
ggttgtgtgt ttatttcact tgatgataca atgaacactt ataagtgaag tgatactatc    4740
cagttactgc cggtttgaaa atatgcctgc aatctgagcc agtgctttaa tggcatgtca    4800
gacagaactt gaatgtgtca ggtgaccctg atgaaaacat agcatctcag gagatttcat    4860
gcctggtgct tccaaatatt gttgacaact gtgactgtac ccaaatggaa agtaactcat    4920
ttgttaaaat tatcaatatc taatatatat gaataaagtg taagttcaca ac            4972

<210> SEQ ID NO 201
<211> LENGTH: 2763
<212> TYPE: DNA
<213> ORGANISM: human

<400> SEQUENCE: 201
ctccctcagc aaggacagca gaggaccagc taagagggag agaagcaact acagacccccc     60 cctgaaaaca accctcagac gccacatccc ctgacaagct gccaggcagg ttctcttcct    120
ctcacatact gacccacggc tccaccctct ctcccctgga aaggacacca tgagcactga    180
aagcatgatc cgggacgtgg agctggccga ggaggcgctc cccaagaaga caggggggcc    240
ccagggctcc aggcggtgct tgttcctcag cctcttctcc ttcctgatcg tggcaggcgc    300
caccacgctc ttctgcctgc tgcactttgg agtgatcggc cccagagggg aagaggtgag    360
tgcctggcca gccttcatcc actctcccac ccaaggggaa atggagacgc aagagaggga    420
gagagatggg atgggtgaaa gatgtgcgct gataggagg gatggagaga aaaaacgtg      480 gagaaagacg gggatgcaga aagagatgtg gcaagagatg gggaagagag agagagaaag    540
atggagagac aggatgtctg gcacatggaa ggtgctcact aagtgtgtat ggagtgaatg    600
aatgaatgaa tgaatgaaca agcagatata aaataagat atggagacag atgtggggtg    660
tgagaagaga gatgggggaa gaaacaagtg atatgaataa agatggtgag acagaaagag    720
cgggaaatat gacagctaag gagagagatg ggggagataa ggagagaaga agataggtg     780 tctggcacac agaagacact cagggaaaga gctgttgaat gcctggaagg tgaatacaca    840
gatgaatgga gagagaaaac cagacacctc agggctaaga gcgcaggcca gacaggcagc    900
cagctgttcc tcctttaagg gtgactccct cgatgttaac cattctcctt ctccccaaca    960
gttccccagg gacctctctc taatcagccc tctggcccag gcagtcagta agtgtctcca   1020
aacctctttc ctaattctgg gtttgggttt gggggtaggg ttagtaccgg tatggaagca   1080 gtggggaaa tttaaagttt tggtcttggg ggaggatgga tggaggtgaa agtagggggg    1140
tattttctag gaagtttaag ggtctcagct ttttcttttc tctctcctct tcaggatcat   1200
cttctcgaac cccgagtgac aagcctgtag cccatgttgt aggtaagagc tctgaggatg   1260
tgtcttggaa cttggagggc taggatttgg ggattgaagc ccggctgatg gtaggcagaa   1320
cttggagaca atgtgagaag gactcgctga gctcaaggga agggtggagg aacagcacag   1380
gccttagtgg gatactcaga acgtcatggc caggtgggat gtgggatgac agacagagag   1440
gacaggaacc ggatgtgggg tgggcagagc tcgagggcca ggatgtggag agtgaaccga   1500 catgccaca ctgactctcc tctccctctc tccctccctc cagcaaaccc tcaagctgag    1560
gggcagctcc agtggctgaa ccgccgggcc aatgccctcc tggccaatgg cgtggagctg   1620
```

```
agagataacc agctggtggt gccatcagag ggcctgtacc tcatctactc ccaggtcctc    1680
ttcaagggcc aaggctgccc ctccacccat gtgctcctca cccacaccat cagccgcatc    1740
gccgtctcct accagaccaa ggtcaacctc ctctctgcca tcaagagccc ctgccagagg    1800
gagaccccag aggggctga ggccaagccc tggtatgagc ccatctatct gggaggggtc    1860
ttccagctgg agaagggtga ccgactcagc gctgagatca atcggcccga ctatctcgac    1920
tttgccgagt ctgggcaggt ctactttggg atcattgccc tgtgaggagg acgaacatcc    1980
aaccttccca aacgcctccc ctgccccaat ccctttatta ccccctcctt cagacaccct    2040
caacctcttc tggctcaaaa agagaattgg gggcttaggg tcggaaccca agcttagaac    2100
tttaagcaac aagaccacca cttcgaaacc tgggattcag gaatgtgtgg cctgcacagt    2160
gaagtgctgg caaccactaa gaattcaaac tggggcctcc agaactcact ggggcctaca    2220
gctttgatcc ctgacatctg gaatctggag accagggagc ctttggttct ggccagaatg    2280
ctgcaggact tgagaagacc tcacctagaa attgacacaa gtggacctta ggccttcctc    2340
tctccagatg tttccagact tccttgagac acggagccca gccctcccca tggagccagc    2400
tccctctatt tatgtttgca cttgtgatta tttattattt atttattatt tatttattta    2460
cagatgaatg tatttatttg ggagaccggg gtatcctggg ggacccaatg taggagctgc    2520
cttggctcag acatgttttc cgtgaaaacg gagctgaaca ataggctgtt cccatgtagc    2580
cccctggcct ctgtgccttc ttttgattat gttttttaaa atatttatct gattaagttg    2640
tctaaacaat gctgatttgg tgaccaactg tcactcattg ctgagcctct gctccccagg    2700
ggagttgtgt ctgtaatcgc cctactattc agtggcgaga aataaagttt gcttagaaaa    2760
gaa                                                                  2763

<210> SEQ ID NO 202
<211> LENGTH: 20
<212> TYPE: DNA
<213> ORGANISM: Homo Sapien

<400> SEQUENCE: 202
cacacagaca gccactcacc                                                 20

<210> SEQ ID NO 203
<211> LENGTH: 20
<212> TYPE: DNA
<213> ORGANISM: Homo Sapien

<400> SEQUENCE: 203
ttttctgcca gtgcctcttt                                                 20

<210> SEQ ID NO 204
<211> LENGTH: 20
<212> TYPE: DNA
<213> ORGANISM: Homo Sapien

<400> SEQUENCE: 204
caggaattga atgggtttgc                                                 20

<210> SEQ ID NO 205
<211> LENGTH: 20
<212> TYPE: DNA
<213> ORGANISM: Homo Sapien

<400> SEQUENCE: 205
agcagactag ggttgccaga                                                 20
```

```
<210> SEQ ID NO 206
<211> LENGTH: 20
<212> TYPE: DNA
<213> ORGANISM: Homo Sapien

<400> SEQUENCE: 206
aagcctgacc acgctttcta                                               20

<210> SEQ ID NO 207
<211> LENGTH: 20
<212> TYPE: DNA
<213> ORGANISM: Homo Sapien

<400> SEQUENCE: 207
gctccctggt ttctcttcct                                               20

<210> SEQ ID NO 208
<211> LENGTH: 20
<212> TYPE: DNA
<213> ORGANISM: Homo Sapien

<400> SEQUENCE: 208
gtccaacgca aagcaataca                                               20

<210> SEQ ID NO 209
<211> LENGTH: 20
<212> TYPE: DNA
<213> ORGANISM: Homo Sapien

<400> SEQUENCE: 209
atattgcagg caggacaacc                                               20

<210> SEQ ID NO 210
<211> LENGTH: 20
<212> TYPE: DNA
<213> ORGANISM: Homo Sapien

<400> SEQUENCE: 210
agcccatgtt gtagcaaacc                                               20

<210> SEQ ID NO 211
<211> LENGTH: 20
<212> TYPE: DNA
<213> ORGANISM: Homo Sapien

<400> SEQUENCE: 211
tgaggtacag gccctctgat                                               20

<210> SEQ ID NO 212
<211> LENGTH: 20
<212> TYPE: DNA
<213> ORGANISM: Homo Sapien

<400> SEQUENCE: 212
ggacaagctg aggaagatgc                                               20

<210> SEQ ID NO 213
<211> LENGTH: 20
<212> TYPE: DNA
<213> ORGANISM: Homo Sapien

<400> SEQUENCE: 213
tcgttatccc atgtgtcgaa                                               20
```

```
<210> SEQ ID NO 214
<211> LENGTH: 20
<212> TYPE: DNA
<213> ORGANISM: Homo Sapien

<400> SEQUENCE: 214
gtaacccgtt gaaccccatt                                               20

<210> SEQ ID NO 215
<211> LENGTH: 20
<212> TYPE: DNA
<213> ORGANISM: Homo Sapien

<400> SEQUENCE: 215
ccatccaatc ggtagtagcg                                               20
```

DIAGNOSTIC ASSAY FOR LUNG TRANSPLANT

This application claims the benefit under 35 USC §119(e) from U.S. Provisional patent application Ser. No. 60/764,382, filed Feb. 2, 2006, which is incorporated herein by reference in its entirety.

INCORPORATION OF SEQUENCE LISTING

A computer readable form of the Sequence Listing "10723-146_SequenceListing.txt" (180326 bytes), submitted via EFS-WEB and created on Jan. 23, 2012, is herein incorporated by reference.

FIELD OF THE INVENTION

The present invention relates to a diagnostic assay for determining the suitability of a lung for transplantation into a recipient.

BACKGROUND OF THE INVENTION

Currently there is no reliable biologic marker available for the assessment of donor lung grafts prior to transplantation that will predict outcome after transplantation. Donor selection is generally carried out based on a constellation of clinical findings such as: donor age, smoking history, arterial blood gas, chest radiograph findings, bronchoscopic findings and physical examination of the lung at the time of retrieval. While this is generally effective, it is an imprecise assessment and clinicians remain conservative, rejecting organs that are not clearly ideal for transplantation.[1-6]

On the other hand, the shortage of donor organs is a serious problem in any type of organ transplantation, and especially so in lung transplantation.[1,2,7,8] The insufficient supply of donor lungs causes prolonged waiting times and substantial waiting list mortality among potential recipients. Current empirical criteria for use of lungs from a potential organ donor were not based on any analysis of any data but have gained wide acceptance. This has lead to lung recovery on average from only 20% of the available pool. To overcome this shortage, some programs have resorted to the use of extended donors which are those that do not fit all of criteria outlined for "ideal" donor lungs.[2] Extension of the donor lung pool to "non-ideal" donors may eventually lead to increased risk and post-operative complications.[5] To date, we do not have reliable and reproducible markers that are able to predict the likelihood of adequate graft function or the incidence of severe ischemia-reperfusion injury. A reliable biological marker would greatly assist donor selection, would improve the safety of lung transplantation and would improve donor organ utilization.

It has been demonstrated that cytokine expression levels are associated with the degree of clinical impairment following lung transplantation.[9-10] The inventors have also reported that the protein expression level of interleukin-8 (IL-8) showed significant correlation with decreased lung graft function and the incidence of severe ischemia-reperfusion injury early after reperfusion.[11] These studies illustrated the possibility of using cytokine expression levels to aid clinical decision making to improve recipient outcome.

There is a need in the art for methods, kits and compositions for screening for, diagnosing or detecting risk of primary graft failure of a transplanted lung prior to transplantation.

SUMMARY OF THE INVENTION

The inventors have identified biomarkers that are differentially expressed in donor lungs that are or not at risk of primary graft failure. In particular, the inventors have looked at the expression levels of genes in donor lungs and have determined that certain genes are upregulated while others are downregulated. Using this information, they have formulated a gene ratio-based diagnostic test based on the expression ratios of upregulated and downregulated gene pairs.

The invention provides methods of screening for, diagnosing or detecting risk of primary graft failure of a transplanted lung prior to transplantation using RNA expression products of biomarkers of the invention. The invention also provides compositions and kits used for screening for, detecting or diagnosing risk of primary graft failure.

One aspect of the invention is a method of screening for, diagnosing or detecting risk of primary graft failure, comprising the steps:
(a) determining the level of RNA product of one or more biomarkers selected from the biomarkers of the invention in a sample from a donor lung; and
(b) comparing the level of RNA products in the sample with a control, wherein detecting differential expression of the RNA products between the donor lung and the control is indicative of risk for primary graft failure.

Another aspect of the invention, is a method of screening for, diagnosing or detecting risk of primary graft failure, comprising the steps:
(a) determining the level of RNA product of an up-regulated biomarker of the invention in a sample from a donor lung; and
(b) determining the level of RNA product of a down-regulated biomarker of the invention in the sample from the donor lung; and
(c) determining the gene ratio of the RNA products from step (a) and step (b) using equation 1, wherein equation 1 is $$\text{Gene Ratio} = \text{Log}_2 \frac{\text{Level of } RNA \text{ Product of Up-regulated Biomarker in Sample}}{\text{Level of } RNA \text{ Product of Down-regulated Biomarker in Sample}} \quad \text{(Equation 1)}$$

and, wherein a gene ratio value greater than 0 is indicative of a risk of primary graft failure.

A further aspect of the invention is a composition comprising a collection of two or more isolated nucleic acid sequences, wherein each nucleic acid sequence hybridizes to an RNA product of a biomarker of the invention or a nucleic acid sequence complementary to the RNA product, wherein the composition is used to measure the level of expression of at least two of said biomarkers. The invention also relates to specific primers and probes.

The invention also includes kits containing the nucleic acid sequences of the invention that are used to measure the RNA expression levels of products of the biomarkers of the invention.

The inventors also examined the gene expressions of key inflammatory cytokines to determine if these mRNA expression levels in the donor lung before implantation are predictive of recipient outcome after transplantation. Identifying cytokines involved in transplant rejection allows the development of a new rapid biological strategy to improve donor lung assessment, donor utilization, and recipient outcome.

The present invention provides a method of determining the suitability of a lung for transplantation by measuring cytokine levels in the lung prior to transplantation.

The inventors have shown that increased levels of IL-6, IL-8, TNF-α, IL-1β showed significant correlation with decreased lung graft function and incidents of mortality after transplantation. They have also shown that IL-10 and IFN-γ appear to be protective cytokines that decrease the chance the mortality. The inventors have further shown that the ratio of IL-6/IL-10 is a highly significant predictor of transplant outcome. Specifically, the higher the ratio of IL-6/IL-10 the worse the prognosis.

In a specific embodiment, the present invention provides a method of determining the suitability of a lung for transplantation by measuring the ratio of IL-6/IL-10 in the lung prior to transplantation.

The levels of the cytokines are preferably measured by measuring mRNA levels for the cytokine using reverse transcription PCR (RT-PCR). Preferably, the expression levels are measured using rapid real time RT-PCR as described in Example 3. The advantage of using rapid RT-PCR is that expression levels can be assessed in less than one hour which offers a significant advantage as the results are obtained quickly.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
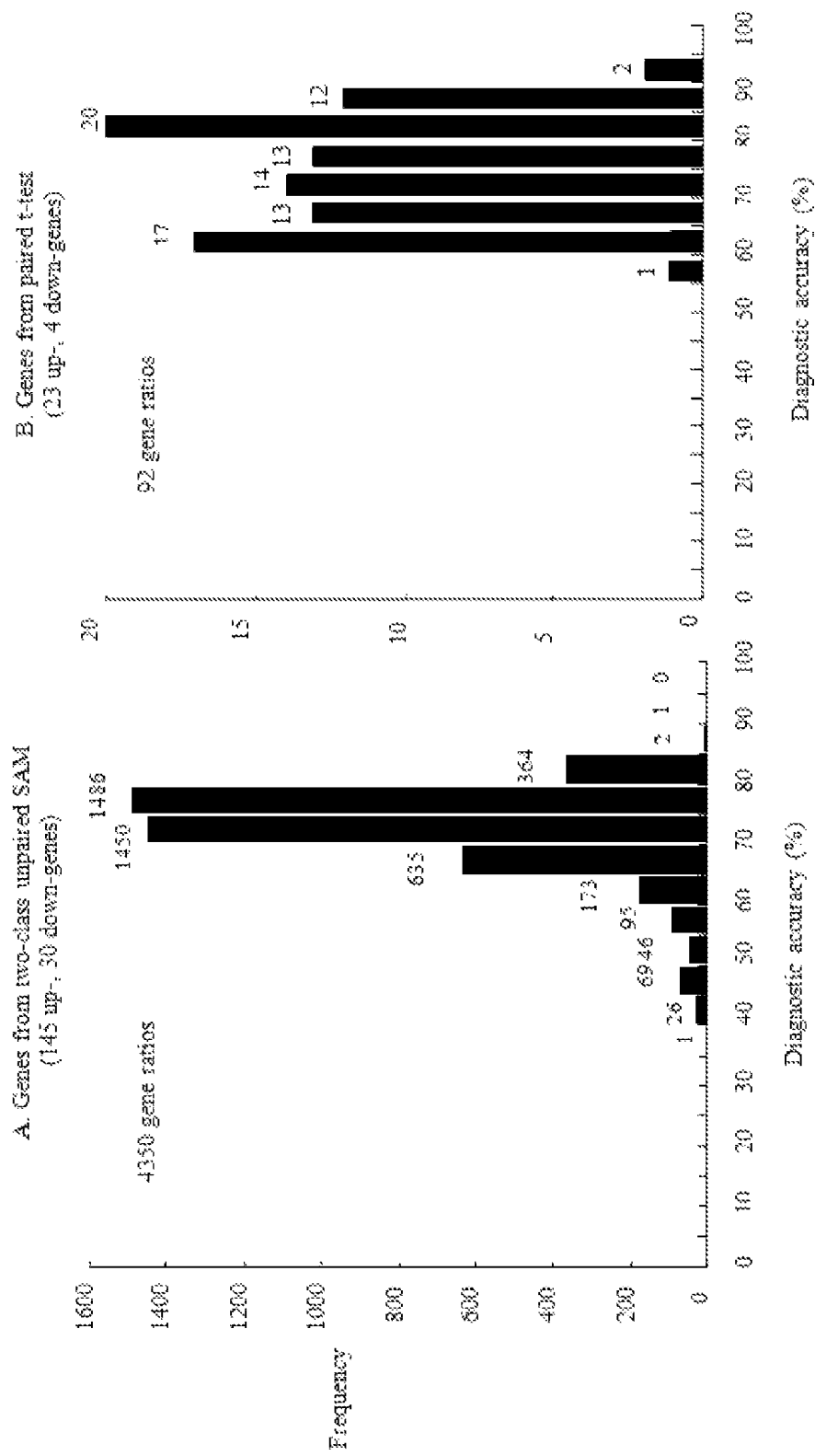
FIG. 1 is a histogram showing the diagnostic accuracy based on the gene ratio-based test of the invention. A: shows genes from the two-class unpaired SAM. B: shows genes from paired t-test.

While current donor selection based on clinical findings is generally effective, the imprecise nature of the assessment forces clinicians to remain on the conservative side. A reliable biological marker would greatly assist donor selection and would ultimately improve donor organ utilization. Accordingly, the invention discloses biomarkers that are differentially expressed in donor lungs at risk or not at risk of primary graft failure.

The term "differentially expressed" or "differential expression" as used herein refers to a difference in the level of expression of the biomarkers of the invention that can be assayed by measuring the level of expression of the products of the biomarkers of the invention, such as the difference in level of RNA expressed. The term "difference in the level of expression" refers to an increase or decrease in the measurable expression level of a given biomarker as measured by the amount of RNA in a sample as compared with the measurable expression level of a given biomarker in a second sample. The term can also refer to an increase or decrease in the measurable expression level of a given biomarker in a population of samples as compared with the measurable expression level of a biomarker in a second population of samples. In one embodiment, the differential expression can be compared using the ratio of the level of expression of a given biomarker or biomarkers as compared with the expression level of the given biomarker or biomarkers of a control, wherein the ratio is not equal to 1.0. For example, an RNA is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a biomarker is identified as being differentially expressed as between a first and second population when the p-value is less than 0.1, preferably less than 0.05, more preferably less than 0.01, even more preferably less than 0.005, the most preferably less than 0.001.

The term "risk of primary graft failure" as used herein refers to a risk of donor lung failure in the transplantation recipient. Primary graft failure is a major cause of early death after lung transplantation.

The term "biomarker" as used herein refers to a gene that is differentially expressed in donor lungs that are at risk as compared to not at risk of primary graft failure. The biomarkers of the invention include the genes as set out in Table 1, Table 2, Table 3 and/or Table 4.

One aspect of the invention is a method of screening for, diagnosing or detecting risk of primary graft failure, comprising the steps:
 (a) determining the level of RNA product of one or more biomarkers selected from the biomarkers set out in Table 1, Table 2, Table 3 and/or Table 4 in a sample from a donor lung; and
 (b) comparing the level of RNA products in the sample with a control, wherein detecting differential expression of the RNA products between the donor lung and the control is indicative of risk for primary graft failure.

In one embodiment the method comprises determining the level of RNA product of 2, 3, 4, 5, 6-10, 11-20, 21-25, 26-30, 31-50, 51-100, 101-145 or more biomarkers of the invention. In another embodiment the method comprises determining the level of RNA product of all the biomarkers of the invention.

The phrase "screening for, diagnosing or detecting risk of primary graft failure" refers to a method or process of determining if a donor lung is at risk or not at risk of primary graft failure.

The term "RNA products of the biomarkers" as used herein refers to RNA transcripts transcribed from biomarkers of the invention. The term "RNA product" of the biomarker of the invention as used herein includes mRNA transcripts, and/or specific spliced variants of mRNA.

The term "control" as used herein refers to a sample from a donor lung or a group of donor lungs which are either known as at risk of primary graft failure or not at risk.

The term "sample" as used herein refers to any fluid, cell or tissue sample from the donor lung which can be assayed for gene expression products, particularly genes differentially expressed in donor lungs at risk or not at risk of primary graft failure.

A person skilled in the art will appreciate that a number of methods can be used to measure or detect the level of RNA products of the biomarkers of the invention within a sample, including microarrays, RT-PCR (including quantitative RT-PCR and rapid RT-PCR), nuclease protection assays, in situ hybridization, in situ RT-PCR and northern blots.

Another aspect of the invention is a method of screening for, diagnosing or detecting risk of primary graft failure, comprising the steps:
(a) determining the level of RNA product of an up-regulated biomarker of the invention in a sample from a donor lung; and
(b) determining the level of RNA product of a down-regulated biomarker of the invention in the sample from the donor lung; and
(c) determining the gene ratio of the RNA products from step (a) and step (b) using equation 1, wherein equation 1 is $$\text{Gene Ratio} = \text{Log}_2 \frac{\text{Level of RNA Product of Up-regulated Biomarker in Sample}}{\text{Level of RNA Product of Down-regulated Biomarker in Sample}} \quad (\text{Equation 1})$$

and, wherein a gene ratio value greater than 0 is indicative of a risk of primary graft failure.

The level of RNA product can optionally refer to the fold change in the level of RNA product compared to a second sample where the second sample can be a control sample or a population of control samples.

The term "up-regulated biomarker" as used herein refers to a gene that is expressed at a higher amount in donor lungs that are at risk of primary graft failure as compared to not at risk of primary graft failure. The up-regulated biomarkers of the invention include the genes set out in Table 1 and/or Table 2.

The term "down-regulated biomarker" as used herein refers to a gene that is expressed at a lower amount in donor lungs that are at risk of primary graft failure as compared to not at risk of primary graft failure. The down-regulated biomarkers of the invention include the genes set out in Table 3 and/or Table 4.

The term "gene ratio" as used herein refers to the ratio of the up-regulated biomarkers of the invention as compared to the down-regulated biomarkers of the invention and can be calculated using equation (1). A gene ratio value greater than 0 is indicative of a risk of primary graft failure. A person skilled in the art will appreciate that the gene ratio can also be the ratio of the down-regulated biomarkers of the invention as compared to the up-regulated biomarkers of the invention. In one embodiment the gene ratio is calculated for 2, 3, 4, 5, 6-10, 11-15, 16-20, 21-23 or more up-regulated genes and 2, 3, 4, 5 6-10, 11-15, 16-20, 21-23 or more down-regulated genes of the invention and a composite gene ratio is used to screen for, detect or diagnose risk of primary graft failure. In another embodiment the gene ratio is calculated for 20-145 or more up-regulated biomarkers and 20-30 or more down-regulated biomarkers of the invention and a composite gene ratio is used to screen for, detect or diagnose risk of primary graft failure.

In one embodiment of the invention, the gene ratio is calculated using the ratio of up-regulated (numerator) and down-regulated (denominator) biomarker pairs set out in Table 5.

In a preferred embodiment of the invention, the methods of the invention have greater than 70%, 80%, 85%, 90%, 95% or 98% diagnostic accuracy.

Any of the methods of the invention to screen for, diagnose or detect risk of primary graft failure can be used in addition or in combination with traditional diagnostic techniques.

A further aspect of the invention is a composition comprising a collection of two or more isolated nucleic acid sequences, wherein each nucleic acid sequence hybridizes to an RNA product of a biomarker of the invention or a nucleic acid sequence complementary to the RNA product, wherein the composition is used to measure the level of expression of at least two of said biomarkers. The invention also relates to specific primers and probes.

The term "isolated nucleic acid sequence" as used herein refers to a nucleic acid substantially free of cellular material or culture medium when produced by recombinant DNA techniques, or chemical precursors, or other chemicals when chemically synthesized. An "isolated nucleic acid" is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "hybridize" refers to the sequence specific non-covalent binding interaction with a complementary nucleic acid. One aspect of the invention provides an isolated nucleotide sequence, which hybridizes to a RNA product of a biomarker of the invention or a nucleic acid sequence which is complementary to an RNA product of a biomarker of the invention. In a preferred embodiment, the hybridization is under high stringency conditions. Appropriate stringency conditions which promote hybridization are known to those skilled in the art, or can be found in Current Protocols in Molecular Biology, John Wiley & Sons, N.Y. (1989), 6.3.1 6.3.6. For example, 6.0×sodium chloride/sodium citrate (SSC) at about 45° C., followed by a wash of 2.0×SSC at 50° C. may be employed.

The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

By "at least moderately stringent hybridization conditions" it is meant that conditions are selected which promote selective hybridization between two complementary nucleic acid molecules in solution. Hybridization may occur to all or a portion of a nucleic acid sequence molecule. The hybridizing portion is typically at least 15 (e.g. 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6(Log 10[Na+])+0.41(%(G+C)−600/l), or similar equation). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5×sodium chloride/sodium citrate (SSC)/5× Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

The term "primer" as used herein refers to a nucleic acid sequence, whether occurring naturally as in a purified restriction digest or produced synthetically, which is capable of acting as a point of synthesis of when placed under conditions in which synthesis of a primer extension product, which is complementary to a nucleic acid strand is induced (e.g. in the presence of nucleotides and an inducing agent such as DNA polymerase and at a suitable temperature and pH). The primer must be sufficiently long to prime the synthesis of the desired extension product in the presence of the inducing agent. The exact length of the primer will depend upon factors, including temperature, sequences of the primer and the methods used. A primer typically contains 15-25 or more nucleotides, although it can contain less. The factors involved in determining the appropriate length of primer are readily known to one of ordinary skill in the art.

The term "probe" as used herein refers to a nucleic acid sequence that will hybridize to a nucleic acid target sequence. In one example, the probe hybridizes to an RNA product of the biomarker of the invention or a nucleic acid sequence complementary to the RNA product of the biomarker of the invention. The length of probe depends on the hybridize conditions and the sequences of the probe and nucleic acid target sequence. In one embodiment, the probe is at least 8, 10, 15, 20, 25, 50, 75, 100, 150, 200, 250, 400, 500 or more nucleotides in length.

Another aspect of the invention is a kit for screening for, diagnosing or detecting risk of primary graft failure comprising any one of the isolated nucleic acid compositions of the invention and instructions for use.

The inventors prospectively collected biopsies from 169 donor lungs before implantation. Expression levels of IL-6, IL-8, IL-10, TNF-α, IFN-γ and IL-1β were measured in a blinded fashion by real-time RT-PCR and then retrospectively compared to prospectively collected clinical data. Half of the cases were randomly selected for development of the prediction model for 30-day mortality and the remaining dataset was used to cross-validate it.

Of the 169 recipients, 17 (10.2%) died within 30 days after transplant. On univariate analysis, no donor factor was significantly associated with 30-day mortality. Univariate analysis of the development subset showed that IL-6, IL-8, TNF-α and IL-1β were risk factors for mortality and IL-10 and IFN-γ were protective factors. The inventors also analyzed the cytokine expression ratios of risk to protective cytokines. A stepwise logistic regression for 30-day mortality demonstrated that a model containing the ratio of IL-6/IL-10 was the most predictive (P=0.0013). When applied to the validation subgroup, the test of model fit was indeed significant (P=0.039). Based on the cytokine ratio, we defined high, intermediate and low risk groups with striking differences in survival (P=0.0003).

Multi-cytokine analysis of the donor lung graft with RT-PCR, preferably rapid RT-PCR, shows significant promise as a strategy to biologically evaluate the donor lung prior to implantation. Time-consuming platforms, such as protein assays are impractical for rapid measurement of a biological marker to predict outcome.

The above disclosure generally describes the present invention. A more complete understanding can be obtained by reference to the following specific examples. These examples are described solely for the purpose of illustration and are not intended to limit the scope of the invention. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present invention:

EXAMPLES

Example 1

Gene Ratio-based Test on Survival After Lung Transplant

Materials:
Patient Selection

Of 359 patients who underwent lung transplantation from Dec. 1, 1997 and Mar. 31, 2005, 28 patients who died within 30 days after lung transplantation or required Extracorporeal Membrane Support (ECMO) (Poor outcome group), and 194 patients who survived over 6 months after lung transplantation (Good outcome group) were identified. Based on the clinical course, 10 of 28 patients in the Poor outcome group (P) were selected who had clear clinical primary graft failure (PGF). Following the selection of 10 P cases, 16 patients in the Good outcome group (G) were selected as controls, matched for: recipient age (±10 years), gender, primary disease, and type of operation (single or bilateral lung transplant).

Lung Sample

Based on the aforementioned patient selection, a total of 26 snap frozen donor lung samples were used for the following experiments. Donor lung tissue samples were obtained at the end of the cold ischemic period.

Methods:
Isolation of RNA and Microarray Experiments

Total RNA was prepared from lung tissue sample using Trizol™ Reagent (Invitrogen Life Technologies, Inc. Carlsbad, Calif.). Messenger RNA was purified from total RNA by use of the RNeasy™ kit (Qiagen, Valencia, Calif.) according to the manufacturer's instructions.

Hybridized microarrays were scanned using GenePix™ 4000 (Axon Instruments), and fluorescent images were analyzed with the GenePix Pro software package. GenePix Data files (.gpr) were loaded as input and the mev files (.mev) as output with TIGR ExpressConverter (version 1.7, The Institute for Genomic Research) for further data manipulation. After data conversion, data analyses were performed with MultiExperiment Viewer (version 3.0, The Institute for Genomic Research).

Microarray Data Analysis

After Lowess normalization with Microarray Data Analysis System (version 2.19, The Institute for Genomic Research), significant changes in gene expression were determined with Significance Analysis of Microarrays (SAM) and paired Student's t-test. In SAM analysis, delta value was chosen to set the false discovery rate (FDR) at a level of 1.0%, and genes with average expression levels by at least two-fold between G and P were selected as significant ones. Two-class unpaired SAM was used for analysis. In paired Student's t-test, differences with a p value of less than 0.01 were considered significant.

Calculating Gene Expression Ratios With Selected Genes

For selected genes by SAM or Student's t-test, the raw expression data within a sample was transformed into the measurement as gene expression ratio calculated as:

$$\text{Gene Ratio} = \text{Log}_2 \frac{\text{Up-regulated Biomarker in Sample}}{\text{Down-regulated Biomarker in Sample}}$$

The gene ratios were derived by dividing the expression value of each of the selected genes up-regulated in P by the expression of those down-regulated in P. Therefore, samples with $\log_2$-transformed gene ratio values greater than 0 predict poor outcome and less than 0 predict good outcome (FIG. 1). All of the significant genes selected either by SAM or paired Student's t-test were transformed into gene ratios for any combinational pairs of genes. Ultimately, the individual gene pair ratios that predicted the group membership (i.e. good outcome or poor outcome) with the highest accuracy were chosen. Strong PGF-related signals that exist in the form of gene ratios were identified. The diagnostic accuracies of gene ratio were calculated by the following formula.

$$\text{Diagnostic accuracy}(\%) = \frac{\text{\# of correctly diagnosed samples}}{\text{\# of total samples}} \times 100$$

Initial Gene Selection

There were 4 one-to-one matched pairs and 6 one-to-two matched patient pairs (i.e. P and G). Using SAM, the 145 most significantly up-regulated genes in P (Table 1) and 30 most down-regulated genes in P compared to G (Table 3) were identified. Using paired Student's t-test, 23 most up-regulated genes (Table 2) and the 4 most down-regulated genes (Table 4) were identified.

Gene Ratio-based Test

Using the significant genes derived from two-class unpaired SAM, a total of 4350 possible expression ratios per sample was calculated. A frequency histogram of diagnostic accuracy of all 4350 gene ratios is shown in FIG. 1A. Of these gene ratios, a combination of 3 individual gene ratios predicted the outcome with high diagnostic accuracy: 92, 88, and 88%. Using the genes from paired Student's t-test, a total of 92 gene ratios (FIG. 1B) were identified. Of these, 1 gene ratio achieved diagnostic accuracy of 92%, and 10 gene ratios showed 88.5% of accuracy. The summary of the gene ratios with high diagnostic accuracy are shown in Table 5.

In summary, an expression ratio-based outcome predictor model for lung transplantations was identified. In particular, microarray data was used to identify the ratios of gene expression whose values could be used to discriminate among donor lung samples that came from patients with considerably different outcome. This is useful in a ratio-based test of key selected genes for a diagnostic strategy to more accurately assess donor lungs for transplantation.

Example 2

The inventors prospectively collected lung graft biopsies taken from 169 donor lungs at the end of the cold ischemia Oust prior to implantation) from May 1998 to April 2003 (Table 6). Biopsy samples were immediately snap-frozen in liquid nitrogen and stored at −80° C. for subsequent analysis. Biopsies of the donor lung were taken prior to implantation or excess lung tissue in donor lungs was used and reduced in size to fit the recipients. Expression levels of IL-6, IL-8, IL-10, IFN-γ, TNF-α and IL-1β mRNA were measured in a blinded fashion by quantitative real-time RT-PCR (qRT-PCR). Prospectively collected clinical data were analyzed retrospectively and then compared to cytokine expression data. The primary end-point was 30-day mortality.

To develop and validate a predictive model for death within 30 days, the 169 cases were randomly assigned to a development group (84 cases) and a validation group (85 cases) (Table 6). In the process of development of the predictive model, all cytokines and possible ratios of risk/protective cytokines were considered for inclusion in a stepwise logistic regression model.

Assessment of Conventional Donor Selection Criteria

A retrospective review of medical records was conducted for all 169 cases. In this series of patients, "extended" donors were defined as those with: a donor age of $\geq$55, $PaO_2/FiO_2$ of <300 mmHg, smoking history of $\geq$20 pack-years, abnormal chest X-ray findings, abnormal bronchoscopic findings, positive sputum gram stain, duration of mechanical ventilation of >72 hr, and ABO status of non-identical (but compatible). These were analyzed with respect to the outcome of death within 30 days.

Measurement of Gene Expression

The primers used to amplify cytokine mRNA were designed using Primer3 website developed by the Whitehead Institute for Biomedical Research. Forward and reverse primers respectively used for real-time PCR are shown in Table 9.

Total RNA was extracted from lung tissue with an RNeasy™ Mini Kit (Qiagen), according to the manufacturer's instructions. cDNA was synthesized from total RNA using MultiScribe™ Reverse Transcriptase and random hexamers from Taqman™ Reverse Transcription Reagent kit (Applied Biosystems). The reaction mix (20 μl) for reverse transcription contained 2.0 μl of 10× Taq Man RT Buffer, 4.4 μl of 25 mM magnesium chloride, 4.0 μl of 2.5 mM deoxy NTPs mixture, 1.0 μl of 50 μM random hexamers, 0.4 μl of 20 U/μl RNase inhibitor, 0.5 μl of 50 U/μl MultiScribe™ Reverse Transcriptase and 7.7 μl of RNase-free $H_2O$ with 500 ng of total RNA. The mixture was incubated at 25° C. for 10 min, at 48° C. for 30 min for reverse transcription and at 95° C. for 5 min for reverse transcriptase inactivation. Reactions were diluted to 60 μl with RNase-free water and stored at −20° C.

PCR amplification mixtures (30 μl) contained 75 ng template cDNA, 15 μof 2 x QuantiTect SYBR Green™ PCR kit (Qiagen) and 300 nM forward and reverse primers. Reactions were run on an ABI PRISM 9700HT® (Applied Biosystems). Conditions for PCR included 95° C. for 15 min, and 40 cycles of 94° C. for 15 sec (denaturation) and 60° C. for 60 sec (annealing/extension). Each assay included a standard curve of five serial dilutions and a no-template negative standard. All assays were performed in duplicate. The expression level of cytokines was normalized to the level of 18S ribosomal RNA.

Statistical Analyses

Statistical analyses were performed with JMP version 5.0 and the SAS System version 8.2 (SAS Institute). In order to compare cytokine expression levels between two groups, the Student's t-test was used with $\log_2$-transformed data of each cytokine expression level due to non-normally distributed raw values. The influence of donor clinical variables and cytokines on recipient mortality was evaluated by univariate logistic regression analysis to calculate odds ratios, 95 percent confidence intervals and area under receiver-operating characteristics (ROC) curves. Stepwise analysis was then used to select and identify the most important independent predictors of recipient outcome. Survival curves were plotted using the Kaplan-Meier method and the difference in survival among high, intermediate and low expression groups was analyzed with the Wilcoxon test. The odds ratio and 95 percent confidence interval of high risk group compared to the low risk group were calculated using logistic regression analysis. $P<0.05$ was considered statistically significant.

Results

Figure 2:
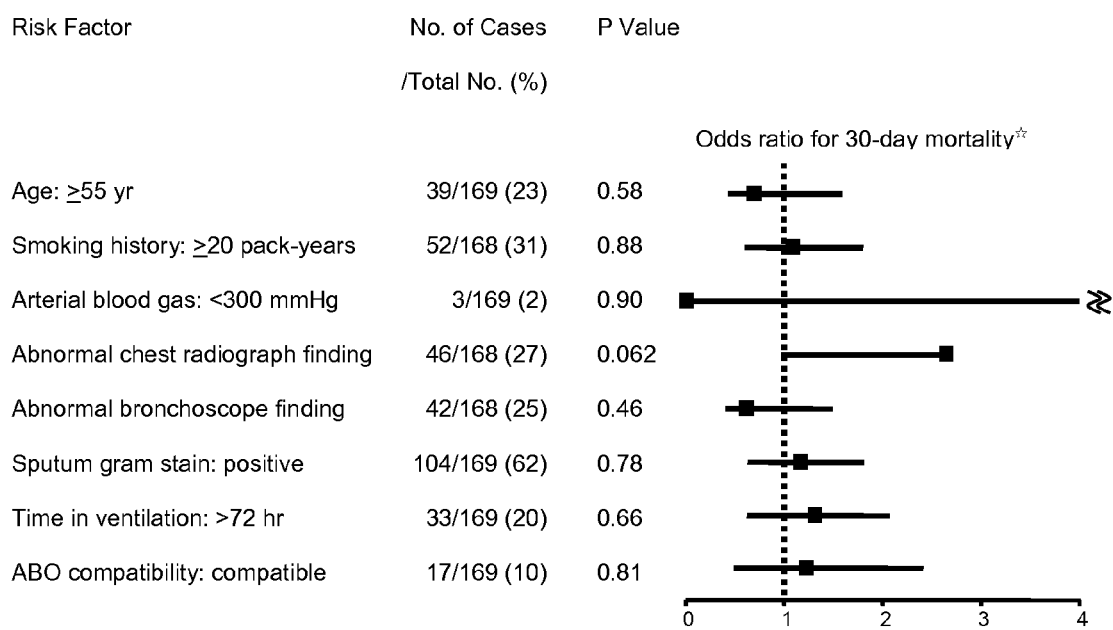
FIG. 2 shows the risk of 30-day mortality based on traditional donor selection criteria using all 169 cases. ☆ Odds ratios and 95 percent confidence intervals are shown.

Of the 169 recipients, 17 (10.2%) died within 30 days of transplant: 5 from primary graft failure, 4 from sepsis, 4 from cardiac failure, 2 from pulmonary embolism, 1 from hepatic failure and 1 from stoke. On analysis of traditional donor selection criteria, no donor factor significantly predicted 30-day mortality (FIG. 2).

The inventors compared the expression levels of cytokines between patients who died within 30 days and those who survived, with the Student's t-test using $\log_2$-transformed expression levels. Expression levels of IL-6, IL-8 and IL-1β in donor lungs were significantly higher in recipients that died within 30 days (P=0.0005, 0.048 and 0.013 respectively). TNF-α tended to be expressed at higher levels in poor prognosis cases although this difference was not statistically significant (P=0.089). Patients with poor outcomes tended to have lower levels of IL-10 and IFN-γ in donor lungs.

The inventors performed a univariate logistic regression analysis of these cytokines for 30-day mortality on the 84 cases in the development group (Table 7). IL-6 was found to be a highly significant risk factor (P=0.010, area under ROC curve: 0.679) for poor outcome and IL-1β, IL-8 and TNF-α tended to be risk factors. On the other hand, IL-10 and IFN-γ tended to be protective factors although these did not achieve significance. The value of cytokine expression ratios of "risk" cytokines to "protective" cytokines were then investigated in order to improve the prediction model. A stepwise logistic regression for 30-day mortality using individual cytokine expressions and possible combinations of the cytokine ratios demonstrated that a model containing ratio of IL-6/IL-10 was the most predictive (P=0.0013, area under ROC curve: 0.735) (Table 7). When applied to the validation group, the test of model fit was also significant (P=0.039, area under ROC curve: 0.716).

Figure 3A:
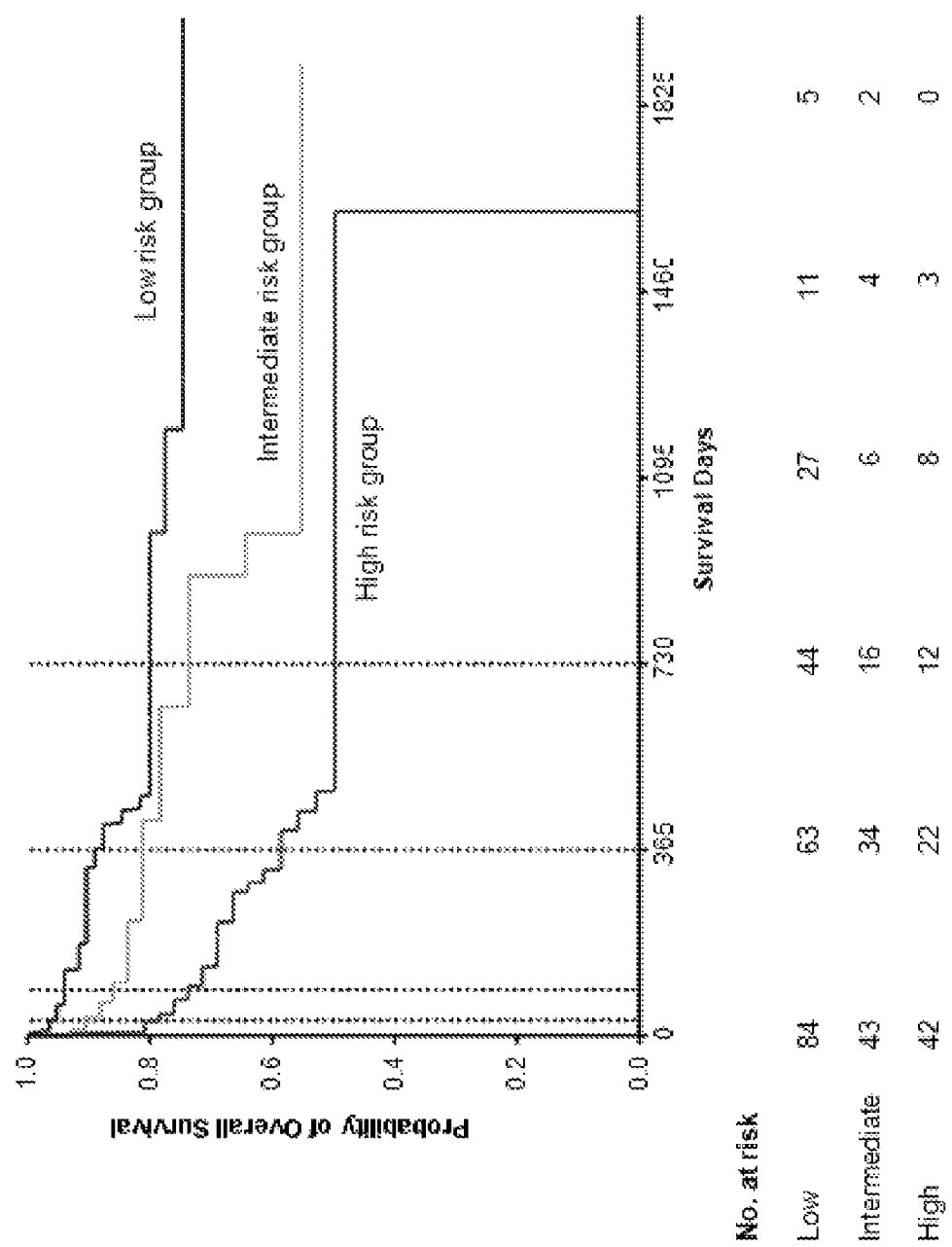
FIG. 3 shows a Kaplan-Meier survival analysis of three risk groups defined by the expression ratio of IL-6/IL-10. The vertical dotted lines mark the time points of 30 days, 90 days, 1 year and 2 years respectively. A: The high risk group was defined as cases which fell into the highest quartile expression ratios of IL-6/IL-10, the intermediate risk group as those that fell in the second highest quartile and the low risk group as the remaining half of cases with lowest expression ratio. (Wilcoxon test, P=0.0004, chi-square: 15.9). B: The high risk group was defined as cases which fell into the highest 5% expression ratios of IL-6/IL-10, the intermediate risk group as those that fell in the following 45% and the low risk group as remaining half of cases with lowest expression ratio. (Wilcoxon test, P=0.0016, chi-square: 12.8)

In order to examine the influence of the cytokine ratio on long term survival, the inventors defined two cut-off points based on the expression ratio of IL-6/IL-10 at the highest quartile, second highest quartile, and the lower half to classify high, intermediate, and low risk groups (Table 10 and 11). These groups had striking differences in both early and late survival (FIG. 3A, P=0.0004, chi-square: 15.9). Sensitivity, specificity and positive predictive values of the high risk group for 30-day mortality of recipients were: 52.9%, 78.3% and 21.4% respectively. Odds ratio for 30-day mortality of the high risk group compared with the low risk group as the reference was 5.5 (95 percent confidence interval: 1.7-21.3) (Table 8). Alternatively, if the high risk group is defined as the highest 5% (instead of 25%) IL-6/IL-10 ratio, to more stringently predict poor outcome lung, 8 patients fell in this group (Table 12 and 13). Sensitivity, specificity and positive predictive values of this high risk group for 30-day mortality were: 23.5%, 97.4% and 50.0% respectively. In this case, odds ratio for death within 30 days of the high risk group compared to the low risk group was 20.0 (95 percent confidence interval: 3.6-121.3) (Table 8).

Discussion

According to the Registry of the International Society for Heart and Lung Transplantation, the 1-year survival after lung transplantation is approximately 70%, and most of the deaths occur within 30 days of transplantation. The main cause of death in this period is primary graft dysfunction. In this study, 17 recipients died within 30 days, five died from primary graft failure and the remaining 12 died from other causes. With current donor selection processes, recipient deaths from primary graft failure are quite rare (5/169) although we cannot exclude the possibility of impact of graft dysfunction on other causes of early death. The inventors thus chose 30-day mortality from all causes as the primary end point of the study. To attribute primary graft dysfunction, we carefully considered initial blood gases, chest X-ray, microbiological studies and other criteria. Cause of death was assigned prospectively by the clinical team, independent of the current analysis. Despite the clinical importance of primary graft failure, prediction with current donor selection criteria is imprecise (FIG. 2) and some criteria such as chest radiograph evaluation are subjective. Here we demonstrate that a logistic regression model containing IL-6/IL-10 measured in the donor lung before implantation significantly predicts recipient 30-day mortality.

Figure 3B:
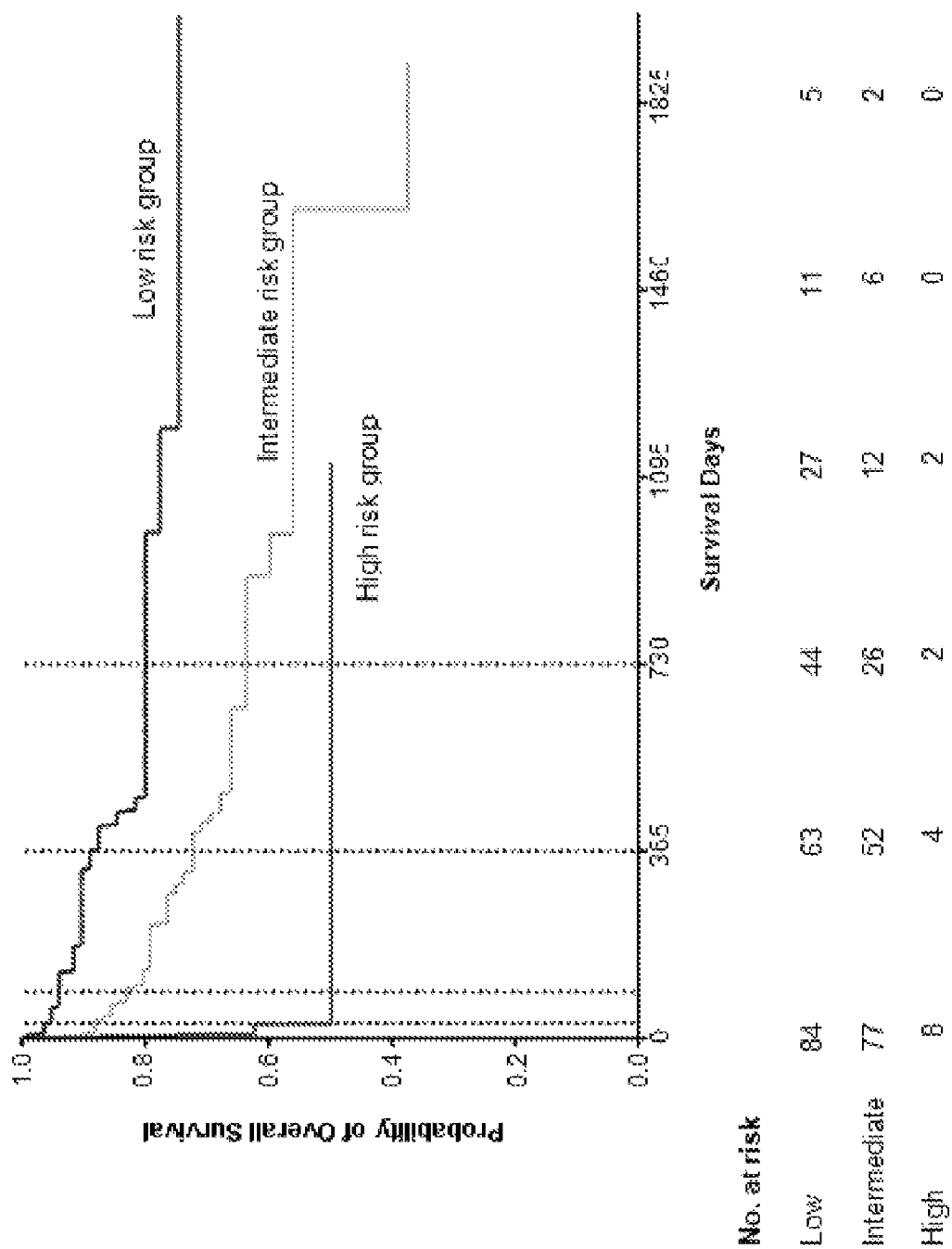

In this example, the inventors demonstrated that the degree of inflammation in donor lung biopsies examined by the expression level of multiple cytokines was predictive of recipient short-term (Table 8) and also long-term (FIG. 3) outcomes. This evidence supports a novel concept that the inflammatory situation in the donor lung not only has an impact in inducing ischemia-reperfusion injury, but also leads to lung dysfunction in the sub-acute and chronic phase.

The inventors measured mRNA expression levels of key cytokines potentially involved in ischemia-reperfusion injury during lung transplantation. Fisher and coworkers have demonstrated that high mRNA expression levels of IL-8 in donor bronchoalveolar lavage are associated with early graft failure after lung transplantation. The inventors have previously reported on the relationship between protein expression level of IL-8 in lung biopsies taken two hours after reperfusion and graft function after transplantation. In the current study, although IL-8 tended to be high in non-survivors, the level of IL-6 turned out to be far more significant as a marker to predict recipient outcome on univariate individual cytokine analysis. To investigate which cytokine or cytokine ratio is the best marker for the prediction of recipient outcome, we selected cases for modeling and cross-validation by randomly assigning them to either a development or validation dataset, particularly because there might have been changes and improvements in the outcome of transplantation over the study period due to refinement of surgical techniques and postoperative management as well as donor selection and management. In the development group, the regression model demonstrated that IL-6/IL10 was the best marker to predict recipient 30-day mortality. The validation group successfully validated this finding.

From the differential distribution of expression patterns of all the cytokines examined, it became evident that analysis of the balance of multiple cytokines is ultimately likely to be more informative than examining a single cytokine alone.

Cytokines have been classified as "pro" and "anti" inflammatory according to their roles in inflammatory responses. The inventors' initial plan to examine the ratios was based on the biological plausibility of the concept and the fact that the balance between pro- and anti-inflammatory cytokines has been used to predict patient outcome in other forms of lung injury. Indeed, IL-10, which is thought to be an anti-inflammatory cytokine, had relatively lower levels in the poor prognosis cases in our study. This was generally in the opposite direction to the expression pattern of IL-8 which is an inflammatory chemokine and TNF-α and IL-1β which are typical pro-inflammatory cytokines. These pro-inflammatory cytokines had relatively higher expression levels in cases with poor recipient outcomes. Interestingly, IFN-γ had an expression pattern quite similar to IL-10 although IFN-γ is generally felt to be a pro-inflammatory cytokine. As discussed above, IL-6 had significantly higher expression levels in the cases of death within 30 days and this expression pattern was quite similar to that of IL-8. In fact, there is some controversy as to the role of IL-6 in inflammation, more recently it has been thought to have some anti-inflammatory properties. Regardless of what is currently known about the specific functions of each cytokine examined, based on the univariate logistic regression analysis, we investigated the cytokine ratios of the "risk" cytokines (IL-6, IL-8, TNF-α and IL-1β) for poor recipient outcome to "protective" cytokines (IL-10 and IFN-γ). The stepwise regression model demonstrated that IL-6/IL-10 was the best overall marker to predict the recipient early outcome. A similar strategy to predict patient outcomes has been utilized in previous reports, showing the ratio of the most up-regulated genes to the most down-regulated genes.

Furthermore, the measurement of mRNA ratios has an inherent advantage in the methodology of quantification on most PCR platforms. In this study, we normalized the cytokine expression levels to levels of 18S ribosomal RNA. The measurement of the cytokine expression ratio using the same amount of cDNA transcribed from total RNA ultimately obviates the need for endogenous controls, which are eventually cancelled out in the process of calculating a ratio. This strategy improves accuracy in measurement for actual clinical use.

In conclusion, this example study demonstrates that the cytokine ratio of IL-6 to IL-10 in the donor lung before implantation significantly predicts recipient early mortality and late survival after lung transplantation. Quantitative RT-PCR multiple cytokine analysis of the donor lungs shows significant promise as a strategy to biologically evaluate the donor lung before implantation.

Example 3

As described in Example 2, the cytokine ratio of IL-6 to IL-10 in the donor lung before implantation significantly predicts early mortality and late survival in lung transplant recipients. The use of rapid RT-PCR assay provides the expression level in less than 1 hr from tissues-bringing this technology into the realm of clinical utility.

IL-6 and IL-10 gene expression levels were measured by quantitative multiplex rapid RT-PCR using SmartCycler II® (Cephied) in total RNA isolated from donor lung biopsies (n=52) taken at the end of the cold ischemic period (just prior to implantation). Samples for analysis were selected to represent a spectrum of outcomes after lung transplantation.

Total time to finish the rapid RT-PCR process with 40 cycles took 23 minutes compared to 2 hr 15 min with conventional real-time PCR using PRISM 7900HT® (Applied Biosystem). Correlation of measurements between conventional real-time RT-PCR and rapid RT-PCR was excellent (Spearman correlation coefficient: 0.93, $P<0.0001$). The five patients that died from primary graft failure and the ten patients that died within 30 days were successfully identified as a group of higher expression ratios of IL-6/IL-10 using both PCR techniques.

Multiple cytokine analysis of the donor lungs with quantitative multiplex rapid RT-PCR correlates well with the conventional RT-PCR analysis of donor lungs, showing significant promise as a strategy to biologically evaluate donor lungs prior to implantation.

Example 4

Ratio Based Test for Detecting Risk of Primary Graft Failure

A sample is obtained from a transplant lung. The sample may be obtained pre-implantation. The sample is assayed for gene expression products of one or more gene pairs listed in Table 5 and/or Table 7. The expression level of each gene (RNA product) is compared to a second sample and/or a standard curve. The second sample may be a control sample. The fold change (increase or decrease) in the expression level of the gene product is determined. The gene ratio is calculated using Equation 1 using the fold change in the expression level of the RNA product. A gene ratio value of greater than 0 is indicative of a risk of primary graft failure whereas a gene ratio value of less than 0 predicts a good outcome. One or more gene ratios can be used to detect the risk of primary graft failure. Alternatively a gene chip comprising one or more of the gene pairs listed in Table 5 and/or Table 7 can be used to assay a sample for the level of gene expression products. Further, one or more gene ratios can be used in combination with standard clinical findings.

While the present invention has been described with reference to what are presently considered to be preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

REFERENCES

1. Orens J B, Boehler A, de Perrot M, et al. A review of lung transplant donor acceptability criteria. J Heart Lung Transplant 2003; 22:1183-200.
2. de Perrot M, Liu M, Waddell T K, Keshavjee S. Ischemia-reperfusion-induced lung injury. Am J Respir Crit Care Med 2003; 167:490-511.
3. Ware L B, Wang Y, Fang X, et al. Assessment of lungs rejected for transplantation and implications for donor selection. Lancet 2002; 360:619-20.
4. Smits J M, Mertens B J, Van Houwelingen H C, Haverich A, Persijn G G, Laufer G. Predictors of lung transplant survival in eurotransplant. Am J Transplant 2003; 3:1400-6.
5. Pierre A F, Sekine Y, Hutcheon M A, Waddell T K, Keshavjee S H. Marginal donor lungs: a reassessment. J Thorac Cardiovasc Surg 2002; 123:421-7; discussion, 427-8.

6. Meyer D M, Bennett L E, Novick R J, Hosenpud J D. Effect of donor age and ischemic time on intermediate survival and morbidity after lung transplantation. Chest 2000; 118:1255-62.
7. Whiting D, Banerji A, Ross D, et al. Liberalization of donor criteria in lung transplantation. Am Surg 2003; 69:909-12.
8. Trulock E P, Edwards L B, Taylor D O, et al. The Registry of the International Society for Heart and Lung Transplantation: Twentieth Official adult lung and heart-lung transplant report—2003. J Heart Lung Transplant 2003; 22:625-35.
9. Fisher A J, Donnelly S C, Hirani N, et al. Elevated levels of interleukin-8 in donor lungs is associated with early graft failure after lung transplantation. Am J Respir Crit Care Med 2001; 163:259-65.
10. Mal H, Dehoux M, Sleiman C, et al. Early release of proinflammatory cytokines after lung transplantation. Chest 1998; 113:645-51.
11. De Perrot M, Sekine Y, Fischer S, et al. Interleukin-8 release during early reperfusion predicts graft function in human lung transplantation. Am J Respir Crit Care Med 2002; 165:211-5.
12. Rozen S, Skaletsky H. Primer3 on the WWW for general users and for biologist programmers. Methods Mol Biol 2000; 132:365-86.
13. Park W Y, Goodman R B, Steinberg K P, et al. Cytokine balance in the lungs of patients with acute respiratory distress syndrome. Am J Respir Crit Care Med 2001; 164:1896-903.
14. Armstrong L, Millar A B. Relative production of tumour necrosis factor alpha and interleukin 10 in adult respiratory distress syndrome. Thorax 1997; 52:442-6.
15. Boehler A. The role of interleukin-10 in lung transplantation. Transpl Immunol 2002; 9:121-4.
16. Fischer S, Liu M, Maclean A A, et al. In vivo donor adenoviral-mediated transtracheal transfection of human IL-10 (HIL-10) gene ameliorates ischemia-reperfusion (IR) injury and enhances transplanted lung function. J Heart Lung Transplant 2001; 20:152-153.
17. Luster A D. Chemokines—chemotactic cytokines that mediate inflammation. N Engl J Med 1998; 338:436-45.
18. Bhatia M, Moochhala S. Role of inflammatory mediators in the pathophysiology of acute respiratory distress syndrome. J Pathol 2004; 202:145-56.
19. Munford R S, Pugin J. Normal responses to injury prevent systemic inflammation and can be immunosuppressive. Am J Respir Crit Care Med 2001; 163:316-21.
20. Xing Z, Gauldie J, Cox G, et al. IL-6 is an antiinflammatory cytokine required for controlling local or systemic acute inflammatory responses. J Clin Invest 1998; 101:311-20.
21. Gordon G J, Richards W G, Sugarbaker D J, Jaklitsch M T, Bueno R. A prognostic test for adenocarcinoma of the lung from gene expression profiling data. Cancer Epidemiol Biomarkers Prev 2003; 12:905-10.
22. Gordon G J, Jensen R V, Hsiao L L, et al. Using gene expression ratios to predict outcome among patients with mesothelioma. J Natl Cancer Inst 2003; 95:598-605.
23. Lossos I S, Czerwinski D K, Alizadeh A A, et al. Prediction of survival in diffuse large-B-cell lymphoma based on the expression of six genes. N Engl J Med 2004; 350:1828-37.
24. Bustin S A. Quantification of mRNA using real-time reverse transcription PCR (RT-PCR): trends and problems. J Mol Endocrinol 2002; 29:23-39.
25. Raja S, Luketich J D, Kelly L A, Gooding W E, Finkelstein S D, Godfrey T E. Rapid, quantitative reverse transcriptase-polymerase chain reaction: application to intraoperative molecular detection of occult metastases in esophageal cancer. J Thorac Cardiovasc Surg 2002; 123:475-82; discussion 482-3.
26. Yoshioka S, Fujiwara Y, Sugita Y, et al. Real-time rapid reverse transcriptase-polymerase chain reaction for intraoperative diagnosis of lymph node micrometastasis: clinical application for cervical lymph node dissection in esophageal cancers. Surgery 2002; 13:34-40.

TABLE 1

Up-regulated genes, SAM, False discovery rate = 1%, Fold change >2

| Unigene ID | GenBank Accession No. | Fold change | q-value (%) | gene name | biologic process |
|---|---|---|---|---|---|
| Hs.546472 | N28396 | 2.0628278 | 0.927213 | Not found | Not found |
| Hs.446240 | R10799 | 2.0815518 | 0.927213 | Protein kinase C binding protein 1 | Cell cycle |
| No unigene ID | W31733 | 2.4518194 | 0.921071 | Not found | Not found |
| Hs.531810 | AA011361 | 3.1125834 | 0.89853895 | CDNA FLJ44597 fis, clone BLADE2006043 | Unknown |
| No unigene ID | R77593 | 2.096404 | 0.8680789 | Not found | Not found |
| Hs.435773 | T75076 | 2.0076187 | 0.8556372 | Interferon responsive gene 15 | Unknown |
| No unigene ID | H05203 | 2.0270216 | 0.8556372 | Not found | Not found |
| Hs.445711 | W79001 | 2.1802237 | 0.8270397 | Phosphodiesterase 3B | Signal transduction |
| No unigene ID | R96585 | 2.3431523 | 0.8270397 | Not found | Not found |
| Hs.128824 | R81942 | 2.6194618 | 0.8228826 | Oligophrenin 1 | Neurogenesis |
| Hs.475319 | T86042 | 2.1779134 | 0.4878951 | Leucine rich repeat interacting protein 2 | LRR domain binding |
| Hs.371001 | T84174 | 2.0473 | 0.8228826 | Eukaryotic translation initiation factor 3 | Protein biosynthesis |
| Hs.471514 | AA011354 | 2.2281156 | 0.81526273 | Hypothetical protein DKFZp547E052 | Unknown |
| No unigene ID | R22088 | 2.0841908 | 0.80211014 | Not found | Not found |
| No unigene ID | R06168 | 2.1107354 | 0.72517955 | Not found | Not found |
| No unigene ID | R52015 | 2.6535978 | 0.70619524 | Not found | Not found |
| Hs.350756 | R28601 | 2.1723046 | 0.68537354 | Staufen | Double-stranded RNA binding |
| Hs.401232 | AA056540 | 2.488967 | 0.68537354 | Similar to FLJ46489 protein | Unknown |
| No unigene ID | T70366 | 2.2288318 | 0.4878951 | Not found | Not found |
| Hs.369921 | H71281 | 2.1109807 | 0.68537354 | Vav 2 | G-protein coupled receptor protein signaling pathway |
| Hs.75231 | R16207 | 2.117395 | 0.68726254 | AKR7 family pseudogene | Unknown |
| Hs.502777 | T66987 | 2.0586095 | 0.727441 | DKFZP564J0863 protein | GTPase activity |
| Hs.324746 | AL564444 | 2.4749284 | 0.727441 | Alpha-2-HS-glycoprotein | Acute-phase response |
| unigene ID | H91761 | 2.3955183 | 0.6917268 | Not found | Not found |
| No unigene ID | AA035085 | 2.012221 | 0.6626049 | Not found | Not found |

TABLE 1-continued

Up-regulated genes, SAM, False discovery rate = 1%, Fold change >2

| Unigene ID | GenBank Accession No. | Fold change | q-value (%) | gene name | biologic process |
|---|---|---|---|---|---|
| No unigene ID | W79023 | 2.047425 | 0.6626049 | Not found | Not found |
| No unigene ID | N49632 | 2.0929964 | 0.674845 | Not found | Not found |
| Hs.532855 | AW957880 | 2.1319568 | 0.674845 | Similar to GNGT1 protein | Unknown |
| No unigene ID | R00201 | 2.2268727 | 0.6301978 | Not found | Not found |
| Hs.245931 | R07141 | 2.2721915 | 0.63752574 | Transcribed locus | Unknown |
| No unigene ID | AA058399 | 2.0456698 | 0.63752574 | Not found | Not found |
| Hs.132406 | AI982772 | 2.229496 | 0.63752574 | CDNA clone IMAGE: 4821555 | Unknown |
| No unigene ID | BM837817 | 3.9263227 | 0.62067074 | Not found | Not found |
| No unigene ID | R08416 | 2.074499 | 0.62067074 | Not found | Not found |
| Hs.444329 | H70001 | 2.2020042 | 0.63037956 | Glypican 6 | Integral to plasma membrane |
| Hs.162868 | H85606 | 2.1423795 | 0.63037956 | D4, zinc and double PHD fingers, family 3 | Zinc ion binding |
| No unigene ID | BG259125 | 2.7876737 | 0.61551964 | Not found | Not found |
| No unigene ID | R00423 | 2.429745 | 0.6169138 | Not found | Not found |
| No unigene ID | R24553 | 2.3528388 | 0.6169138 | Not found | Not found |
| Hs.387623 | T70868 | 2.0004554 | 0.6254132 | Zinc finger protein 169 | Regulation of transcription |
| Hs.162795 | H66270 | 2.0877182 | 0.5868042 | Hydroxysteroid (17-beta) dehydrogenase 2 | Estrogen biosynthesis |
| Hs.118118 | H37857 | 3.002699 | 0.5874858 | Tetraspanin 5 | Integral to membrane |
| No unigene ID | N72782 | 2.7524335 | 0.5874858 | Not found | Not found |
| Hs.418167 | BG569034 | 2.3697793 | 0.56254894 | Albumin | Transport |
| No unigene ID | N98311 | 4.168716 | 0.56254894 | Not found | Not found |
| No unigene ID | T98711 | 2.3060555 | 0.57929975 | Not found | Not found |
| No unigene ID | R59802 | 2.5892458 | 0.56390774 | Not found | Not found |
| No unigene ID | R13862 | 2.434447 | 0.5432861 | Not found | Not found |
| No unigene ID | H70162 | 2.2606342 | 0.5432861 | Not found | Not found |
| Hs.33102 | H84844 | 2.0878623 | 0.5432861 | Transcription factor AP-2 beta | Transcription/Neurogenesis |
| No unigene ID | AA156894 | 2.8526988 | 0.5432861 | Not found | Not found |
| No unigene ID | T70440 | 3.1960385 | 0.55269367 | Not found | Not found |
| No unigene ID | W78898 | 2.2309666 | 0.55269367 | Not found | Not found |
| Hs.292026 | T93745 | 2.0013666 | 0.55269367 | Eukaryotic translation initiation factor 4E member 2 | Regulation of translation |
| No unigene ID | T97966 | 2.8168771 | 0.55269367 | Not found | Not found |
| Hs.464912 | R10278 | 2.0815163 | 0.49659443 | Hypothetical protein FLJ10656 | Kinase activity |
| No unigene ID | AA115234 | 2.07074 | 0.49659443 | Not found | Not found |
| Hs.269775 | T99914 | 2.027747 | 0.4878951 | Mitogen-activated protein kinase kinase kinase 7 interacting protein 2 | Kinase activity |
| Hs.480281 | H23906 | 3.9246862 | 0.4878951 | Glutamate receptor, ionotropic, delta 2 | Ionotropic glutamate receptor activity |
| Hs.509872 | R06568 | 2.0822086 | 0.4878951 | Regulator of G-protein signalling 6 | Intracellular signaling cascade |
| No unigene ID | T80447 | 2.1294878 | 0.4878951 | Not found | Not found |
| No unigene ID | H06620 | 2.9205055 | 0.4878951 | Not found | Not found |
| Hs.268803 | H41577 | 2.4567091 | 0.4878951 | Transcribed locus, moderately similar to XP_227769.2 PREDICTED: similar to Ac1147 [*Rattus norvegicus*] | Unknown |
| No unigene ID | H18883 | 2.6860607 | 0.4878951 | Not found | Not found |
| No unigene ID | N31017 | 2.0115986 | 0.4878951 | Not found | Not found |
| No unigene ID | R19723 | 3.008867 | 0.4878951 | Not found | Not found |
| Hs.415842 | T81862 | 2.3415568 | 0.4878951 | RNA binding motif protein 18 | Nucleic acid binding |
| No unigene ID | H11931 | 2.3123705 | 0.4878951 | Not found | Not found |
| No unigene ID | R66260 | 3.1314466 | 0.4878951 | Not found | Not found |
| Hs.37883 | T81115 | 2.077185 | 0.4878951 | Chromosome 18 open reading frame 21 | Unknown |
| Hs.152774 | N31674 | 2.1845584 | 0.4878951 | Amyotrophic lateral sclerosis 2 (juvenile) chromosome region, candidate 3 | Neurotransmitter transport |
| Hs.492445 | T83285 | 2.0564806 | 0.4878951 | E3 ubiquitin protein ligase, HECT domain containing 1 | Cell proliferation |
| Hs.36959 | H68949 | 2.2708952 | 0.4878951 | Testis expressed sequence 27 | Zinc ion binding/DNA binding |
| No unigene ID | W94979 | 2.0376163 | 0.4878951 | Not found | Not found |
| Hs.513528 | T82120 | 4.296239 | 0.4878951 | Integrin, alpha D | Cell-cell adhesion |
| Hs.199877 | T75384 | 2.0949662 | 0.4878951 | Copine IV | Membrane trafficking |
| Hs.306291 | R10306 | 2.3038788 | 0.4878951 | Hypothetical protein FLJ11712 | Unknown |
| No unigene ID | W87872 | 2.5315652 | 0.4878951 | Not found | Not found |
| Hs.517493 | R11878 | 2.2182956 | 0.4878951 | Adrenergic, beta, receptor kinase 2 | Signal transducer activity |
| Hs.126980 | T78275 | 4.708315 | 0.4878951 | Phosphodiesterase 7B | Hydrolase activity |
| Hs.497148 | T81523 | 2.699405 | 0.4878951 | Ral guanine nucleotide dissociation stimulator-like 1 | Small GTPase mediated signal transduction |
| Hs.293736 | AA632632 | 2.0348194 | 0.4878951 | Activity-dependent neuroprotector | Regulation of transcription, DNA-dependent |
| No unigene ID | R10608 | 3.6907012 | 0.4878951 | Not found | Not found |
| Hs.479669 | R81620 | 2.055763 | 0.4878951 | TXK tyrosine kinase | Intracellular signaling cascade |
| No unigene ID | R52939 | 2.063447 | 0.4878951 | Not found | Not found |
| No unigene ID | R51938 | 2.9239776 | 0.4878951 | Not found | Not found |
| No unigene ID | R06804 | 2.4831643 | 0.4878951 | Not found | Not found |
| No unigene ID | N59038 | 2.1996408 | 0.4878951 | Not found | Not found |
| Hs.444783 | H50042 | 2.397501 | 0.4878951 | Neuregulin 3 | Regulation of cell growth |
| No unigene ID | N45540 | 2.3523571 | 0.4878951 | Not found | Not found |

TABLE 1-continued

Up-regulated genes, SAM, False discovery rate = 1%, Fold change >2

| Unigene ID | GenBank Accession No. | Fold change | q-value (%) | gene name | biologic process |
|---|---|---|---|---|---|
| Hs.194152 | T87019 | 2.0250046 | 0.4878951 | Clone IMAGE: 115304 mRNA sequence | Unknown |
| Hs.479783 | N27994 | 2.1842208 | 0.4878951 | KIAA1211 protein | Unknown |
| Hs.175955 | H18766 | 2.4879994 | 0.4878951 | Splicing factor YT521-B | Nuclear mRNA splicing, via spliceosome |
| No unigene ID | T80910 | 2.4734857 | 0.4878951 | Not found | Not found |
| Hs.401316 | AA046598 | 2.3045576 | 0.4878951 | Insulin-like growth factor binding protein 1 | Regulation of cell growth |
| Hs.20225 | AA046677 | 2.2553365 | 0.4878951 | Similar to SRR1-like protein | Secretory pathway |
| No unigene ID | H03900 | 3.4048715 | 0.4878951 | Not found | Not found |
| Hs.120950 | W86154 | 2.1993437 | 0.4878951 | Rhesus blood group-associated glycoprotein | Ammonium transport |
| No unigene ID | AA147249 | 3.4492323 | 0.4878951 | Not found | Not found |
| Hs.388297 | N72811 | 2.050307 | 0.4878951 | Chromosome 8 open reading frame 36 | Unknown |
| No unigene ID | AA128257 | 3.9887383 | 0.4878951 | Not found | Not found |
| No unigene ID | N30932 | 2.2592316 | 0.4878951 | Not found | Not found |
| Hs.483784 | T80689 | 3.1107001 | 0.4878951 | SH3 domain and tetratricopeptide repeats 2 | Binding |
| Hs.298987 | R21229 | 2.72001 | 0.4878951 | Transcribed locus, weakly similar to NP_997354.1 FLJ42200 protein [Homo sapiens] | Unknown |
| No unigene ID | BM715797 | 2.0446796 | 0.4878951 | Not found | Not found |
| No unigene ID | W86352 | 2.202049 | 0.4878951 | Not found | Not found |
| Hs.530871 | R24757 | 2.2490969 | 0.4878951 | Phosphodiesterase 1B | Calmodulin binding |
| Hs.133331 | T84382 | 2.021822 | 0.4878951 | WD repeat domain 31 | Unknown |
| Hs.518410 | H15520 | 2.294862 | 0.4878951 | Hypothetical gene supported by AK055127; BC053586; BC067863 | Unknown |
| Hs.99145 | BF743825 | 2.1901598 | 0.4878951 | KIAA1423 | Unknown |
| Hs.420541 | AA147516 | 2.1157634 | 0.4878951 | KIAA1202 protein | Unknown |
| Hs.314338 | R22345 | 2.8156624 | 0.4878951 | Bromodomain and WD repeat domain containing 1 | Cell cycle |
| No unigene ID | AA150082 | 2.1328883 | 0.4878951 | Not found | Not found |
| No unigene ID | N31177 | 2.243383 | 0.4878951 | Not found | Not found |
| Hs.31824 | H21441 | 2.0047147 | 0.4878951 | Similar to nonhistone chromosomal protein HMG-1 - pig | Unknown |
| Hs.380774 | W92173 | 2.0128908 | 0.4878951 | DEAD (Asp-Glu-Ala-Asp) box polypeptide 3, X-linked | Hydrolase activity |
| Hs.444314 | H84096 | 2.0893362 | 0.4878951 | Family with sequence similarity 59, member A | Sugar binding |
| No unigene ID | AA036919 | 2.7386656 | 0.4878951 | Not found | Not found |
| No unigene ID | N56650 | 3.3542788 | 0.4878951 | Not found | Not found |
| Hs.548299 | T70759 | 2.108763 | 0.4878951 | Transcribed locus, moderately similar to XP_518970.1 PREDICTED: similar to GLCCI1 protein [Pan troglodytes] | Unknown |
| Hs.443417 | T84865 | 2.1337478 | 0.4878951 | Misshapen-like kinase 1 (zebrafish) | ATP binding |
| Hs.167805 | W78878 | 2.8728664 | 0.4878951 | Enhancer of polycomb homolog 1 (Drosophila) | Regulation of cell growth |
| Hs.527348 | N73140 | 2.2147274 | 0.4878951 | A kinase (PRKA) anchor protein (yotiao) 9 | Signal transduction |
| No unigene ID | T82272 | 2.1303232 | 0.4878951 | Not found | Not found |
| Hs.381126 | AA150120 | 2.8500893 | 0.4878951 | Ribosomal protein S14 | Protein biosynthesis |
| Hs.458609 | AA148531 | 2.2203183 | 0.4878951 | Dipeptidylpeptidase 8 | Immune response |
| Hs.461030 | BF448352 | 3.1407957 | 0.4878951 | Hypothetical protein MGC11335 | Electron transport |
| Hs.12967 | N53777 | 2.4134035 | 0.4878951 | Spectrin repeat containing, nuclear envelope 1 | Nuclear organization and biogenesis |
| Hs.437941 | W93001 | 2.2315507 | 0.4878951 | Chromosome 14 open reading frame 106 | DNA binding |
| Hs.509909 | R00922 | 2.0990689 | 0.4878951 | Numb homolog (Drosophila) | Integral to plasma membrane |
| Hs.201925 | AA039425 | 2.037318 | 0.4878951 | CDNA FLJ13446 fis, clone PLACE1002968 | Unknown |
| Hs.12409 | R20699 | 2.175671 | 0.4878951 | Somatostatin | Hormone activity |
| unigene ID | H30091 | 2.39441 | 0.4878951 | Not found | Not found |
| No unigene ID | H02110 | 2.39607 | 0.4878951 | Not found | Not found |
| No unigene ID | T99420 | 2.6466935 | 0.4878951 | Not found | Not found |
| No unigene ID | R31008 | 2.0042918 | 0.4878951 | Not found | Not found |
| Hs.503743 | R21289 | 3.4334402 | 0.4878951 | Glutamate receptor, ionotrophic, AMPA 4 | Glutamate-gated ion channel activity |
| Hs.494648 | T75327 | 2.1501877 | 0.4878951 | Testis expressed sequence 10 | Mitotic chromosome condensation |
| Hs.128959 | N79346 | 2.1184788 | 0.4878951 | PCF11 | MRNA cleavage |
| Hs.49787 | R23053 | 3.3270438 | 0.4878951 | Latent transforming growth factor beta binding protein 1 | Unknown |
| No unigene ID | AA12879 | 2.1876402 | 0.4878951 | Not found | Not found |

TABLE 2

Up-regulated genes, Paired t-test, p < 0.01

| Unigene ID | GenBank Accession No. | Gene name | Function |
|---|---|---|---|
| Hs.388715 | H58023 | Hypothetical protein LOC285733 | Unknown |
| No Unigene ID | T95563 | cDNA clone IMAGE: 120597 | Unknown |
| Hs.59486 | R25303 | Hydroxysteroid dehydrogenase like 2 | Germ line formation |
| Hs.102788 | AU135696 | Mannosidase, alpha, class 1A, member 1 | Calcium ion binding, Carbohydrate metabolism |
| Hs.533683 | R93496 | Fibroblast growth factor receptor 2 | Protein-tyrosine kinase activity, Fibroblast growth factor receptor activity |
| Hs.406460 | AA131718 | Hypothetical protein FLJ33814 | Unknown |
| Hs.446559 | N44262 | Full-length cDNA clone CS0DK010YA20 of HeLa cells Cot 25-normalized of *Homo sapiens* | Unknown |
| Hs.478429 | W61184 | ATPase, Class VI, type 11B | Phospholipid-translocating ATPase activity |
| Hs.4267 | R55942 | Hypothetical protein LOC284244 | |
| Hs.501991 | N95487 | Male sterility domain containing 2 | Catalytic activity, Nucleotide-sugar metabolism |
| Hs.490892 | H10810 | Microcephaly, primary autosomal recessive 1 | Unknown |
| No Unigene ID | R27946 | cDNA clone IMAGE: 134643 | Unknown |
| Hs.444450 | BQ049778 | Egl nine homolog 1 (*C. elegans*) | Oxidoreductase activity |
| Hs.655996 | T85025 | Transcribed locus | Unknown |
| Hs.298250 | N51782 | Methionine aminopeptidase 1D | Hydrolase activity, Methionyl aminopeptidase activity |
| Hs.202676 | BG218793 | Synaptonemal complex protein 2 | Cytokinesis, Cell cycle, Meiosis |
| Hs.31181 | BE741477 | G protein-coupled receptor 157 | Receptor activity, Rhodopsin-like receptor activity |
| Hs.390788 | AA127934 | Protein kinase, X-linked | ATP binding, CAMP-dependent protein kinase activity |
| Hs.183114 | H13748 | Rho GTPase activating protein 28 | Viral release, Membrane |
| No Unigene ID | AA128279 | cDNA clone IMAGE: 503368 | Unknown |
| Hs.471040 | H85748 | Hypothetical protein FLJ38973 | Unknown |
| Hs.402201 | W04859 | Transcribed locus | Unknown |

TABLE 3

Down-regulated genes, SAM, False discovery rate = 1%, Fold change >2

| Unigene ID | GenBank Accession No. | Fold change | q-value (%) | gene name | biologic process |
|---|---|---|---|---|---|
| Hs.1012 | H53489 | 0.32839206 | 0 | Complement component 4 binding protein, alpha | Immune response |
| Hs.512690 | W20504 | 0.36700642 | 0.70644385 | Surfactant, pulmonary-associated protein B | Respiratory gaseous exchange |
| Hs.159410 | BM549033 | 0.49381673 | 0.70644385 | Molybdenum cofactor synthesis 3 | Ligase activity |
| Hs.514167 | H39942 | 0.43082207 | 0.70644385 | Keratin 19 | Structural constituent of cytoskeleton |
| Hs.533977 | BM876583 | 0.4029923 | 0.70644385 | Thioredoxin interacting protein | Biological process unknown |
| Hs.335163 | T80552 | 0.39215165 | 0.70644385 | KIAA1102 protein | Zinc ion binding/Actin binding |
| Hs.531561 | R32270 | 0.3497418 | 0.70644385 | Epithelial membrane protein 2 | Cell death |
| Hs.517033 | R78823 | 0.46325094 | 0.70644385 | Transglutaminase 2 | Calcium ion binding |
| Hs.136348 | W35228 | 0.43969637 | 0.70644385 | Periostin, osteoblast specific factor | Cell adhesion |
| Hs.76686 | BG749189 | 0.4963755 | 0.70644385 | Glutathione peroxidase 1 | Oxidoreductase activity |
| Hs.411501 | H03673 | 0.38164517 | 0.70644385 | Keratin 7 | Structural molecule activity |
| Hs.445570 | R60600 | 0.48795268 | 0.70644385 | CD63 antigen | Growth regulation(Integral to membrane) |
| No Unigene ID | AV751900 | 0.4769848 | 0.70644385 | Not found | Not found |
| No Unigene ID | W52918 | 0.38437593 | 0.70644385 | Not found | Not found |
| Hs.191179 | W32118 | 0.49867186 | 0.70644385 | RAB11 family interacting protein 1 (class I) | intracellular transport |
| Hs.411501 | H27480 | 0.40039435 | 0.70644385 | Keratin 7 | Structural molecule activity |
| Hs.411501 | R26301 | 0.33074313 | 0.70644385 | Keratin 7 | Structural molecule activity |
| Hs.527412 | R25315 | 0.48579264 | 0.70644385 | N-acylsphingosine amidohydrolase (acid ceramidase) 1 | Carboxylic acid metabolism |
| Hs.525013 | AA125974 | 0.43524563 | 0.70644385 | Keratin, type II cytoskeletal 8 | the intermediate filament family |
| Hs.391561 | W15147 | 0.4739932 | 0.70644385 | Fatty acid binding protein 4, adipocyte | Transport |
| Hs.111779 | BG682138 | 0.47975752 | 0.70644385 | Secreted protein, acidic, cysteine-rich (osteonectin) | Ossification |
| Hs.284122 | W38638 | 0.46349898 | 0.70644385 | WNT inhibitory factor 1 | Cell-cell signaling |
| Hs.3972 | R28538 | 0.48654044 | 0.70644385 | ST6 (alpha-N-acetyl-neuraminyl-2,3-beta-galactosyl-1,3)-N-acetylgalactosaminide alpha-2,6-sialyltransferase 4 | Glycolipid metabolism |
| Hs.12271 | R54646 | 0.46289408 | 0.7104939 | F-box and leucine-rich repeat protein 6 | Ubiquitin conjugating enzyme activity |
| Hs.116471 | H25460 | 0.4515923 | 0.72283244 | Cadherin 11, type 2, OB-cadherin (osteoblast) | Homophilic cell adhesion |

TABLE 3-continued

Down-regulated genes, SAM, False discovery rate = 1%, Fold change >2

| Unigene ID | GenBank Accession No. | Fold change | q-value (%) | gene name | biologic process |
|---|---|---|---|---|---|
| Hs.435228 | R66683 | 0.49485594 | 0.7329108 | Synaptopodin | Actin binding |
| Hs.155342 | H11139 | 0.47693178 | 0.790798 | Protein kinase C, delta | ATP binding |
| No Unigene ID | H16541 | 0.49378946 | 0.790798 | Not found | Not found |
| Hs.233240 | BM996939 | 0.47034127 | 0.8530723 | Collagen, type VI, alpha 3 | Cell adhesion |
| Hs.309288 | R12062 | 0.47955394 | 0.9925388 | CUG triplet repeat, RNA binding protein 2 | Regulation of heart contraction rate |

TABLE 4

Down-regulated genes, Paired t-test, p < 0.01

| Unigene ID | GenBank Accession No. | Gene name | Funciton |
|---|---|---|---|
| Hs.503594 | H08943 | Angiomotin like 1 | muscle contraction |
| Hs.98791 | W04463 | ARP1 actin-related protein 1 homolog B, centractin beta (yeast) | Motor activity, Protein binding |
| Hs.412196 | H19027 | Estrogen-related receptor beta like 1 | Receptor activity |
| Hs.512690 | W20504 | Surfactant, pulmonary-associated protein B | Respiratory gaseous exchange, Regulation of liquid surface tension |

TABLE 5

The gene ratios with high diagnostic accuracy

| Gene selection | Denominator | Numerator | Diagnostic accuracy (%) |
|---|---|---|---|
| SAM | Hs.159410 | Hs.12409 | 92.3 |
|  | Hs.159410 | N31177 | 88.5 |
|  | Hs.514167 | Hs.128959 | 88.5 |
| Paired t test | Hs.503594 | Hs.446559 | 92.3 |
|  | Hs.503594 | Hs.533683 | 92.3 |
|  | Hs.98791 | T85025 | 88.5 |
|  | Hs.98791 | Hs.490892 | 88.5 |
|  | Hs.98791 | Hs.444450 | 88.5 |
|  | Hs.503594 | Hs.478429 | 88.5 |
|  | Hs.98791 | R27946 | 88.5 |
|  | Hs.503594 | R25303 | 88.5 |
|  | Hs.503594 | Hs.102788 | 88.5 |
|  | Hs.503594 | R27946 | 88.5 |
|  | Hs.503594 | Hs.31181 | 88.5 |
|  | Hs.503594 | T95563 | 88.5 |
|  | Hs.503594 | Hs.183114 | 88.5 |
|  | Hs.98791 | Hs.406460 | 88.5 |

TABLE 6

Demographic Characteristics of the Development and Validation Groups.

| Factor | Development Group (n = 84) No. of Cases (%) | Validation Group (n = 85) No. of Cases (%) | P Value |
|---|---|---|---|
| Donor risk characteristics | | | |
| Age: ≧55 yr | 21/84 (25) | 18/85 (21) | 0.56 |
| Female | 38/84 (45) | 44/85 (52) | 0.40 |
| Smoking history: ≧20 pack-years | 32/83 (39) | 20/85 (24) | 0.035 |
| Artery blood gas: <300 mmHg | 2/84 (2) | 1/85 (1) | 0.55 |
| Cause of death: traumatic head injury | 27/84 (32) | 35/85 (41) | 0.22 |
| Abnormal chest radiograph findings | 26/84 (31) | 20/84 (24) | 0.30 |
| Abnormal bronchoscopic finding | 19/84 (23) | 21/84 (25) | 0.72 |
| Sputum gram stain: positive | 53/84 (63) | 51/85 (60) | 0.68 |
| Time on the ventilator: >72 hr | 17/84 (20) | 16/85 (18) | 0.82 |
| ABO: compatible (vs. identical) | 6/84 (7) | 11/85 (13) | 0.21 |
| Recipient risk characteristics | | | |
| Female | 38/84 (45) | 38/85 (45) | 0.94 |
| Primary diagnosis | | | 0.31 |
| Emphysema | 21/84 (25) | 14/85 (16) | |
| Cystic fibrosis | 16/84 (19) | 26/85 (31) | |
| Pulmonary fibsosis | 18/84 (21) | 15/85 (18) | |
| α1-antitrypsin deficiency | 7/84 (8) | 7/85 (8) | |
| Primary pulmonary hypertension | 5/84 (6) | 4/85 (5) | |
| Bronchiectasis | 4/84 (5) | 1/85 (1) | |
| Congenital heart disease | 2/84 (2) | 4/85 (5) | |
| Re-Tx: Bronchiolitis obliterans | 3/84 (4) | 2/85 (2) | |
| Other | 7/84 (8) | 13/85 (15) | |
| Transplant procedure | | | |
| Type of transplantation | | | 0.14 |
| Single lung | 10/84 (12) | 4/85 (5) | |
| Bilateral lung | 73/84 (87) | 78/85 (92) | |
| Heart and lung | 1/84 (1) | 3/85 (4) | |
| Cold ischemic time (first lung) | | | 0.80 |
| ≦2 hr | 13/84 (15) | 13/85 (15) | |
| >2 hr, ≦4 hr | 47/84 (56) | 48/85 (56) | |
| >4 hr, ≦6 hr | 19/84 (23) | 21/85 (25) | |
| >6 hr, ≦8 hr | 4/84 (5) | 3/85 (4) | |
| >8 hr | 1/84 (1) | 0/85 (0) | |
| Use of cardiopulmonary bypass | 22/82 (27) | 22/80 (28) | 0.92 |
| Outcomes | | | |
| Death within 30 days | 10/84 (12) | 7/85 (8) | 0.43 |

TABLE 7

Univariate Effects of Cytokines and Ratios and Whole Model Test of Prediction Model of IL-6/IL-10*.

| Group | Odds Ratio (95% CI)§ | Wald Chi-square | P Value | Area under ROC Curve† (95% CI)§ |
|---|---|---|---|---|
| Development group (n = 84) | | | | |
| Cytokine | | | | |
| IL-6 | 1.42 (1.09-1.86) | 6.62 | 0.010 | 0.68 (0.50, 0.86) |
| IL-1β | 1.10 (0.98-1.24) | 2.58 | 0.11 | 0.59 (0.40, 0.79) |
| IL-8 | 1.29 (0.91-1.84) | 2.00 | 0.16 | 0.56 (0.38, 0.74) |
| IL-10 | 0.60 (0.23-1.54) | 1.13 | 0.29 | 0.48 (0.33, 0.63) |
| IFN-γ | 0.58 (0.24-1.39) | 1.48 | 0.22 | 0.38 (0.23, 0.53) |
| TNF-α | 1.16 (0.63-2.14) | 0.23 | 0.63 | 0.48 (0.27, 0.68) |
| Cytokine ratio | | | | |
| IL-6/IL-10 | 1.32 (1.07-1.63) | 6.68 | 0.010 | 0.74 (0.56, 0.91) |
| IL-1β/IFN-γ | 1.02 (1.00-1.04) | 4.34 | 0.037 | 0.73 (0.57, 0.90) |
| IL-6/IFN-γ | 1.05 (1.00-1.09) | 4.09 | 0.043 | 0.78 (0.63, 0.93) |
| IL-1β/IL10 | 1.09 (0.98-1.20) | 2.67 | 0.10 | 0.66 (0.46, 0.87) |
| IL-8/IL-10 | 1.07 (0.91-1.24) | 0.64 | 0.42 | 0.69 (0.53, 0.85) |
| TNF-α/IFN-γ | 1.01 (0.92-1.10) | 0.04 | 0.84 | 0.68 (0.51, 0.84) |
| TNF-α/IL-10 | 1.03 (0.73-1.47) | 0.03 | 0.85 | 0.60 (0.41, 0.78) |
| IL-8/IFN-γ | 1.00 (0.97-1.02) | <0.01 | 0.95 | 0.71 (0.58, 0.85) |
| Whole model test of IL-6/IL-10* | | 10.3 | 0.0013 | 0.74 (0.56, 0.91) |
| Validation group (n = 85) | | | | |
| Whole model test of IL-6/IL-10 | | 4.3 | 0.039 | 0.72 (0.53, 0.91) |
| All cases (n = 169) | | | | |
| Whole model test of IL-6/IL-10 | | 13.2 | 0.0003 | 0.72 (0.59, 0.85) |

*The prediction model was developed by stepwise logistic regression analysis and is expressed by the following equation:
logit (probability) = −2.8970 + 0.2785 × (IL-6/IL-10).
†ROC curve: receiver-operating characteristic curve.
§95% CI: 95 percent confidence interval shown as (lower, upper).

TABLE 8

Odds Ratio for 30-day Mortality According to the Risk Groups Defined by IL-6/IL-10.

| Risk group | No. of Cases (%) | Odds Ratio (95% CI)* | P value |
|---|---|---|---|
| Cut-off value 1† | | | |
| High | 42 (25%) | 5.45 (1.65-21.28) | 0.0076 |
| Intermediate | 43 (25%) | 2.05 (0.46-9.09) | 0.33 |
| Low | 84 (50%) | 1:reference | |
| Cut-off value 2§ | | | |
| High | 8 (5%) | 20.00 (3.64-121.34) | 0.0006 |
| Intermediate | 77 (45%) | 2.65 (0.82-10.12) | 0.12 |
| Low | 84 (50%) | 1:reference | |

*95% CI: 95 percent confidence interval shown as (lower, upper).
†The high risk group was defined as cases which fell into the highest quartile expression ratios of IL-6/IL-10, the intermediate risk group as those that fell in the second highest quartile and the low risk group as remaining half of cases with lowest expression ratio.
§The high risk group was defined as cases which fell into the highest 5% expression ratios of IL-6/IL-10, the intermediate risk group as those that fell in the following 45% and the low risk group as the remaining half of cases with lowest expression ratio.

TABLE 9

Primers for Six Cytokines and 18S ribosomal RNA.

| Gene | Forward Primer (5'-3') | Reverse Primer (5'-3') |
|---|---|---|
| IL-6 | CACACAGACAGCCACTCACC SEQ ID NO: 202 | TTTTCTGCCAGTGCCTCTTT SEQ ID NO: 203 |
| IL-8 | CAGGAATTGAATGGGTTTGC SEQ ID NO: 204 | AGCAGACTAGGGTTGCCAGA SEQ ID NO: 205 |
| IL-10 | AAGCCTGACCACGCTTTCTA SEQ ID NO: 206 | GCTCCCTGGTTTCTCTTCCT SEQ ID NO: 207 |
| IFN-γ | GTCCAACGCAAAGCAATACA SEQ ID NO: 208 | ATATTGCAGGCAGGACAACC SEQ ID NO: 209 |
| TNF-α | AGCCCATGTTGTAGCAAACC SEQ ID NO: 210 | TGAGGTACAGGCCCTCTGAT SEQ ID NO: 211 |
| IL-1β | GGACAAGCTGAGGAAGATGC SEQ ID NO: 212 | TCGTTATCCCATGTGTCGAA SEQ ID NO: 213 |
| 18S ribosomal RNA | GTAACCCGTTGAACCCCATT SEQ ID NO: 214 | CCATCCAATCGGTAGTAGCG SEQ ID NO: 215 |

TABLE 10

Demographic Characteristics of Donors among the Three Risk Groups Defined by Cut-off Value 1*.

| | Risk Group | | | |
|---|---|---|---|---|
| | High n = 42 (25%) | Intermediate n = 43 (25%) | Low n = 84 (50%) | P |
| Characteristics | No. of Cases (%) | | | Value |
| Age | | | | 0.84 |
| ≧55 yr | 11 (26) | 10 (23) | 18 (21) | |
| Gender | | | | 0.34 |

TABLE 10-continued

Demographic Characteristics of Donors among the Three Risk Groups Defined by Cut-off Value 1*.

| Characteristics | Risk Group | | | P Value |
|---|---|---|---|---|
| | High n = 42 (25%) | Intermediate n = 43 (25%) | Low n = 84 (50%) | |
| | No. of Cases (%) | | | |
| Female | 23 (55) | 23 (53) | 36 (43) | |
| Smoking history | | | | 0.92 |
| ≧20 pack-year | 14 (33) | 13/42 (31) | 25 (30) | |
| Cause of death | | | | 0.60 |
| Traumatic head injury | 18 (43) | 14 (33) | 30 (36) | |
| Time on ventilation | | | | 0.46 |
| >72 hr | 12 (29) | 7 (16) | 15 (18) | |
| Last PaO2/FiO2 | | | | 0.41 |
| <300 mmHg | 1 (2) | 0 (0) | 2 (2) | |
| Chest X-ray | | | | 0.84 |
| Localized abnormality | 13 (31) | 11/42 (26) | 22 (26) | |
| Bronchoscopic findings | | | | 0.18 |
| Abnormal | 12 (29) | 14/42 (33) | 16 (19) | |
| Sputum gram stain | | | | 0.48 |
| Positive | 24 (57) | 29 (67) | 52 (62) | |
| ABO compatibility | | | | 0.27 |
| Compatible | 7 (17) | 4 (9) | 6 (7) | |

*The three risk groups were defined by IL-6/IL-10 shown in Table 8.

TABLE 11

Demographic Characteristics of Recipient among the Three Risk Groups Defined by Cut-off Value 1*.

| Characteristics | Risk Group | | | P Value |
|---|---|---|---|---|
| | High n = 42 (25%) | Intermediate n = 43 (25%) | Low n = 84 (50%) | |
| | No. of Cases (%) | | | |
| Age | | | | 0.31 |
| >60 yr | 6 (14) | 9 (21) | 9 (11) | |
| Gender | | | | 0.20 |
| Female | 22 (52) | 22 (51) | 32 (38) | |
| Primary disease | | | | 0.99 |
| Emphysema | 9 (21) | 10 (23) | 17 (20) | |
| Cystic fibrosis | 9 (21) | 9 (21) | 24 (29) | |
| IPF | 6 (14) | 8 (19) | 18 (21) | |
| α1-antitrypsin deficiency | 4 (10) | 4 (9) | 6 (7) | |
| PPH | 3 (7) | 2 (5) | 4 (5) | |
| Bronchiectasis | 1 (2) | 2 (5) | 2 (2) | |
| Congenital heart disease | 2 (5) | 1 (2) | 3 (4) | |
| Re-transplant (BOS) | 2 (5) | 1 (2) | 2 (2) | |
| Others | 6 (14) | 6 (14) | 8 (10) | |
| Procedure | | | | 0.17 |
| Single lung | 4 (10) | 1 (2) | 9 (11) | |
| Bilateral lung | 36 (86) | 42 (98) | 73 (87) | |
| Heart and lung | 2 (5) | 0 (0) | 2 (2) | |
| Cardiopulmonary bypass use | | | | 0.95 |
| Use | 12 (29) | 11 (26) | 22 (27) | |

*The three risk groups were defined by IL-6/IL-10 shown in Table 8.

TABLE 12

Demographic Characteristics of Donors among the Three Risk Groups Defined by Cut-off Value 2*.

| Characteristics | Risk Group | | | P Value |
|---|---|---|---|---|
| | High n = 8 (5%) | Intermediate n = 77 (45%) | Low n = 84 (50%) | |
| | No. of Cases (%) | | | |
| Age | | | | 0.59 |
| ≧55 yr | 1 (13) | 20 (26) | 18 (21) | |
| Gender | | | | 0.30 |
| Female | 5 (63) | 41 (53) | 36 (43) | |
| Smoking history | | | | 0.17 |
| ≧20 pack-year | 5 (63) | 22/76 (29) | 25 (30) | |
| Cause of death | | | | 0.70 |
| Traumatic head injury | 2 (25) | 30 (39) | 30 (36) | |
| Time on ventilation | | | | 0.69 |
| >72 hr | 1 (13) | 17 (22) | 15 (18) | |
| Last PaO2/FiO2 | | | | 0.76 |
| <300 mmHg | 0 (0) | 1 (1) | 2 (2) | |
| Chest X-ray | | | | 0.80 |
| Localized abnormality | 3 (38) | 21/76 (28) | 22 (26) | |
| Bronchoscopic findings | | | | 0.19 |
| Abnormal | 2 (25) | 24/76 (32) | 16 (19) | |
| Sputum gram stain | | | | 0.68 |
| Positive | 6 (75) | 46 (60) | 52 (62) | |
| ABO compatibility | | | | 0.14 |
| Compatible | 0 (0) | 11 (14) | 6 (7) | |

*The three risk groups were defined by IL-6/IL-10 shown in Table 8.

TABLE 13

Demographic Characteristics of Recipient among the Three Risk Groups Defined by Cut-off Value 2*.

| Characteristics | Risk Group | | | P Value |
|---|---|---|---|---|
| | High n = 8 (5%) | Intermediate n = 77 (45%) | Low n = 84 (50%) | |
| | No. of Cases (%) | | | |
| Age | | | | 0.37 |
| >60 yr | 2 (25) | 13 (17) | 9 (11) | |
| Gender | | | | 0.16 |
| Female | 5 (63) | 39 (51) | 32 (38) | |
| Primary disease | | | | 0.77 |
| Emphysema | 2 (25) | 17 (22) | 17 (20) | |
| Cystic fibrosis | 0 (0) | 18 (23) | 24 (29) | |
| IPF | 1 (13) | 13 (17) | 18 (21) | |
| α1-antitrypsin deficiency | 1 (13) | 7 (9) | 6 (7) | |
| PPH | 1 (13) | 4 (5) | 4 (5) | |
| Bronchiectasis | 0 (0) | 3 (4) | 2 (2) | |
| Congenital heart disease | 0 (0) | 3 (4) | 3 (4) | |
| Re-transplant (BOS) | 0 (0) | 3 (4) | 2 (2) | |
| Others | 3 (38) | 9 (12) | 8 (10) | |
| Procedure | | | | 0.69 |
| Single lung | 1 (13) | 4 (5) | 9 (11) | |
| Bilateral lung | 7 (88) | 71 (92) | 73 (87) | |
| Heart and lung | 0 (0) | 2 (3) | 2 (2) | |
| Cardiopulmonary bypass use | | | | 0.085 |
| Use | 5 (63) | 18 (23) | 22 (27) | |

*The three risk groups were defined by IL-6/IL-10 shown in Table 8.

We claim:

1. A method of screening for decreased risk of primary graft failure of a lung transplant, comprising the steps:
    (a) obtaining a sample of a human donor lung;
    (b) determining the level of RNA product of one or more biomarkers selected from the biomarkers human microephaly, autosomal recessive 1 (MCPH1), human fibroblast growth factor receptor 2 (FGFR2), human ATPase, Class VI, type 11B (ATP11B) and human Egl nine homolog 1 (EGLN1) in said sample;
    (c) comparing the level of one or more RNA products in the sample with levels in control lung samples of human patients which survived less than 30 days after lung transplant; and
    (d) detecting statistically significant decreased expression of the RNA product or products between the donor lung and the control lung samples, wherein a statistically significant decreased expression has a p-value less than 0.05, by a Student's t-test and identifying the donor lung with said statistically significant decreased expression as having decreased risk for primary graft failure relative to a human donor lung that does not have said decreased expression.

2. The method according to claim 1, wherein the step of determining the level of said RNA products comprises using quantitative RT-PCR.

3. The method according to claim 1, wherein the step of determining the level of said RNA products comprises using rapid RT-PCR.

4. The method according to claim 1, wherein the step of determining the level of said RNA products comprises using a microarray.

5. The method of claim 1 wherein the level of RNA of two of the biomarkers is determined.

6. The method of claim 5, wherein the level of RNA products is compared in step b) by comparing the ratios of the two biomarkers, wherein an increased ratio between the donor lung and the controls is indicative of risk for primary graft failure.

7. The method of claim 1, wherein the biomarker selected is MCPH1 and wherein the method further comprises determining the level of RNA product of human ARP1 actin-related protein 1 homolog B, centractin beta in the sample and the controls, calculating the ratio of the levels of RNA product of MCPH1/ARP1 actin-related protein 1 homolog B, centractin beta, wherein the level of RNA products is compared in step b) by comparing the ratios of the levels of RNA product of MCPH1/ARP1 actin-related protein 1 homolog B, centractin beta, in the sample and the controls, and wherein an increased ratio between the donor lung and the controls is indicative of risk for primary graft failure.

8. The method of claim 1 wherein the biomarker selected is FGFR2 and wherein the method further comprises determining the level of RNA product of human Angiomotin like 1 in the sample and the controls, calculating the ratio of the levels of RNA product of FGFR2/Angiomotin like 1, wherein the level of RNA products is compared in step b) by comparing the ratios of the levels of RNA product of FGFR2/Angiomotin like 1 in the sample and the controls, and wherein an increased ratio between the donor lung and the controls is indicative of risk for primary graft failure.

9. The method of claim 1 wherein the biomarker selected is EGLN1 and wherein the method further comprises determining the level of RNA product of ARP1 actin-related protein 1 homolog B, centractin beta in the sample and the controls, calculating the ratio of the levels of RNA product of human EGLN1/ARP1 actin-related protein 1 homolog B, centractin beta, wherein the level of RNA products is compared in step b) by comparing the ratios of the levels of RNA product of EGLN1/ARP1 actin-related protein 1 homolog B, centractin beta in the sample and the controls, and wherein an increased ratio between the donor lung and the controls is indicative of risk for primary graft failure.

10. The method of claim 1 wherein the biomarker selected is ATP11B and wherein the method further comprises determining the level of RNA product of human Angiomotin like 1 in the sample and the controls, calculating the ratio of the levels of RNA product of ATP11B/Angiomotin like 1, wherein the level of RNA products is compared in step b) by comparing the ratios of the levels of RNA product of ATP11B/Angiomotin like 1 in the sample and the controls, and wherein an increased ratio between the donor lung and the controls is indicative of risk for primary graft failure.

11. The method of claim 1 wherein the level of RNA of four of the biomarkers is determined.

12. A method of screening for increased risk of primary graft failure of a lung transplant, comprising the steps:
    (a) obtaining a sample of a human donor lung;
    (b) determining the level of RNA product of one or more biomarkers selected from the biomarkers human microephaly, autosomal recessive 1 (MCPH1), human fibroblast growth factor receptor 2 (FGFR2), human ATPase, Class VI, type 11B (ATP11B) and human Egl nine homolog 1 (EGLN1) in said sample;

(c) comparing the level of one or more RNA products in the sample with levels in control lung samples of human patients which survived over 6 months after lung transplantation; and
(d) detecting statistically significant increased expression of the RNA product or products between the donor lung and the control lung samples wherein a statistically significant increased expression has a p-value less than 0.05, by a Student t-test and identifying the donor lung with said statistically significant increased expression as having increased risk for primary graft failure relative to a human donor lung that does not have said increased expression.

* * * * *